US012799146B2

(12) United States Patent
He et al.

(10) Patent No.: US 12,799,146 B2
(45) Date of Patent: Nov. 17, 2026

(54) COMPOSITIONS AND METHODS RELATED TO MODIFICATION AND DETECTION OF PSEUDOURIDINE AND 5-HYDROXYMETHYLCYTOSINE

(71) Applicant: THE UNIVERSITY OF CHICAGO, Chicago, IL (US)

(72) Inventors: Chuan He, Chicago, IL (US); Qing Dai, Chicago, IL (US); Lisheng Zhang, Chicago, IL (US); Chang Ye, Chicago, IL (US)

(73) Assignee: The University of Chicago, Chicago, IL (US)

( * ) Notice: Subject to any disclaimer, the term of this patent is extended or adjusted under 35 U.S.C. 154(b) by 498 days.

(21) Appl. No.: 18/556,842

(22) PCT Filed: Apr. 27, 2022

(86) PCT No.: PCT/US2022/071947
§ 371 (c)(1),
(2) Date: Oct. 23, 2023

(87) PCT Pub. No.: WO2022/232795
PCT Pub. Date: Nov. 3, 2022

(65) Prior Publication Data

US 2025/0154187 A1 May 15, 2025

Related U.S. Application Data

(60) Provisional application No. 63/180,304, filed on Apr. 27, 2021.

(51) Int. Cl.

| | |
|---|---|
| ***C07H 1/00*** | (2006.01) |
| ***C12N 9/12*** | (2006.01) |
| ***C12Q 1/6806*** | (2018.01) |
| ***C12Q 1/6869*** | (2018.01) |

(52) U.S. Cl.
CPC ............ *C07H 1/00* (2013.01); *C12N 9/1276* (2013.01); *C12Q 1/6806* (2013.01); *C12Q 1/6869* (2013.01); *C12Y 207/07049* (2013.01)

(58) Field of Classification Search
None
See application file for complete search history.

(56) References Cited

U.S. PATENT DOCUMENTS

| | | | | |
|---|---|---|---|---|
| 5,143,854 | A | 9/1992 | Pirrung et al. | |
| 5,384,261 | A | 1/1995 | Winkler et al. | |
| 5,424,186 | A | 6/1995 | Fodor et al. | |
| 5,445,934 | A | 8/1995 | Fodor et al. | |
| 5,677,195 | A | 10/1997 | Winkler et al. | |
| 5,708,153 | A | 1/1998 | Dower et al. | |
| 5,744,305 | A | 4/1998 | Fodor et al. | |
| 5,770,358 | A | 6/1998 | Dower et al. | |
| 5,789,162 | A | 8/1998 | Dower et al. | |
| 5,800,992 | A | 9/1998 | Fodor et al. | |
| 6,040,193 | A | 3/2000 | Winkler et al. | |
| 8,741,567 | B2 | 6/2014 | He et al. | |
| 9,611,510 | B2 | 4/2017 | He et al. | |
| 11,130,991 | B2 | 9/2021 | He et al. | |
| 2007/0190530 | A1 * | 8/2007 | Birkner | C07H 21/00 536/28.4 |
| 2014/0087449 | A1 * | 3/2014 | Ballhause | C12Q 1/6806 435/270 |
| 2017/0137871 | A1 | 5/2017 | Lai et al. | |
| 2018/0119225 | A1 | 5/2018 | Rao et al. | |
| 2021/0310062 | A1 | 10/2021 | He et al. | |

FOREIGN PATENT DOCUMENTS

| | | | |
|---|---|---|---|
| CN | 105907854 A | 8/2016 | |
| WO | WO 2005/100240 | 10/2005 | |
| WO | WO-2012138973 A2 * | 10/2012 | C12Q 1/6869 |
| WO | WO 2014/083118 | 6/2014 | |
| WO | WO 2014/165770 | 10/2014 | |
| WO | WO 2020/228306 | 11/2020 | |
| WO | WO 2022/232795 | 11/2022 | |
| WO | WO 2023/133533 | 7/2023 | |

OTHER PUBLICATIONS

Khoddami, V., Yerra, A., Mosbruger, T. L., Fleming, A. M., Burrows, C. J., & Cairns, B. R. (2019). Transcriptome-wide profiling of multiple RNA modifications simultaneously at single-base resolution. Proceedings of the National Academy of Sciences, 116(14), 6784-6789. (Year: 2019).*

"Ammonium Bisulphite Solution 70%", Esseco UK Limited, Technical Data Sheet, Issue No. 7, Document Reference: PS 3C, 1 page, Mar. 2013.

"Ammonium Sulfate, 10% (w/v), Ricca Chemical", Ammonium Sulfate, 10% (w/V), Ricca Chemical, Quantity: Each of 1 | Fisher Scientific, Web: https://www.fishersci.com/shop/products/ammonium-sulfate-10-w-v-ricca-chemical-2/694216, 3 pages, 2015.

Applebaum et al., "5-Hydroxymethylcytosine profiles are prognostic of outcome in neuroblastoma and reveal transcriptional networks that correlate with tumor phenotype.", JCO Precision Oncol., 3:1-12, 2019.

Babaian et al., "Loss of m1acp3Ψ ribosomal RNA modification is a major feature of cancer", Cell Rep., 31(5), 30 pages, 2020.

Bakin et al., "Four newly located pseudouridylate residues in *Escherichia coli* 23S ribosomal RNA are all at the peptidyltransferase center: analysis by the application of a new sequencing technique", Biochemistry, 32(37):9754-9762, 1993.

Balakin et al., "The RNA world of the nucleolus: two major families of small RNAs defined by different box elements with related functions", Cell, 86(5):823-834, 1996.

(Continued)

*Primary Examiner* — Dale R Miller
(74) *Attorney, Agent, or Firm* — Norton Rose Fulbright US LLP

(57) ABSTRACT

Aspects of the present disclosure are directed to methods and compositions for modification, detection, and quantification of pseudouridine and 5-hydroxymethylcytosine. Disclosed are methods for modification of pseudouridine and/or 5-hydroxymethylcytosine comprising bisulfite treatment under particular conditions. Further disclosed are compositions and kits comprising a bisulfite solution and instructions for use.

16 Claims, 46 Drawing Sheets

Specification includes a Sequence Listing.

(56) References Cited

OTHER PUBLICATIONS

Blanco et al., "Aberrant methylation of tRNAs links cellular stress to neuro-developmental disorders", EMBO J., 33(18):2020-2039, 2014.
Borchardt et al., "Regulation and Function of RNA Pseudouridylation in Human Cells", Annu. Rev. Genet., 54:309-336, 2020.
Bykhovskaya et al., "Missense mutation in pseudouridine synthase 1 (PUS1) causes mitochondrial myopathy and sideroblastic anemia (MLASA)", Am. J. Hum. Genet., 74:1303-1308, 2004.
Cai et al., "Genome-wide mapping of 5-hydroxymethylcytosines in circulating cell-free DNA as a non-invasive approach for early detection of hepatocellular carcinoma", Gut, 68:2195-2205, 2019.
Carlile et al., "Pseudouridine profiling reveals regulated mRNA pseudouridylation in yeast and human cells", Nature, 515(7525):143-146, 2014.
Chen et al., "5-methylcytosine promotes pathogenesis of bladder cancer through stabilizing mRNAs", Nat. Cell Biol., 21:978-990, 2019.
Cheng et al., "RNA cytosine methylation and methyltransferases mediate chromatin organization and 5-azacytidine response and resistance in leukaemia", Nat. Commun., 9(1163):1-16, 2018.
Cheray et al., "Cytosine methylation of mature microRNAs inhibits their functions and is associated with poor prognosis in glioblastoma multiforme", Mol. Cancer, 19(36)1-16, 2020.
Chiu et al., "Prognostic implications of 5-hydroxymethylcytosines from circulating cell-free DNA in diffuse large B-cell lymphoma", Blood Adv., 3(19):2790-2799, 2019.
Cui et al., "5-Methylcytosine RNA Methylation in Arabidopsis Thaliana", Mol. Plant, 10:1387-1399, 2017.
Cui et al., "Targeting PUS7 suppresses tRNA pseudouridylation and glioblastoma tumorigenesis", Nat. Cancer, 2(9):932-949, 2021.
Dai et al., "Quantitative sequencing using BID-seq uncovers abundant pseudouridines in mammalian mRNA at base resolution", Nat. Biotechnol., 41:344-354, 2023.
Dai et al., "Ultrafast bisulfite sequencing detection of 5-methylcytosine in DNA and RNA", Nature Biotechnology, 42(10):1559-1570, 2024.
De Brouwer et al., "Variants in PUS7 Cause Intellectual Disability with Speech Delay, Microcephaly, Short Stature, and Aggressive Behavior", Am J Hum Genet, 103:1045-1052, 2018.
De Zoysa et al., "Posttranscriptional RNA Pseudouridylation", Enzymes, 41:151-167, 2017.
Delatte et al., "Transcriptome-wide distribution and function of RNA hydroxymethylcytosine", Science, 351(6270):282-5, 2016.
Dietrich et al., "Diagnostic and Prognostic Value of SHOX2 and SEPT9 DNA Methylation and Cytology in Benign, Paramalignant and Malignant Pleural Effusions", Plos One, 8(12):e84225, 9 pages, 2013.
Dietrich et al., "Improved PCR Performance Using Template DNA from Formalin-Fixed and Paraffin-Embedded Tissues by Overcoming PCR Inhibition", PLoS ONE, 8(10):e77771, 10 pages, 2013.
Dong et al., "5-Hydroxymethylcytosine signatures in circulating cell-free DNA as diagnostic and predictive biomarkers for coronary artery disease", Clin. Epigenetics, 12(17):1-13, 2020.
Dor et al., "Principles of DNA methylation and their implications for biology and medicine", The Lancet, 392:777-786, 2018.
Edelheit et al., "Transcriptome-wide mapping of 5-methylcytidine RNA modifications in bacteria, archaea, and yeast reveals m5C within archaeal mRNAs", PLoS Genet., 9(6):e1003602, 14 pagese, 2013.
Evers et al., "The Effect of Formaldehyde Fixation on RNA, Optimization of Formaldehyde Adduct Removal", The Journal of Molecular Diagnostics, 13(3):282-288, 2011.
Extended European Search Report and Written Opinion for Application No. 23737801.3, mailed Nov. 28, 2025, 15 pages.
Eyler et al., "Pseudouridinylation of mRNA coding sequences alters translation", Proc. Natl. Acad. Sci. USA, 116(46):23068-23074, 2019.
Fabyanic et al., "Quantitative single cell 5hmC sequencing reveals non-canonical gene regulation by non-CG hydroxymethylation", bioRxiv, URL:https://www.biorxiv.org/content/biorxiv/early/2021/03/24/2021.03.23.434325.1.full.pdf, 40 pages, 2021.
Fernández et al., "Unusual base pairing during the decoding of a stop codon by the ribosome", Nature, 500(7460):107-110, 2013.
Fleming et al., "Structural Elucidation of Bisulfite Adducts to Pseudouridine That Result in Deletion Signatures during Reverse Transcription of Rna", J. Am. Chem. Soc., 141(41):16450-16460, 2019.
Flusberg et al., "Direct detection of DNA methylation during single-molecule, real-time sequencing", Nat. Methods., 7(6):461-465, 2010.
Frommer et al., "A genomic sequencing protocol that yields a positive display of 5-methylcytosine residues in individual DNA strands", Proceedings of the National Academy of Sciences, 89:1827-1831, 1992.
Frye et al., "RNA modifications modulate gene expression during development", Science, 361(6409):1346-1349, 2018.
Ganot et al., "Site-specific pseudouridine formation in preribosomal RNA is guided by small nucleolar RNAs", Cell, 89:799-809, 1997.
Garcia et al., "A prion accelerates proliferation at the expense of lifespan", eLife, 10:e60917, 41 pages, 2021.
Genereux et al., "Errors in the bisulfite conversion of DNA: modulating inappropriate- and failed-conversion frequencies", Nucleic Acids Res., 36(22):e150, 19 pages, 2008.
Grozdanov et al., "Pathogenic NAP57 mutations decrease ribonucleoprotein assembly in dyskeratosis congenita", Hum Mol Genet., 18(23):4546-51, 2009.
Grunau et al., "Bisulfite genomic sequencing: systematic investigation of critical experimental parameters", Nucleic Acids Res, 29(13): e65, 7 pages, 2001.
Guzzi et al., "Pseudouridylation of tRNA-Derived Fragments Steers Translational Control in Stem Cells", Cell , 173:1204-1216, 2018.
Hacia et al., "Detection of heterozygous mutations in BRCA1 using high density oligonucleotide arrays and two-colour fluorescence analysis", Nature Genetics, 14(4):441-447, 1996.
Hamma et al., "Pseudouridine synthases", Chemistry and Biology, 13:1125-1135, 2006.
Han et al., "A highly sensitive and robust method for genome-wide 5hmC profiling of rare cell populations", Mol. Cell, 63:711-719, 2016.
Hayatsu et al., "Reaction of sodium bisulfite with uracil, cytosine, and their derivatives", Biochemistry, 9(14):2858-2865, 1970.
Hayatsu et al., "DNA methylation analysis: speedup of bisulfite-mediated deamination of cytosine in the genomic sequencing procedure", Proceedings of the Japan Academy, Series B, 80(4):189-194, 2004.
Hayatsu, H., "Bisulfite Modification of Cytosine and 5-Methylcytosine as used in Epigenetic Studies", Genes Environ., 28(1):1-8, 2006.
Hayatsu, H., "Discovery of bisulfite-mediated cytosine conversion to uracil, the key reaction for DNA methylation analysis—a personal account", Proc. Jpn. Acad. Ser. B Phys. Biol. Sci., 84:321-330, 2008.
Hayatsu, H., "The bisulfite genomic sequencing used in the analysis of epigenetic states, a technique in the emerging environmental genotoxicology research", Mutat. Res., 659:77-82, 2008.
He et al., "Role of m5C-related regulatory genes in the diagnosis and prognosis of hepatocellular carcinoma", Am. J. Transl. Res., 12(3):912-922, 2020.
Heiss et al., "X-linked dyskeratosis congenita is caused by mutations in a highly conserved gene with putative nucleolar functions", Nat. Genet., 19:32-38, 1998.
Hu et al., "m6A RNA modifications are measured at single-base resolution across the mammalian transcriptome", Nat. Biotechnol., 40(8):1210-1219, 2022.
Huang et al., "Genome-wide identification of mRNA 5-methylcytosine in mammals", Nat. Struct. Mol. Biol., 26:380-388, 2019.
Huang et al., "The anti-CMS technique for genome-wide mapping of 5-hydroxymethylcytosine ," Nature Protocols, 7(10):1897-1908, 2012.
Huang et al., "The behaviour of 5-hydroxymethylcytosine in bisulfite sequencing," PLoS ONE, 5(1):e8888, pp. 1-9, 2010.

(56) References Cited

OTHER PUBLICATIONS

Hussain et al., "Characterizing 5-methylcytosine in the mammalian epitranscriptome", Genome Biol., 14(215)1-10, 2013.
International Search Report and Written Opinion for Application No. PCT/US23/60267, mailed Jul. 18, 2023, 33 pages.
International Search Report and Written Opinion received in International Application No. PCT/US2022/071947, mailed Sep. 9, 2022, 23 pages.
Jambhekar et al., "Cis-acting determinants of asymmetric, cytoplasmic RNA transport", RNA, 13:625-642, 2007.
Janin et al., "Epigenetic loss of RNA-methyltransferase NSUN5 in glioma targets ribosomes to drive a stress adaptive translational program", Acta Neuropathol. (Berl.), 138:1053-1074, 2019.
Karijolich et al., "Converting nonsense codons into sense codons by targeted pseudouridylation", Nature, 474(7351):395-398, 2011.
Karikó et al., "Incorporation of pseudouridine into mRNA yields superior nonimmunogenic vector with increased translational capacity and biological stability", Mol. Ther., 16(11):1833-1840, 2008.
Khoddami et al., "Identification of direct targets and modified bases of RNA cytosine methyltransferases", Nat. Biotechnol., 31(5):458-464, 2013.
Khoddami et al., "Transcriptome-wide profiling of multiple RNA modifications simultaneously at single-base resolution," Proc Natl Acad Sci U S A., 116(14):6784-6789, 2019.
Kudla et al., "Coding-sequence determinants of expression in *Escherichia coli*", Science. 324(5924):255-258, 2009.
Kuo et al., "Quantitative reversed-phase high performance liquid chromatographic determination of major and modified deoxyribonucleosides in DNA*", Nucleic Acids Res., 8(20):4763-4776, 1980.
Laszlo et al., "Detection and mapping of 5-methylcytosine and 5-hydroxymethylcytosine with nanopore MspA", PNAS, 110(47):18904-18909, 2013.
Lee et al., "Increased urinary level of oxidized nucleosides in patients with mild-to-moderate Alzheimer's disease", Clin. Biochem., 40:936-938, 2007.
Legrand et al., "Statistically robust methylation calling for whole-transcriptome bisulfite sequencing reveals distinct methylation patterns for mouse RNAs", Genome Res., 27:1589-1596, 2017.
Li et al., "5-Hydroxymethylcytosine signatures in circulating cell-free DNA as diagnostic biomarkers for human cancers", Cell Res., 27:1243-1257, 2017.
Li et al., "Chemical pulldown reveals dynamic pseudouridylation of the mammalian transcriptome", Nat. Chem. Biol., 11:592-7, 2015.
Lovejoy et al., "Transcriptome-Wide Mapping of Pseudouridines: Pseudouridine Synthases Modify Specific mRNAs in S. cerevisiae", PLoS One, 9(10): e110799, 15 pages, 2014.
Loyfer et al., "A DNA methylation atlas of normal human cell types", Nature, 613:355-364, 2023.
Martinez et al., "Pseudouridine synthases modify human pre-mRNA co-transcriptionally and affect pre-mRNA processing", Mol. Cell, 82:645-659, 2022.
Ni et al., "Small nucleolar RNAs direct site-specific synthesis of pseudouridine in ribosomal RNA", Cell, 89:565-573, 1997.
Olova et al., "Comparison of whole-genome bisulfite sequencing library preparation strategies identifies sources of biases affecting DNA methylation data", Genome Biol., 19(33), 19 pages, 2018.
Pastor et al., "Genome-wide mapping of 5-hydroxymethylcytosine in embryonic stem cells", Nature, 473(7347):394-7, 2011.
Pease et al., "Light-generated oligonucleotide arrays for rapid DNA sequence analysis", Proc. Natl. Acad. Sci. USA, 91:5022-5026, 1994.
Penzo et al., "RNA pseudouridylation in physiology and medicine: For better and for worse", Genes, 8(301):1-14, 2017.
Promega Corporation, "MethylEdge Bisulfite Conversion System, Instructions for Use of Product N1301", Technical Manual, Part# TM381, 9 pages.
Purchal et al., "Pseudouridine synthase 7 is an opportunistic enzyme that binds and modifies substrates with diverse sequences and structures", Proc. Natl. Acad. Sci. USA, 119(4):e2109708119, 9 pages, 2022.
Qiagen, "Quick-Start Protocol: EpiTect Fast 96 DNA Bisulfite Kit—Part 2", 2 pages, 2016.
Qiagen, "Quick-Start Protocol: EpiTect Fast DNA Bisulfite Kit—Part 1", 2 pages, 2012.
RayBiotech Inc., "DNA Bisulfite Conversion Kit (Magnetic Bead Method)", Catalog #: NAE-BIS-MAG, Manual, 6 pages, 2024.
Rintala-Dempsey et al., "Eukaryotic stand-alone pseudouridine synthases-RNA modifying enzymes and emerging regulators of gene expression?", RNA Biology, 14(9):1185-1196, 2017.
Roundtree et al., "Dynamic RNA modifications in gene expression regulation", Cell, 169:1187-1200, 2017.
Safra et al., "TRUB1 is the predominant pseudouridine synthase acting on mammalian mRNA via a predictable and conserved code", Genome Res., 27:393-406, 2017.
Schaefer et al., "RNA cytosine methylation analysis by bisulfite sequencing", Nucleic Acids Res., 37(2):e12, 10 pages, 2009.
Schreiber et al., "Error rates for nanopore discrimination among cytosine, methylcytosine, and hydroxymethylcytosine along individual DNA strands", PNAS, 110(47):18910-18915, 2013.
Schutsky et al., "Nondestructive, base-resolution sequencing of 5-hydroxymethylcytosine using a DNA deaminase", Nat. Biotechnol., 36(11):1083-1090, 2018.
Schwartz et al., "Transcriptome-wide mapping reveals widespread dynamic-regulated pseudouridylation of ncRNA and mRNA", Cell, 159(1):148-162, 2014.
Shah et al., "Rate-limiting steps in yeast protein translation", Cell, 153(7):1589-1601, 2013.
Shapiro et al., "Deamination of cytosine derivatives by bisulfite. Mechanism of the reaction", J. Am. Chem. Soc., 96(3):906-912, 1974.
Shiraishi et al., "High-speed conversion of cytosine to uracil in bisulfite genomic sequencing analysis of DNA methylation", DNA Res., 11:409-415, 2004.
Somogyi et al., "Ribosomal pausing during translation of an RNA pseudoknot", Mol. Cell. Biol., 13(11):6931-6940, 1993.
Song et al., "5-Hydroxymethylcytosine signatures in cell-free DNA provide information about tumor types and stages", Cell Res., 27:1231-1242, 2017.
Song et al., "Differential roles of human PUS10 in miRNA processing and tRNA pseudouridylation", Nat. Chem. Biol., 16:160-169, 2020.
Song et al., "Selective chemical labeling reveals the genome-wide distribution of 5-hydroxymethylcytosine", Nat. Biotechnol., 29(1):68-72, 2011.
Sono et al., "Role of bisulfite in the deamination and the hydrogen isotope exchange of cytidylic acid", J. Am. Chem. Soc., 95(14):4745-4749, 1973.
Squires et al., "Widespread occurrence of 5-methylcytosine in human coding and non-coding RNA", Nucleic Acids Res., 40(11):5023-5033, 2012.
Tan et al., "Tiling genomes of pathogenic viruses identifies potent antiviral shRNAs and reveals a role for secondary structure in shRNA efficacy", Proc. Natl. Acad. Sci. U. S. A., 109(3):869-874, 2012.
Tanaka et al., "Degradation of DNA by bisulfite treatment", Bioorganic Med. Chem. Lett., 17:1912-1915, 2007.
Taoka et al., "Landscape ofthe complete RNA chemical modifications in the human 80S ribosome", Nucleic Acids Res., 46(18):9289-9298, 2018.
Tian et al., "Circulating tumor DNA 5-hydroxymethylcytosine as a novel diagnostic biomarker for esophageal cancer", Cell Res., 28:597-600, 2018.
Torres et al., "Role of tRNA modifications in human diseases", Trends in Molecular Medicine, 20(6):306-314, 2014.
Wilson et al., "Programmable m6A modification of cellular RNAs with a Cas13-directed methyltransferase", Nat. Biotechnol., 38(12):1431-1440, 2020.

(56) References Cited

OTHER PUBLICATIONS

Wojtczyk-Miaskowska et al., "Gene Expression, DNA Methylation and Prognostic Significance of DNA Repair Genes in Human Bladder Cancer", Cell Physiol Biochem, 42:2404-2417, 2017.
Wu et al., "Genome-wide analysis of 5-hydroxymethylcytosine distribution reveals its dual function in transcriptional regulation in mouse embryonic stem cells", Genes Dev., 25:679-684, 2011.
Yang et al., "5-Hydroxymethylcytosines in circulating cell-free DNA reveal vascular complications of type 2 diabetes", Clin. Chem., 65(11):1414-1425, 2019.
Yang et al., "5-methylcytosine promotes mRNA export—NSUN2 as the methyltransferase and ALYREF as an m5C reader", Cell Res., 27:606-625, 2017.
Yi et al., "An optimized rapid bisulfite conversion method with high recovery of cell-free DNA", BMC Mol. Biol., 18(24), 8 pages, 2017.
Yu et al., "Base-resolution detection of N4-methylcytosine in genomic DNA using 4mC-Tet-assisted-bisulfite-sequencing", Nucleic Acids Research, 43(21):e148, 10 pages, 2015.
Zaringhalam et al., "Pseudouridylation meets next-generation sequencing", Methods, 107:63-72, 2016.
Zhang et al., "ALKBH7-mediated demethylation regulates mitochondrial polycistronic RNA processing", Nat. Cell Biol., 23(7):684-691, 2021.
Zhang et al., "Sensitive and quantitative probing of pseudouridine modification in mRNA and long noncoding RNA", RNA, 25:1218-1225, 2019.
Zhang et al., "Systematic calibration of epitranscriptomic maps using a synthetic modification-free RNA library", Nat. Methods, 18:1213-1222, 2021.
Zymo Research, "EZ DNA Methylation-Gold Kit", Catalog Nos. D5005 & D5006, Instruction Manual Ver.2.1.5, 18 pages, 2021.
Zymo Research, "EZ RNA Methylation Kit", Catalog Nos. R5001 & R5002, Instruction Manual, 11 pages.
Zymo Research, "EZ-96 DNA Methylation-Lightning Kit (Deep-Well Format)", Catalog Nos. D5033, Instruction Manual Ver.1.0.3, 16 pages, 2022.
Zymo Research, "EZ-96 DNA Methylation-Lightning Kit (Shallow-Well Format)", Catalog Nos. D5032, Instruction Manual Ver.1.0.3, 16 pages, 2022.

* cited by examiner

Spike-In Ψ Probe Sequences:

➤ G UAC GUC AGΨ CAG ACU GAC (SEQ ID NO:5)

One of the 256 calibration curves

A GCU AGU NNΨNNU AGU GAC
(SEQ ID NO:6)

COMPOSITIONS AND METHODS RELATED TO MODIFICATION AND DETECTION OF PSEUDOURIDINE AND 5-HYDROXYMETHYLCYTOSINE

CROSS-REFERENCE TO RELATED APPLICATIONS

This application is a national phase application under 35 U.S.C. § 371 of International Application No. PCT/US2022/071947, filed Apr. 27, 2022, which claims the benefit of priority of U.S. Provisional Patent Application No. 63/180,304 filed Apr. 27, 2021, both of which are hereby incorporated by reference in their entirety.

STATEMENT OF GOVERNMENT SUPPORT

This invention was made with government support under grant number HG008935 awarded by the National Institutes of Health. The government has certain rights in the invention.

SEQUENCE LISTING

The instant application contains a Sequence Listing which has been submitted in ASCII format and is hereby incorporated by reference in its entirety. Said ASCII copy, created on Oct. 20, 2023, is named ARCDP0726US_ST25.txt and is 3,685 bytes in size.

BACKGROUND

I. Field of the Invention

Aspects of this invention relate to at least the field of molecular biology. More particularly, aspects concern methods for modifying, detecting, mapping, and/or evaluating pseudouridine and/or 5-hydroxymethylcytosine within a nucleic acid molecule.

II. Background

With a pseudouridine/uracil (Ψ/U) ratio of approximately 0.2 as measured in human cell lines using LC-MS/MS[2], pseudouridine (Ψ) is the second most abundant internal modification in mammalian mRNA. Thirteen pseudouridine synthase (PUS) enzymes in the human genome have been annotated[3-5], and mutations in some PUS enzymes can lead to a wide range of human diseases including the X-linked dyskeratosis congenita and neurodegenerative conditions such as Alzheimer's Parkinson's[6-8]. While tRNA and rRNA are main targets of pseudouridination, some PUS enzymes can also bind and pseudouridinate mRNA[9]. The installed Ψ modifications were thought to impact translation, mRNA localization, innate immune response, and possibly recoding[10-14].

Currently there is no available antibody for Ψ. Previous detection of Ψ relied on its reaction with N-cyclohexyl-N'-β-(4-methyl-morpholinium) ethylcarbodiimide (CMC) to generate CMC-modified Ψ, which could cause RT stop signatures at highly modified Ψ sites[15]. This approach has been employed to map Ψ transcriptome-wide and identified 392 (W-seq) and 98 (Pseudo-seq) Ψ sites in the human mRNA[16,17], respectively, but showing only 13 overlapped sites between these 2 datasets due to low sensitivity and high false positive RT stops. Later on, an azide-modified CMC was used to enrich Ψ-containing RNA fragments for sequencing (CeU-Seq)[2], allowing more Ψ sites identified; however, the method lacks stoichiometry at the modified sites and the azide-modified CMC is not stable for storage.

5hmC-modified loci can serve as informative biomarkers for a variety of human cancers and other complex diseases. However, existing methods for 5hmC analysis suffer from various limitations, including high expense, low sensitivity, high background, and presence of false positives.

There exists a need for methods and compositions for comprehensive and quantitative modification and detection of pseudouridine and 5-hydroxymethylcytosine.

SUMMARY OF THE INVENTION

The present disclosure addresses certain needs by providing methods, compositions, and kits for modification and detection of pseudouridine and 5-hydroxymethylcytosine. Aspects of the disclosure are directed to methods for modifying and detecting a pseudouridine or 5-hydroxymethylcytosine comprising treatment with bisulfite at a pH between about 6.5 and about 8.0. As described in embodiments of the disclosure, treatment of nucleic acid molecules with bisulfite at a pH between about 6.5 and about 8.0 (e.g., 7.0) is sufficient for modification of a pseudouridine or 5-hydroxymethylcytosine without inducing deamination of unmodified cytosines as seen with conventional bisulfite treatment (e.g., pH<6.0). Methods may further comprise reverse transcription and/or sequencing for detection and quantification of pseudouridine and/or 5-hydroxymethylcytosine.

Embodiments of the disclosure include methods for modifying a pseudouridine, methods for detecting a pseudouridine, methods for quantifying pseudouridine, methods for modifying a 5-hydroxymethylcytosine, methods for detecting a 5-hydroxymethylcytosine, methods for quantifying 5-hydroxymethylcytosine, methods for processing a nucleic acid sample, methods for isolating nucleic acid molecules containing 5-hydroxymethylcytosine, methods for pseudouridine mapping, methods for 5-hydroxymethylcytosine mapping, methods of bisulfite treatment, methods for RNA processing, methods for DNA processing, and kits.

Methods of the present disclosure may include 1, 2, 3, 4, or more of the following steps: incubating an RNA molecule with bisulfite at a pH of between about 6.5 and about 8.0, incubating an RNA molecule with bisulfite at a pH of between 6.5 and 8.0, incubating a DNA molecule with bisulfite at a pH of between about 6.5 and about 8.0, incubating a DNA molecule with bisulfite at a pH of between 6.5 and 8.0, performing a reverse transcription reaction, performing an amplification reaction, detecting cytosine-5-methylenesulfonate (CMS) in an RNA molecule, detecting CMS in a DNA molecule, contacting a nucleic acid molecule with an anti-CMS antibody, generating a mixture comprising an RNA molecule and bisulfite, incubating a mixture under conditions sufficient to generate a modified pseudouridine, generating a mixture comprising a DNA molecule and bisulfite, incubating a mixture under conditions sufficient to generate a modified 5-hydroxymethylcytosine, identifying the location of one or more pseudouridines, identifying the location of one or more 5-hydroxymethylcytosines, isolating an RNA molecule comprising a modified pseudouridine, isolating an RNA molecule comprising a modified 5-hydroxymethylcytosine, isolating a DNA molecule comprising a modified 5-hydroxymethylcytosine, sequencing a nucleic acid molecule, and analyzing a nucleic acid sequence comprising a deletion corresponding to a pseudouridine. Any one or more of the preceding steps may be excluded from certain embodiments of the disclosure.

Kits of the present disclosure may include 1, 2, 3, 4, or more of the following components: a solution comprising a bisulfite salt, a reverse transcriptase enzyme, a polynucleotide kinase enzyme, buffers, reagents, and instructions for use including instructions for incubating a nucleic acid molecule with a bisulfite solution. In some embodiments, a kit of the disclosure includes a bisulfite solution (i.e., a solution comprising a bisulfite salt), where the solution has a pH of between about 6.5 and about 8.0. In some embodiments, a kid includes a bisulfite solution, where the solution has a pH of about 7.0. Any one or more of the preceding components may be excluded from embodiments of the disclosure.

Disclosed herein, in some embodiments, is method for modifying a pseudouridine comprising incubating a ribonucleic acid (RNA) molecule comprising the pseudouridine with bisulfite at a pH of between about 6.5 and about 8.0 to generate a modified RNA molecule comprising a modified pseudouridine. In some embodiments, the method further comprises subjecting the modified RNA molecule to reverse transcription using a reverse transcriptase enzyme to generate a deoxyribonucleic acid (DNA) molecule. In some embodiments, the method further comprises sequencing the DNA molecule. In some embodiments, the method further comprises determining the location of the pseudouridine in the RNA molecule based on the location of the deletion in the sequence of the DNA molecule. In some embodiments, incubating the RNA molecule is performed for about 4 hours.

Also disclosed herein is a method for modifying a 5-hydroxymethylcytosine comprising incubating a ribonucleic acid (RNA) molecule comprising the 5-hydroxymethylcytosine with bisulfite at pH of between about 6.5 and about 8.0 to generate a modified RNA molecule comprising cytosine-5-methylenesulfonate (CMS). In some embodiments, the method further comprises detecting the CMS in the modified RNA molecule. In some embodiments, detecting the CMS comprises contacting the modified RNA molecule with an anti-CMS antibody. In some embodiments, the method further comprises subjecting the modified RNA molecule to reverse transcription using a reverse transcriptase enzyme to generate a deoxyribonucleic acid (DNA) molecule. In some embodiments, the reverse transcriptase enzyme is SuperScript IV. In some embodiments, the method further comprises sequencing the DNA molecule. In some embodiments, incubating the RNA molecule is performed for about 1 hour.

In some embodiments, incubating the RNA molecule is performed at a temperature of between about 65° C. and about 75° C. In some embodiments, incubating the RNA molecule is performed at a temperature of about or at least 65, 66, 67, 68, 69, 70, 71, 72, 73, 74, or 75° C., or any range or value derivable therein. In some embodiments, incubating the RNA molecule is performed at a temperature of at least 95° C. In some embodiments, incubating the RNA molecule is performed at a temperature of about or exactly 95, 96, 97, 98, or 99° C. In some embodiments, incubating the RNA molecule is performed for between 1 hour and 6 hours. In some embodiments, incubating the RNA molecule is performed for about 1, 2, 3, 4, 5, or 6 hours, or any range or value derivable therein. In some embodiments, incubating the RNA molecule is performed for about 4 hours. In some embodiments, incubating the RNA molecule is performed for at most 30 minutes. In some embodiments, incubating the RNA molecule is performed for about or exactly 30, 25, 20, 15, 10, or 5 minutes, or any range or value derivable therein. In some embodiments, incubating the RNA molecule with the bisulfite does not comprise adding hydroquinone. In some embodiments, the RNA molecule is an mRNA molecule, a tRNA molecule, an rRNA molecule, an snRNA molecule, an miRNA molecule, or an lncRNA molecule. In some embodiments, the RNA molecule is from a cfRNA sample. In some embodiments, the RNA molecule is an RNA molecule of a plurality of RNA molecules, wherein the method further comprises quantifying the number of pseudouridines in the plurality of RNA molecules.

Also disclosed herein, in some embodiments, is a method for modifying a 5-hydroxymethylcytosine comprising incubating a deoxyribonucleic acid (DNA) molecule comprising the 5-hydroxymethylcytosine with bisulfite at a pH of between about 6.5 and about 8.0 to generate a nucleic acid molecule comprising cytosine-5-methylenesulfonate (CMS). In some embodiments, incubating the DNA molecule is performed at a temperature of between about 65° C. and about 75° C. In some embodiments, incubating the DNA molecule is performed at a temperature of about 65, 66, 67, 68, 69, 70, 71, 72, 73, 74, or 75° C., or any range or value derivable therein. In some embodiments, incubating the DNA molecule is performed at a temperature of about 70° C. In some embodiments, incubating the DNA molecule is performed at a temperature of at least 95° C. In some embodiments, incubating the DNA molecule is performed at a temperature of about or exactly 95, 96, 97, 98, or 99° C. In some embodiments, incubating the DNA molecule is performed for between 1 hour and 4 hours. In some embodiments, incubating the DNA molecule is performed for about 1, 2, 3, 4, 5, or 6 hours, or any range or value derivable therein. In some embodiments, incubating the DNA molecule is performed for at most 30 minutes. In some embodiments, incubating the DNA molecule is performed for about or exactly 30, 25, 20, 15, 10, or 5 minutes, or any range or value derivable therein. In some embodiments, incubating the DNA molecule with the bisulfite does not comprise adding hydroquinone. In some embodiments, the DNA molecule is genomic DNA. In some embodiments, the DNA molecule is from a cfDNA sample. In some embodiments, the method further comprises detecting the CMS in the modified DNA molecule. In some embodiments, detecting the DNA comprises contacting the modified DNA molecule with an anti-CMS antibody. In some embodiments, the method further comprises sequencing the modified DNA molecule.

In some embodiments, the nucleic acid molecule (e.g., DNA or RNA molecule) is incubated with the bisulfite at a pH of or of about 6.5, 6.6, 6.7, 6.81, 6.82, 6.83, 6.84, 6.85, 6.86, 6.87, 6.88, 6.89, 6.9, 6.91, 6.92, 6.93, 6.94, 6.95, 6.96, 6.97, 6.98, 6.99, 7.0, 7.01, 7.02, 7.03, 7.04, 7.05, 7.06, 7.07, 7.08, 7.09, 7.1, 7.2, 7.3, 7.4, 7.5, 7.6, 7.7, 7.8, 7.9, or 8.0, or any range or value derivable therein. In some embodiments, the pH is about 7.0. In some embodiments, the bisulfite is at least or about 10, 11, 12, 13, 14, 15, 16, 17, 18, 19, 20, 21, 22, 23, 24, 25, 26, or 27% sodium bisulfite by weight (w/w), or any range or value derivable therein. In some embodiments, the bisulfite is at least 10% sodium bisulfite by weight. In some embodiments, the bisulfite is at least 20% sodium bisulfite by weight. In some embodiments, the bisulfite is at least 25% sodium bisulfite by weight. In some embodiments, the bisulfite is at least or about 10, 11, 12, 13, 14, 15, 16, 17, 18, 19, 20, 21, 22, 23, 24, 25, 26, or 27% ammonium bisulfite by weight (w/w), or any range or value derivable therein. In some embodiments, the bisulfite is at least 10% ammonium bisulfite by weight. In some embodiments, the bisulfite is at least 20% ammonium bisulfite by weight. In some embodiments, the bisulfite is at least 25% ammonium bisulfite by weight.

Further disclosed herein, in some embodiments, is a method for modifying a plurality of pseudouridines in a sample, the method comprising (a) generating a mixture having a pH of between about 6.5 and about 8.0 comprising (i) a plurality of RNA molecules comprising the plurality of pseudouridines and (ii) bisulfite; and (b) incubating the mixture under conditions sufficient to generate a plurality of modified RNA molecules comprising a plurality of modified pseudouridines. In some embodiments, incubating the mixture is performed at a temperature of between 65° C. and 75° C. In some embodiments, incubating the mixture is performed at a temperature of about 65, 66, 67, 68, 69, 70, 71, 72, 73, 74, or 75° C., or any range or value derivable therein. In some embodiments, incubating the mixture is performed at a temperature of about 70° C. In some embodiments, the mixture has a pH of or of about 6.5, 6.6, 6.7, 6.8, 6.9, 7.0, 7.1, 7.2, 7.3, 7.4, 7.5, 7.6, 7.7, 7.8, 7.9, or 8.0, or any range or value derivable therein. In some embodiments, the mixture has a pH of between about 6.9 and about 7.1. In some embodiments, the mixture has a pH of about 7.0. In some embodiments, incubating the mixture is performed for between 1 hour and 6 hours. In some embodiments, incubating the mixture is performed for about 1, 2, 3, 4, 5, or 6 hours, or any range or value derivable therein. In some embodiments, incubating the mixture is performed for about 4 hours. In some embodiments, the mixture does not comprise hydroquinone. In some embodiments, the bisulfite is at least 10% sodium bisulfite by weight. In some embodiments, the bisulfite is at least 20% sodium bisulfite by weight. In some embodiments, the bisulfite is at least 25% sodium bisulfite by weight. In some embodiments, the plurality of RNA molecules are derived from a biological sample. In some embodiments, the plurality of RNA molecules comprise mRNA molecules, tRNA molecules, rRNA molecules, snRNA molecules, miRNA molecules, lncRNA molecules, or a combination thereof. In some embodiments, the method further comprises (c) subjecting the plurality of modified RNA molecules to a reverse transcription reaction using a reverse transcriptase enzyme to generate a plurality of DNA molecules. In some embodiments, the reverse transcriptase enzyme is SuperScript IV. In some embodiments, the method further comprises sequencing the plurality of DNA molecules. In some embodiments, the method further comprises quantifying the number of pseudouridines in the plurality of RNA molecules. In some embodiments, the method further comprises identifying the location of each pseudouridine of the plurality of pseudouridines on each RNA molecule of the plurality of RNA molecules by identifying the location of the deletion in the plurality of DNA molecules.

Also disclosed herein, in some embodiments, is a kit for modifying a pseudouridine or a 5-hydroxymethylcytosine comprising (a) a solution having a pH between about 6.5 and about 8.0 comprising a bisulfite salt; and (b) instructions for incubating a nucleic acid molecule with the solution. In some embodiments, the solution has a pH of between about 6.9 and about 7.1. In some embodiments, the solution has a pH of about 7.0. In some embodiments, the solution consists essentially of the bisulfite salt. In some embodiments, the solution is a bisulfite solution at a concentration of at least 5 M. In some embodiments, the solution is a bisulfite at least or about 10, 11, 12, 13, 14, 15, 16, 17, 18, 19, 20, 21, 22, 23, 24, 25, 26, or 27% sodium bisulfite by weight (w/w), or any range or value derivable therein. In some embodiments, the bisulfite is at least 10% sodium bisulfite by weight. In some embodiments, the bisulfite is at least 20% sodium bisulfite by weight. In some embodiments, the bisulfite is at least 25% sodium bisulfite by weight. In some embodiments, the bisulfite is at least or about 10, 11, 12, 13, 14, 15, 16, 17, 18, 19, 20, 21, 22, 23, 24, 25, 26, or 27% ammonium bisulfite by weight (w/w), or any range or value derivable therein. In some embodiments, the bisulfite is at least 10% ammonium bisulfite by weight. In some embodiments, the bisulfite is at least 20% ammonium bisulfite by weight. In some embodiments, the bisulfite is at least 25% ammonium bisulfite by weight. In some embodiments, the kit further comprises one or more buffers. In some embodiments, the kit further comprises a reverse transcriptase enzyme. In some embodiments, the reverse transcriptase enzyme is SuperScript IV. In some embodiments, the kit further comprises a polynucleotide kinase enzyme. In some embodiments, the polynucleotide kinase enzyme is T4 polynucleotide kinase. In some embodiments, the instructions comprise instructions for incubating the nucleic acid molecule at a temperature of between about 65° C. and about 75° C. In some embodiments, the instructions comprise instructions for incubating the nucleic acid molecule at a temperature of about 65, 66, 67, 68, 69, 70, 71, 72, 73, 74, or 75° C., or any range or value derivable therein. In some embodiments, the instructions comprise instructions for incubating the nucleic acid molecule at a temperature of about 70° C. In some embodiments, the instructions comprise instructions for incubating the nucleic acid molecule for between 1 hour and 6 hours. In some embodiments, the instructions comprise instructions for incubating the nucleic acid molecule for about 1, 2, 3, 4, 5, or 6 hours, or more. In some embodiments, the instructions comprise instructions for incubating the nucleic acid molecule for 4 hours. In some embodiments, the instructions comprise instructions for incubating the nucleic acid molecule for at most 30 minutes. In some embodiments, the instructions comprise instructions for incubating the nucleic acid molecule for at most, about, or exactly 30, 25, 20, 15, 10, or 5 minutes, or any range or value derivable therein.

In some embodiments, the nucleic acid molecule is an RNA molecule comprising a pseudouridine. In some embodiments, the kit further comprises a control RNA molecule comprising a pseudouridine. In some embodiments, the nucleic acid molecule is an RNA molecule comprising a 5-hydroxymethylcytosine. In some embodiments, the kit further comprises a control RNA molecule comprising a 5-hydroxymethylcytosine. In some embodiments, the nucleic acid molecule is a DNA molecule comprising a 5-hydroxymethylcytosine. In some embodiments, the kit further comprises a control DNA molecule comprising a 5-hydroxymethylcytosine.

Throughout this application, the term "about" is used to indicate that a value includes the inherent variation of error for the measurement or quantitation method.

The use of the word "a" or "an" when used in conjunction with the term "comprising" may mean "one," but it is also consistent with the meaning of "one or more," "at least one," and "one or more than one."

The phrase "and/or" means "and" or "or". To illustrate, A, B, and/or C includes: A alone, B alone, C alone, a combination of A and B, a combination of A and C, a combination of B and C, or a combination of A, B, and C. In other words, "and/or" operates as an inclusive or. It is specifically contemplated that A, B, or C may be specifically excluded from an embodiment.

The words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The compositions and methods for their use can "comprise," "consist essentially of," or "consist of" any of the ingredients or steps disclosed throughout the specification. Compositions and methods "consisting essentially of" any of the ingredients or steps disclosed limits the scope of the claim to the specified materials or steps which do not materially affect the basic and novel characteristic of the claimed invention.

It is specifically contemplated that any limitation discussed with respect to one embodiment of the invention may apply to any other embodiment of the invention. Furthermore, any composition of the invention may be used in any method of the invention, and any method of the invention may be used to produce or to utilize any composition of the invention. Aspects of an embodiment set forth in the Examples are also embodiments that may be implemented in the context of embodiments discussed elsewhere in a different Example or elsewhere in the application, such as in the Summary, Detailed Description, Claims, and Brief Description of the Drawings.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 6A shows results demonstrating that the majority of deletion sites were derived from Ψ. FIG. 6B shows the overlap of detected Ψ sites between the two replicates. FIG. 6C shows a comparison of detected Ψ sites between the BID-seq protocol as described in Example 1 and the RBS-seq protocol of Khoddami, et al., 2019. FIG. 6D shows results demonstrating that Ψ sites in mRNA are mainly distributed in coding regions (CDS) and 3' UTRs. FIG. 6E shows the metagene of Ψ distribution in HeLa cell mRNA. FIG. 6F shows the distribution pattern of the highly modified Ψ sites with fraction >15%.

FIG. 7A shows the 2-D plot for deletion ratios from BID-seq treated library. FIG. 7B shows an example IGV plot of the highly modified Ψ site at position 1081 of HeLa 18S ribosomal RNA, within a CAΨAA motif FIG. 7C shows the 2-D plot for deletion ratios of known Ψ sites in HeLa18S and 28S ribosomal RNA in BID-seq or RBS-seq treated samples.

FIG. 10A—BID-seq reveals 506, 463 and 808 1 sites (modification fraction above 10%) in HeLa, HEK293T and A549 cells, respectively. FIG. 10B—Pie chart showing the distribution of mRNA Ψ sites in HeLa, HEK293T and A549 cells, with stoichiometry ≥10% in three mRNA segments. FIG. 10C—The modification level distribution of Ψ sites in mRNA from HeLa, HEK293T and A549 cells, with the definition of highly modified Ψ sites as the ones above 50% Ψ-fraction (marked by green line). FIG. 10D—Distribution of motifs for 506 Ψ sites in HeLa mRNA, with "X axis" as the motif frequency and "Y axis" showing the average Ψ modification fraction of each motif. FIG. 10E—Top 20 enriched GO clusters from Ψ-modified genes carrying mRNA Ψ, in HeLa.

FIG. 14A shows gel electrophoresis of the DNA obtained from the samples treated as indicated. FIG. 14B shows qPCR results from DNA obtained from the samples treated as indicated.

FIG. 16A shows qPCR of 10 ng of mESC DNA after anti-5hmC antibody pulldown. FIG. 16B shows qPCR of 10 ng of mESC DNA after BS treatment and anti-CMS antibody pulldown. FIG. 16C shows that binding affinity of CMS and the antibody is very high, and changing the concentration of salt in the wash buffer only has a minimal effect.

DETAILED DESCRIPTION OF THE INVENTION

Figure 1:
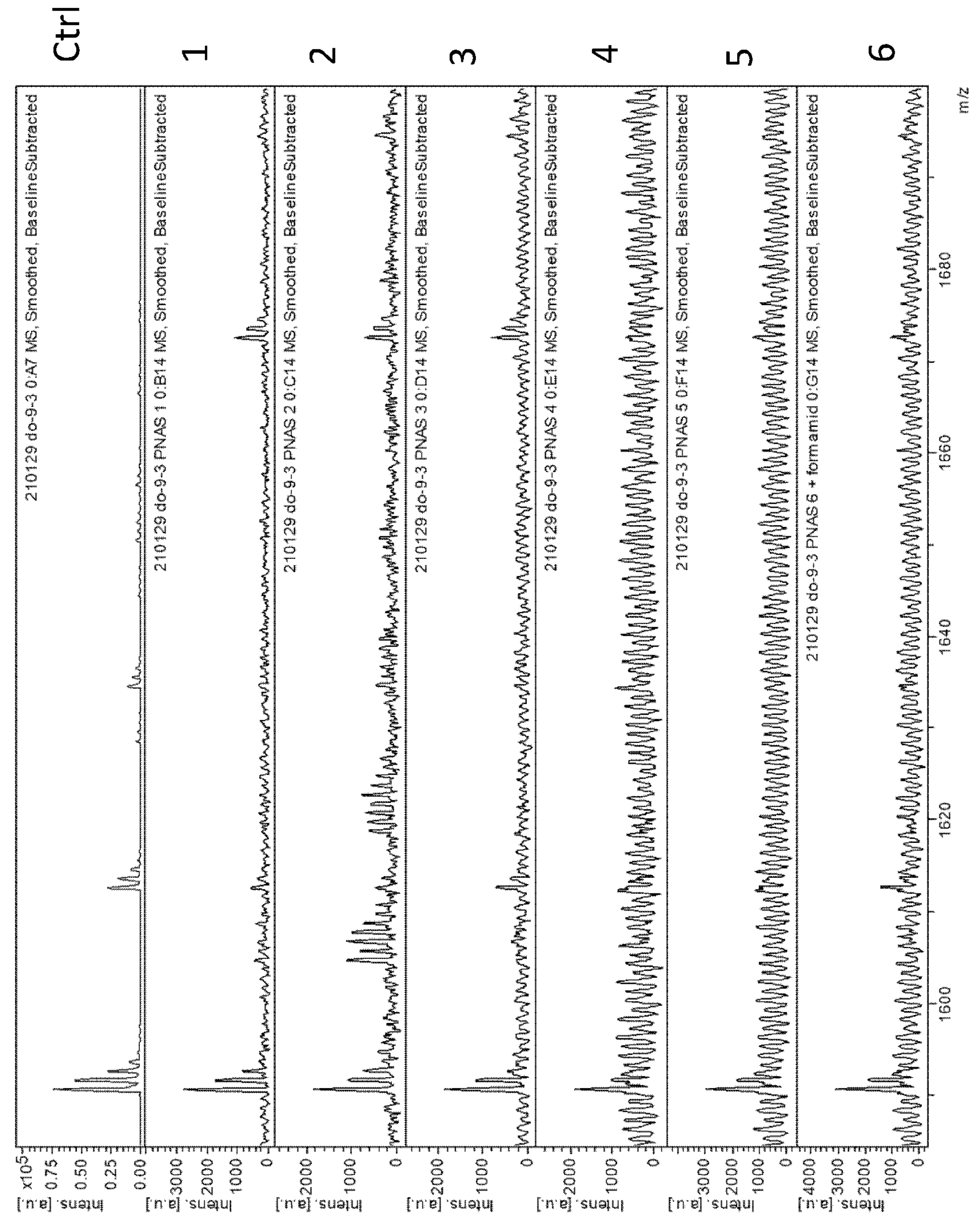
FIG. 1 shows MALDI-TOF mass spectrometry results of AGΨGA (SEQ ID NO:4) reactions with bisulfite under RBS conditions. Among six replicates, Ψ was converted to Ψ-BS adduct in varying, but less than 30%, efficiency.

Recently, a modified bisulfite treatment was reported to lead to modest base deletions at some Ψ sites in RNA when mapping $m^5C$ in RNA[1], although only 15 Ψ sites (deletion rate >5%) in human rRNA was revealed and the signals on mRNA are weak with only 72 sites showing deletion rate >5%. This method, called RBS-seq, inevitably converted all cytidines into uridines under acidic bisulfite treatment conditions, making a portion of reads difficult to be aligned to mRNA. However, the discovery of Ψ-BS adduct and induced deletion caused by this adduct in the subsequent reverse transcription (RT) process[1] provided a new possibility for Ψ detection. As disclosed herein, careful examination of Ψ reactivity with bisulfite led to the development of a reaction that leads to quantitative Ψ-BS formation and no C-to-U conversion. Subsequent RT and sequencing led to quantitative pseudouridine sequencing at base resolution with modification stoichiometry information. Such methods are also effective in modification and detection of 5-hydroxymethylcytosine in RNA and DNA.

Disclosed are methods and compositions for modification, detection, and quantification of Ψ and 5-hydroxymethylcytosine. Aspects of the disclosure are based, at least in part, on the surprising discovery that treatment of RNA or DNA with bisulfite under non-standard conditions, including non-standard pH (e.g., pH 6.8-7.2), modifies Ψ and 5-hydroxymethylcytosine without converting cytidines into uridines.

I. Modification and Detection of Pseudouridine and 5-Hydroxymethylcytosine

Aspects of the present disclosure are directed to methods for modification of pseudouridine. In some embodiments, such methods comprise incubating a pseudouridine, an RNA molecule comprising a pseudouridine, and/or a population of RNA molecules comprising pseudouridines with bisulfite under conditions sufficient to modify the pseudouridine. As used herein, a "modified pseudouridine" describes a pseudouridine that has been chemically modified, e.g., by addition or removal of a chemical moiety. In some embodiments, a modified pseudouridine is generated by addition of a chemical moiety to a pseudouridine. In some embodiments, a modified pseudouridine is generated by treatment with N-cyclohexyl-N'-(2-morpholinoethyl)-carbodiimide-metho-p-toluenesulfonate (CMC), wherein the modified pseudouridine is $N_3$-CMC-Ψ. In some embodiments, a modified pseudouridine is generated by treatment with a bisulfite salt (e.g., sodium bisulfite), wherein the modified pseudouridine comprises a sulfonate (—$SO_3$) moiety.

Further aspects of the disclosure are directed to methods for detection and/or quantification of pseudouridine in RNA. Such methods may include, for example, determining the position of a pseudouridine in an RNA molecule and quantifying the amount of pseudouridines in a population of RNA molecules. Various types of RNA molecules are known in the art and contemplated herein including, for example, mRNA, tRNA, rRNA, snRNA, miRNA, siRNA, and lncRNA. In some embodiments, the disclosed methods comprise generating a modified pseudouridine in an RNA molecule, followed by subjecting the RNA molecule to reverse transcription. As disclosed herein, reverse transcription of an RNA molecule comprising a modified pseudouridine (e.g., a sulfonated pseudouridine) may result in a deletion in the resulting DNA molecule. The deletion may be a one nucleotide deletion, where the one nucleotide corresponds to the pseudouridine in the original RNA molecule. The deletion may be a deletion of two or more nucleotides, where the deletion corresponds to the pseudouridine in the original RNA molecule plus one or more nucleotides adjacent to the pseudouridine.

Further aspects of the present disclosure are directed to methods for modification of 5-hydroxymethylcytosine. In some embodiments, such methods comprise incubating a 5-hydroxymethylcytosine, a nucleic acid molecule comprising a 5-hydroxymethylcytosine, and/or a population of nucleic acid molecules comprising 5-hydroxymethylcytosines with bisulfite under conditions sufficient to modify the 5-hydroxymethylcytosine. As used herein, a "modified 5-hydroxymethylcytosine" describes a 5-hydroxymethylcytosine that has been chemically modified, e.g., by addition or removal of a chemical moiety. In some embodiments, a modified 5-hydroxymethylcytosine is generated by treatment with a bisulfite salt (e.g., sodium bisulfite). In some embodiments, the modified 5-hydroxymethylcytosine is cytosine-5-methylenesulfonate (CMS).

Further aspects of the disclosure are directed to methods for detection and/or quantification of 5-hydroxymethylcytosine in RNA and/or DNA molecules. Such methods may include, for example, determining the position of a 5-hydroxymethylcytosine in an RNA or DNA molecule and quantifying the amount of 5-hydroxymethylcytosines in a population of RNA molecules or DNA molecules. In some embodiments, the disclosed methods comprise generating a modified 5-hydroxymethylcytosine (e.g., CMS) in a DNA or RNA molecule, followed by treatment with an antibody or antigen fragment thereof specific for CMS (e.g., as described in US Patent Application Publication No. 2018/0119225, incorporated herein by reference). Such an antibody may be used to isolate the CMS-containing RNA or DNA molecules, followed by sequencing to identify the location of the 5-hydroxymethylcytosine.

In particular embodiments, methods of the disclosure comprise incubation of a nucleic acid molecule (e.g., an RNA molecule comprising pseudouridine, an RNA molecule comprising 5-hydroxymethylcytosine, or a DNA molecule comprising 5-hydroxymethylcytosine) under conditions sufficient for generation of a modified pseudouridine or modified 5-hydroxymethylcytosine, but insufficient for deamination of cytosine. Such conditions are described in further detail below and elsewhere herein. For example, as disclosed herein, incubation of a nucleic acid molecule at a pH between 6.5 and 8.0 may be sufficient to modify a pseudouridine in the nucleic acid molecule to generate a sulfonated pseudouridine but insufficient to deaminate any cytosines in the nucleic acid molecule.

In some embodiments, the disclosed methods comprise incubating a nucleic acid molecule with bisulfite at a pH between 6.5 and 8.0. In some embodiments, the nucleic acid molecule is incubated with bisulfite at a pH of about, at least about, or at most about 6.5, 6.6, 6.7, 6.81, 6.82, 6.83, 6.84, 6.85, 6.86, 6.87, 6.88, 6.89, 6.9, 6.91, 6.92, 6.93, 6.94, 6.95, 6.96, 6.97, 6.98, 6.99, 7.0, 7.01, 7.02, 7.03, 7.04, 7.05, 7.06, 7.07, 7.08, 7.09, 7.1, 7.2, 7.3, 7.4, 7.5, 7.6, 7.7, 7.8, 7.9, or 8.0, or any range or value derivable therein. In some embodiments, the nucleic acid molecule is incubated with bisulfite at a pH of 6.5, 6.6, 6.7, 6.81, 6.82, 6.83, 6.84, 6.85, 6.86, 6.87, 6.88, 6.89, 6.9, 6.91, 6.92, 6.93, 6.94, 6.95, 6.96, 6.97, 6.98, 6.99, 7.0, 7.01, 7.02, 7.03, 7.04, 7.05, 7.06, 7.07, 7.08, 7.09, 7.1, 7.2, 7.3, 7.4, 7.5, 7.6, 7.7, 7.8, 7.9, or 8.0, or any range or value derivable therein. In some embodiments, the nucleic acid molecule is incubated with bisulfite at a pH of about 7.0. In some embodiments, the nucleic acid molecule is incubated with bisulfite at a pH of 7.0. In some embodiments, the nucleic acid molecule is incubated with bisulfite at a pH of about 6.95. In some embodiments, the nucleic acid molecule is incubated with bisulfite at a pH of 6.95. In some embodiments, the nucleic acid molecule is incubated with bisulfite at a pH of about 7.05. In some embodiments, the nucleic acid molecule is incubated with bisulfite at a pH of 7.05.

In some embodiments, the disclosed methods comprise incubating a nucleic acid molecule with bisulfite for, for at most, or for at least 12, 11, 10, 9, 8, 7, 6, 5, or 4 hours, or any range or value derivable therein. In some embodiments, the nucleic acid molecule is incubated with bisulfite for about 4 hours. In some embodiments, the disclosed methods comprise incubating a nucleic acid molecule with bisulfite for or for at most 30, 25, 20, 15, 10, or 5 minutes, or any range or value derivable therein.

In some embodiments, the disclosed methods comprise incubating a nucleic acid molecule with bisulfite at a temperature of about, at least about, or at most about 60, 61, 62, 63, 64, 65, 66, 67, 68, 69, 70, 71, 72, 73, 74, 75, 76, 77, 78, 79, or 80° C., or any range or value derivable therein. In some embodiments, the nucleic acid molecule is incubated at a temperature between about 65° C. and about 75° C. In some embodiments, the nucleic acid molecule is incubated at a temperature of about 65, 66, 67, 68, 69, 70, 71, 72, 73, 74, or 75° C., or any range or value derivable therein. In some embodiments, the nucleic acid molecule is incubated at a temperature of about 70° C. In some embodiments, the nucleic acid molecule is incubated at a temperature of 70° C.

In some embodiments, the disclosed methods comprise incubating a nucleic acid molecule with bisulfite at a temperature of about or at least about 90, 91, 92, 93, 94, 95, 96, 97, 98, 99, or 99.5° C., or any range or value derivable therein. In some embodiments, the nucleic acid molecule is incubated at a temperature of at least 95° C. In some embodiments, the nucleic acid molecule is incubated at a temperature of about 95, 96, 97, 98, 99° C., or any range or value derivable therein. In some embodiments, the nucleic acid molecule is incubated at a temperature of about 95° C. In some embodiments, the nucleic acid molecule is incubated at a temperature of 95° C.

In some embodiments, the disclosed methods comprise bisulfite solutions having a at least 10% sodium bisulfite by weight. In some embodiments, a bisulfite solution of the present disclosure has at least or about 10, 11, 12, 13, 14, 15, 16, 17, 18, 19, 20, 21, 22, 23, 24, 25, 25.1, 25.2, 25.3, 25.4, 25.5, 25.6, 25.7, 25.8, 25.9, 26, 26.1, 26.2, 26.3, 26.4, 26.5, 26.6, 26.7, 26.8, 26.9, or 27% bisulfite salt (e.g., sodium bisulfite, ammonium bisulfite) by weight (w/w), or any range or value derivable therein. In some embodiments, a bisulfite solution has at least 10% sodium bisulfite by weight. In some embodiments, a bisulfite solution has at least 20% sodium bisulfite by weight. In some embodiments, a bisulfite solution has at least 25% sodium bisulfite by weight. In some embodiments, a bisulfite solution has about 26.4% sodium bisulfite by weight. In some embodiments, a bisulfite solution has at least 10% ammonium bisulfite by weight. In some embodiments, a bisulfite solution has at least 20% ammonium bisulfite by weight. In some embodiments, a bisulfite solution has at least 25% ammonium bisulfite by weight. In some embodiments, a bisulfite solution has about 26.4% ammonium bisulfite by weight. As understood by the skilled artisan, a bisulfite solution of the present disclosure may be described in terms of molarity (M), percent by weight (also "weight percent"; w/w), or any other units. When described in terms of one unit (e.g., w/w) equivalent solutions expressed by other units (e.g., M) are also contemplated herein.

II. Sample Preparation

In certain aspects, methods involve obtaining a sample (also "biological sample") from a subject. The methods of obtaining provided herein may include methods of biopsy such as fine needle aspiration, core needle biopsy, vacuum assisted biopsy, incisional biopsy, excisional biopsy, punch biopsy, shave biopsy or skin biopsy. In certain embodiments the sample is obtained from a biopsy from esophageal tissue by any of the biopsy methods previously mentioned. In other embodiments the sample may be obtained from any of the tissues provided herein that include but are not limited to non-cancerous or cancerous tissue and non-cancerous or cancerous tissue from the serum, gall bladder, mucosal, skin, heart, lung, breast, pancreas, blood, liver, muscle, kidney, smooth muscle, bladder, colon, intestine, brain, prostate, esophagus, or thyroid tissue. Alternatively, the sample may be obtained from any other source including but not limited to blood, sweat, hair follicle, buccal tissue, tears, menses, feces, or saliva. In certain aspects of the current methods, any medical professional such as a doctor, nurse or medical technician may obtain a biological sample for testing. Yet further, the biological sample can be obtained without the assistance of a medical professional.

A sample may include but is not limited to, tissue, cells, or biological material from cells or derived from cells of a subject. The biological sample may be a heterogeneous or homogeneous population of cells or tissues. The biological sample may be a cell-free sample (e.g., serum, plasma). The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

The sample may be a sample comprising cell-free nucleic acid. Cell-free nucleic acid includes, for example, cell-free DNA (cfDNA) and cell-free RNA (cfRNA). Cell-free nucleic acid may be isolated, extracted, or otherwise purified from a biological sample for further analysis or processing using the methods and compositions disclosed herein. In some aspects, a sample comprises at least, at most, or about 1000, 900, 800, 700, 600, 500, 400, 300, 200, 100, 50, 40, 30, 20, 10, 5, 4, or 3 ng of nucleic acid, or any range or value derivable therein. In some aspects, a sample comprises at most 50 ng of DNA (e.g., cfDNA). In some aspects, a sample comprises at most 50 ng of RNA (e.g., cfRNA). As disclosed herein, certain methods of the present disclosure, including methods for modifying a pseudouridine and methods for modifying a 5-hydroxymethylcytosine, are particularly suitable for processing and analysis of samples having low amounts of nucleic acid (e.g., less than 200, 150, 100, 50, 30, 20, or 10 ng of DNA and/or RNA).

The sample may be obtained by methods known in the art. In certain embodiments the samples are obtained by biopsy. In other embodiments the sample is obtained by swabbing, endoscopy, scraping, phlebotomy, or any other methods known in the art. In some cases, the sample may be obtained, stored, or transported using components of a kit of the present methods. In some cases, multiple samples, such as multiple tissue samples may be obtained for diagnosis by the methods described herein. In other cases, multiple samples, such as one or more samples from one tissue type and one or more samples from another specimen may be obtained for diagnosis by the methods. In some cases, multiple samples such as one or more samples from one tissue type and one or more samples from another specimen may be obtained at the same or different times. Samples may be obtained at different times are stored and/or analyzed by different methods. For example, a sample may be obtained and analyzed by routine staining methods or any other cytological analysis methods.

In some embodiments the biological sample may be obtained by a physician, nurse, or other medical professional such as a medical technician, endocrinologist, cytologist, phlebotomist, radiologist, or a pulmonologist. The medical professional may indicate the appropriate test or assay to perform on the sample. In certain aspects a molecular profiling business may consult on which assays or tests are most appropriately indicated. In further aspects of the current methods, the patient or subject may obtain a biological sample for testing without the assistance of a medical professional, such as obtaining a whole blood sample, a urine sample, a fecal sample, a buccal sample, or a saliva sample.

In other cases, the sample is obtained by an invasive procedure including but not limited to: biopsy, needle aspiration, endoscopy, or phlebotomy. The method of needle aspiration may further include fine needle aspiration, core needle biopsy, vacuum assisted biopsy, or large core biopsy. In some embodiments, multiple samples may be obtained by the methods herein to ensure a sufficient amount of biological material.

General methods for obtaining biological samples are also known in the art. Publications such as Ramzy, Ibrahim Clinical Cytopathology and Aspiration Biopsy 2001, which is herein incorporated by reference in its entirety, describes general methods for biopsy and cytological methods. In one embodiment, the sample is a fine needle aspirate of a esophageal or a suspected esophageal tumor or neoplasm. In some cases, the fine needle aspirate sampling procedure may be guided by the use of an ultrasound, X-ray, or other imaging device.

In some embodiments of the present methods, the molecular profiling business may obtain the biological sample from a subject directly, from a medical professional, from a third party, or from a kit provided by a molecular profiling business or a third party. In some cases, the biological sample may be obtained by the molecular profiling business after the subject, a medical professional, or a third party acquires and sends the biological sample to the molecular profiling business. In some cases, the molecular profiling business may provide suitable containers, and excipients for storage and transport of the biological sample to the molecular profiling business.

In some embodiments of the methods described herein, a medical professional need not be involved in the initial diagnosis or sample acquisition. An individual may alternatively obtain a sample through the use of an over the counter (OTC) kit. An OTC kit may contain a means for obtaining said sample as described herein, a means for storing said sample for inspection, and instructions for proper use of the kit. In some cases, molecular profiling services are included in the price for purchase of the kit. In other cases, the molecular profiling services are billed separately. A sample suitable for use by the molecular profiling business may be any material containing tissues, cells, nucleic acids, genes, gene fragments, expression products, gene expression products, or gene expression product fragments of an individual to be tested. Methods for determining sample suitability and/or adequacy are provided.

In some embodiments, the subject may be referred to a specialist such as an oncologist, surgeon, or endocrinologist. The specialist may likewise obtain a biological sample for testing or refer the individual to a testing center or laboratory for submission of the biological sample. In some cases the medical professional may refer the subject to a testing center or laboratory for submission of the biological sample. In other cases, the subject may provide the sample. In some cases, a molecular profiling business may obtain the sample.

II. Assay Methods

A. Detection of Methylated DNA

Aspects of the methods include assaying nucleic acids to determine expression levels and/or methylation levels of nucleic acids. Certain assays for the detection of methylated DNA are known in the art. Exemplary methods are described herein. 1. HPLC-UV The technique of HPLC-UV (high performance liquid chromatography-ultraviolet), developed by Kuo and colleagues in 1980 (described further in Kuo K. C. et al., Nucleic Acids Res. 1980; 8:4763-4776, which is herein incorporated by reference) can be used to quantify the amount of deoxycytidine (dC) and methylated cytosines (5 mC) present in a hydrolysed DNA sample. The method includes hydrolyzing the DNA into its constituent nucleoside bases, the 5 mC and dC bases are separated chromatographically and, then, the fractions are measured. Then, the 5 mC/dC ratio can be calculated for each sample, and this can be compared between the experimental and control samples.

2. LC-MS/MS

Liquid chromatography coupled with tandem mass spectrometry (LC-MS/MS) is an high-sensitivity approach to HPLC-UV, which requires much smaller quantities of the hydrolysed DNA sample. In the case of mammalian DNA, of which ~2%-5% of all cytosine residues are methylated, LC-MS/MS has been validated for detecting levels of methylation levels ranging from 0.05%-10%, and it can confidently detect differences between samples as small as ~0.25% of the total cytosine residues, which corresponds to ~5% differences in global DNA methylation. The procedure routinely requires 50-100 ng of DNA sample, although much smaller amounts (as low as 5 ng) have been successfully profiled. Another major benefit of this method is that it is not adversely affected by poor-quality DNA (e.g., DNA derived from FFPE samples).

3. ELISA-Based Methods

There are several commercially available kits, all enzyme-linked immunosorbent assay (ELISA) based, that enable the quick assessment of DNA methylation status. These assays include Global DNA Methylation ELISA, available from Cell Biolabs; Imprint Methylated DNA Quantification kit (sandwich ELISA), available from Sigma-Aldrich; EpiSeeker methylated DNA Quantification Kit, available from abcam; Global DNA Methylation Assay LINE—1, available from Active Motif, 5-mC DNA ELISA Kit, available from Zymo Research; MethylFlash Methylated DNA5-mC Quantification Kit and MethylFlash Methylated DNA5-mC Quantification Kit, available from Epigentek.

Briefly, the DNA sample is captured on an ELISA plate, and the methylated cytosines are detected through sequential incubations steps with: (1) a primary antibody raised against 5 Mc; (2) a labelled secondary antibody; and then (3) colorimetric/fluorometric detection reagents.

The Global DNA Methylation Assay LINE—1 specifically determines the methylation levels of LINE-1 (long interspersed nuclear elements-1) retrotransposons, of which ~17% of the human genome is composed. These are well established as a surrogate for global DNA methylation. Briefly, fragmented DNA is hybridized to biotinylated LINE-1 probes, which are then subsequently immobilized to a streptavidin-coated plate. Following washing and blocking steps, methylated cytosines are quantified using an anti-5 mC antibody, HIRP-conjugated secondary antibody and chemiluminescent detection reagents. Samples are quantified against a standard curve generated from standards with known LINE-1 methylation levels. The manufacturers claim the assay can detect DNA methylation levels as low as 0.5%. Thus, by analysing a fraction of the genome, it is possible to achieve better accuracy in quantification.

4. LINE-1 Pyrosequencing

Levels of LINE-1 methylation can alternatively be assessed by another method that involves the bisulfite conversion of DNA, followed by the PCR amplification of LINE-1 conservative sequences. The methylation status of the amplified fragments is then quantified by pyrosequencing, which is able to resolve differences between DNA samples as small as ~5%. Even though the technique assesses LINE-1 elements and therefore relatively few CpG sites, this has been shown to reflect global DNA methylation changes very well. The method is particularly well suited for high throughput analysis of cancer samples, where hypomethylation is very often associated with poor prognosis. This method is particularly suitable for human DNA, but there are also versions adapted to rat and mouse genomes.

5. AFLP and RFLP

Detection of fragments that are differentially methylated could be achieved by traditional PCR-based amplification fragment length polymorphism (AFLP), restriction fragment length polymorphism (RFLP) or protocols that employ a combination of both.

6. LUMA

The LUMA (luminometric methylation assay) technique utilizes a combination of two DNA restriction digest reactions performed in parallel and subsequent pyrosequencing reactions to fill-in the protruding ends of the digested DNA strands. One digestion reaction is performed with the CpG methylation-sensitive enzyme HpaII; while the parallel reaction uses the methylation-insensitive enzyme MspI, which will cut at all CCGG sites. The enzyme EcoRI is included in both reactions as an internal control. Both MspI and HpaII generate 5'-CG overhangs after DNA cleavage, whereas EcoRI produces 5'-AATT overhangs, which are then filled in with the subsequent pyrosequencing-based extension assay. Essentially, the measured light signal calculated as the HpaII/MspI ratio is proportional to the amount of unmethylated DNA present in the sample. As the sequence of nucleotides that are added in pyrosequencing reaction is known, the specificity of the method is very high and the variability is low, which is essential for the detection of small changes in global methylation. LUMA requires only a relatively small amount of DNA (250-500 ng), demonstrates little variability and has the benefit of an internal control to account for variability in the amount of DNA input.

7. Bisulfite Sequencing

The bisulfite treatment of DNA under low pH conditions (e.g., pH<6.0) mediates the deamination of cytosine into uracil, and these converted residues will be read as thymine, as determined by PCR-amplification and subsequent Sanger sequencing analysis. However, 5-mC residues are resistant to this conversion and, so, will remain read as cytosine. Thus, comparing the Sanger sequencing read from an untreated DNA sample to the same sample following bisulfite treatment enables the detection of the methylated cytosines. With the advent of next-generation sequencing (NGS) technology, this approach can be extended to DNA methylation analysis across an entire genome. To ensure complete conversion of non-methylated cytosines, controls may be incorporated for bisulfite reactions.

Whole genome bisulfite sequencing (WGBS) is similar to whole genome sequencing, except for the additional step of bisulfite conversion. Sequencing of the 5 mC-enriched fraction of the genome is not only a less expensive approach, but it also allows one to increase the sequencing coverage and, therefore, precision in revealing differentially-methylated regions. Sequencing could be done using any existing NGS platform; Illumina and Life Technologies both offer kits for such analysis.

Bisulfite sequencing methods include reduced representation bisulfite sequencing (RRBS), where only a fraction of the genome is sequenced. In RRBS, enrichment of CpG-rich regions is achieved by isolation of short fragments after MspI digestion that recognizes CCGG sites (and it cut both methylated and unmethylated sites). It ensures isolation of ~85% of CpG islands in the human genome. Then, the same bisulfite conversion and library preparation is performed as for WGBS. The RRBS procedure normally requires ~100 ng-1 μg of DNA.

8. Methods that Exclude Bisulfite Conversion

In some aspects, direct detection of modified bases without bisulfite conversion may be used to detect methylation. Pacific Biosciences company has developed a way to detect methylated bases directly by monitoring the kinetics of polymerase during single molecule sequencing and offers a commercial product for such sequencing (further described in Flusberg B. A., et al., Nat. Methods. 2010; 7:461-465, which is herein incorporated by reference). Other methods include nanopore-based single-molecule real-time sequencing technology (SMRT), which is able to detect modified bases directly (described in Laszlo A. H. et al., Proc. Natl. Acad. Sci. USA. 2013 and Schreiber J., et al., Proc. Natl. Acad. Sci. USA. 2013, which are herein incorporated by reference).

9. Array or Bead Hybridization

Methylated DNA fractions of the genome, usually obtained by immunoprecipitation, could be used for hybridization with microarrays. Currently available examples of such arrays include: the Human CpG Island Microarray Kit (Agilent), the GeneChip Human Promoter 1.0R Array and the GeneChip Human Tiling 2.0R Array Set (Affymetrix).

The search for differentially-methylated regions using bisulfite-converted DNA could be done with the use of different techniques. Some of them are easier to perform and analyse than others, because only a fraction of the genome is used. The most pronounced functional effect of DNA methylation occurs within gene promoter regions, enhancer regulatory elements and 3' untranslated regions (3'UTRs). Assays that focus on these specific regions, such as the Infinium HumanMethylation450 Bead Chip array by Illumina, can be used. The arrays can be used to detect methylation status of genes, including miRNA promoters, 5' UTR, 3' UTR, coding regions (~17 CpG per gene) and island shores (regions ~2 kb upstream of the CpG islands).

Briefly, bisulfite-treated genomic DNA is mixed with assay oligos, one of which is complimentary to uracil (converted from original unmethylated cytosine), and another is complimentary to the cytosine of the methylated (and therefore protected from conversion) site. Following hybridization, primers are extended and ligated to locus-specific oligos to create a template for universal PCR. Finally, labelled PCR primers are used to create detectable products that are immobilized to bar-coded beads, and the signal is measured. The ratio between two types of beads for each locus (individual CpG) is an indicator of its methylation level.

It is possible to purchase kits that utilize the extension of methylation-specific primers for validation studies. In the VeraCode Methylation assay from Illumina, 96 or 384 user-specified CpG loci are analysed with the GoldenGate Assay for Methylation. Differently from the BeadChip assay, the VeraCode assay requires the BeadXpress Reader for scanning.

10. Methyl-Sensitive Cut Counting: Endonuclease Digestion Followed by Sequencing As an alternative to sequencing a substantial amount of methylated (or unmethylated) DNA, one could generate snippets from these regions and map them back to the genome after sequencing. Moreover, coverage in NGS could be good enough to quantify the methylation level for particular loci. The technique of serial analysis of gene expression (SAGE) has been adapted for this purpose and is known as methylation-specific digital karyotyping, as well as a similar technique, called methyl-sensitive cut counting (MSCC).

In summary, in all of these methods, methylation-sensitive endonuclease(s), e.g., HpaII is used for initial digestion of genomic DNA in unmethylated sites followed by adaptor ligation that contains the site for another digestion enzyme that is cut outside of its recognized site, e.g., EcoP15I or MmeI. These ways, small fragments are generated that are located in close proximity to the original HpaII site. Then, NGS and mapping to the genome are performed. The number of reads for each HpaII site correlates with its methylation level.

Recently, a number of restriction enzymes have been discovered that use methylated DNA as a substrate (methylation-dependent endonucleases). Most of them were discovered and are sold by SibEnzyme: BisI, BlsI, GlaI. GluI, KroI, MteI, PcsI, PkrI. The unique ability of these enzymes to cut only methylated sites has been utilized in the method that achieved selective amplification of methylated DNA. Three methylation-dependent endonucleases that are available from New England Biolabs (FspEI, MspJI and LpnPI) are type IIS enzymes that cut outside of the recognition site and, therefore, are able to generate snippets of 32 bp around the fully-methylated recognition site that contains CpG. These short fragments could be sequences and aligned to the reference genome. The number of reads obtained for each specific 32-bp fragment could be an indicator of its methylation level. Similarly, short fragments could be generated from methylated CpG islands with *Escherichia coli*'s methyl-specific endonuclease McrBC, which cuts DNA between two half-sites of (G/A) mC that are lying within 50 bp-3000 bp from each other. This is a very useful tool for isolation of methylated CpG islands that again can be combined with NGS. Being bisulfite-free, these three approaches have a great potential for quick whole genome methylome profiling.

B. Sequencing

In some embodiments, the methods of the disclosure include a sequencing method. Example sequencing methods include those described below.

1. Massively Parallel Signature Sequencing (MPSS).

The first of the next-generation sequencing technologies, massively parallel signature sequencing (or MPSS), was developed in the 1990s at Lynx Therapeutics. MPSS was a bead-based method that used a complex approach of adapter ligation followed by adapter decoding, reading the sequence in increments of four nucleotides. This method made it susceptible to sequence-specific bias or loss of specific sequences. Because the technology was so complex, MPSS was only performed 'in-house' by Lynx Therapeutics and no DNA sequencing machines were sold to independent laboratories. Lynx Therapeutics merged with Solexa (later acquired by Illumina) in 2004, leading to the development of sequencing-by-synthesis, a simpler approach acquired from Manteia Predictive Medicine, which rendered MPSS obsolete. However, the essential properties of the MPSS output were typical of later "next-generation" data types, including hundreds of thousands of short DNA sequences. In the case of MPSS, these were typically used for sequencing cDNA for measurements of gene expression levels. Indeed, the powerful Illumina HiSeq2000, HiSeq2500 and MiSeq systems are based on MPSS.

2. Polony Sequencing.

The Polony sequencing method, developed in the laboratory of George M. Church at Harvard, was among the first next-generation sequencing systems and was used to sequence a full genome in 2005. It combined an in vitro paired-tag library with emulsion PCR, an automated microscope, and ligation-based sequencing chemistry to sequence an *E. coli* genome at an accuracy of >99.9999% and a cost approximately ⅑ that of Sanger sequencing. The technology was licensed to Agencourt Biosciences, subsequently spun out into Agencourt Personal Genomics, and eventually incorporated into the Applied Biosystems SOLiD platform, which is now owned by Life Technologies.

3. 454 pyrosequencing.

A parallelized version of pyrosequencing was developed by 454 Life Sciences, which has since been acquired by Roche Diagnostics. The method amplifies DNA inside water droplets in an oil solution (emulsion PCR), with each droplet containing a single DNA template attached to a single primer-coated bead that then forms a clonal colony. The sequencing machine contains many picoliter-volume wells each containing a single bead and sequencing enzymes. Pyrosequencing uses luciferase to generate light for detection of the individual nucleotides added to the nascent DNA, and the combined data are used to generate sequence readouts. This technology provides intermediate read length and price per base compared to Sanger sequencing on one end and Solexa and SOLiD on the other.

4. Illumina (Solexa) Sequencing.

Solexa, now part of Illumina, developed a sequencing method based on reversible dye-terminators technology, and engineered polymerases, that it developed internally. The terminated chemistry was developed internally at Solexa and the concept of the Solexa system was invented by Balasubramanian and Klennerman from Cambridge University's chemistry department. In 2004, Solexa acquired the company Manteia Predictive Medicine in order to gain a massively parallel sequencing technology based on "DNA Clusters", which involves the clonal amplification of DNA on a surface. The cluster technology was co-acquired with Lynx Therapeutics of California. Solexa Ltd. later merged with Lynx to form Solexa Inc.

In this method, DNA molecules and primers are first attached on a slide and amplified with polymerase so that local clonal DNA colonies, later coined "DNA clusters", are formed. To determine the sequence, four types of reversible terminator bases (RT-bases) are added and non-incorporated nucleotides are washed away. A camera takes images of the fluorescently labeled nucleotides, then the dye, along with the terminal 3' blocker, is chemically removed from the DNA, allowing for the next cycle to begin. Unlike pyrosequencing, the DNA chains are extended one nucleotide at a time and image acquisition can be performed at a delayed moment, allowing for very large arrays of DNA colonies to be captured by sequential images taken from a single camera.

Decoupling the enzymatic reaction and the image capture allows for optimal throughput and theoretically unlimited sequencing capacity. With an optimal configuration, the ultimately reachable instrument throughput is thus dictated solely by the analog-to-digital conversion rate of the camera, multiplied by the number of cameras and divided by the number of pixels per DNA colony required for visualizing them optimally (approximately 10 pixels/colony). In 2012, with cameras operating at more than 10 MHz A/D conversion rates and available optics, fluidics and enzymatics, throughput can be multiples of 1 million nucleotides/second, corresponding roughly to one human genome equivalent at 1× coverage per hour per instrument, and one human genome re-sequenced (at approx. 30×) per day per instrument (equipped with a single camera).

5. SOLiD Sequencing.

Applied Biosystems' (now a Thermo Fisher Scientific brand) SOLiD technology employs sequencing by ligation. Here, a pool of all possible oligonucleotides of a fixed length are labeled according to the sequenced position. Oligonucleotides are annealed and ligated; the preferential ligation by DNA ligase for matching sequences results in a signal informative of the nucleotide at that position. Before sequencing, the DNA is amplified by emulsion PCR. The resulting beads, each containing single copies of the same DNA molecule, are deposited on a glass slide. The result is sequences of quantities and lengths comparable to Illumina sequencing. This sequencing by ligation method has been reported to have some issue sequencing palindromic sequences.

6. Ion Torrent Semiconductor Sequencing.

Ion Torrent Systems Inc. (now owned by Thermo Fisher Scientific) developed a system based on using standard sequencing chemistry, but with a novel, semiconductor based detection system. This method of sequencing is based on the detection of hydrogen ions that are released during the polymerization of DNA, as opposed to the optical methods used in other sequencing systems. A microwell containing a template DNA strand to be sequenced is flooded with a single type of nucleotide. If the introduced nucleotide is complementary to the leading template nucleotide it is incorporated into the growing complementary strand. This causes the release of a hydrogen ion that triggers a hypersensitive ion sensor, which indicates that a reaction has occurred. If homopolymer repeats are present in the template sequence multiple nucleotides will be incorporated in a single cycle. This leads to a corresponding number of released hydrogens and a proportionally higher electronic signal.

7. DNA Nanoball Sequencing.

DNA nanoball sequencing is a type of high throughput sequencing technology used to determine the entire genomic sequence of an organism. The company Complete Genomics uses this technology to sequence samples submitted by independent researchers. The method uses rolling circle replication to amplify small fragments of genomic DNA into DNA nanoballs. Unchained sequencing by ligation is then used to determine the nucleotide sequence. This method of DNA sequencing allows large numbers of DNA nanoballs to be sequenced per run and at low reagent costs compared to other next generation sequencing platforms. However, only short sequences of DNA are determined from each DNA nanoball which makes mapping the short reads to a reference genome difficult. This technology has been used for multiple genome sequencing projects.

8. Heliscope Single Molecule Sequencing.

Heliscope sequencing is a method of single-molecule sequencing developed by Helicos Biosciences. It uses DNA fragments with added poly-A tail adapters which are attached to the flow cell surface. The next steps involve extension-based sequencing with cyclic washes of the flow cell with fluorescently labeled nucleotides (one nucleotide type at a time, as with the Sanger method). The reads are performed by the Heliscope sequencer. The reads are short, up to 55 bases per run, but recent improvements allow for more accurate reads of stretches of one type of nucleotides. This sequencing method and equipment were used to sequence the genome of the M13 bacteriophage.

9. Single Molecule Real Time (SMRT) Sequencing.

SMRT sequencing is based on the sequencing by synthesis approach. The DNA is synthesized in zero-mode waveguides (ZMWs)—small well-like containers with the capturing tools located at the bottom of the well. The sequencing is performed with use of unmodified polymerase (attached to the ZMW bottom) and fluorescently labelled nucleotides flowing freely in the solution. The wells are constructed in a way that only the fluorescence occurring by the bottom of the well is detected. The fluorescent label is detached from the nucleotide at its incorporation into the DNA strand, leaving an unmodified DNA strand. According to Pacific Biosciences, the SMRT technology developer, this methodology allows detection of nucleotide modifications (such as cytosine methylation). This happens through the observation of polymerase kinetics. This approach allows reads of 20,000 nucleotides or more, with average read lengths of 5 kilobases.]

C. Additional Assay Methods

In some embodiments, methods involve amplifying and/or sequencing one or more target genomic regions using at least one pair of primers specific to the target genomic regions. In certain embodiments, the primers are heptamers. In other embodiments, enzymes are added such as primases or primase/polymerase combination enzyme to the amplification step to synthesize primers.

In some embodiments, arrays can be used to detect nucleic acids of the disclosure. An array comprises a solid support with nucleic acid probes attached to the support. Arrays typically comprise a plurality of different nucleic acid probes that are coupled to a surface of a substrate in different, known locations. These arrays, also described as "microarrays" or colloquially "chips" have been generally described in the art, for example, U.S. Pat. Nos. 5,143,854, 5,445,934, 5,744,305, 5,677,195, 6,040,193, 5,424,186 and Fodor et al., 1991), each of which is incorporated by reference in its entirety for all purposes. Techniques for the synthesis of these arrays using mechanical synthesis methods are described in, e.g., U.S. Pat. No. 5,384,261, incorporated herein by reference in its entirety for all purposes. Although a planar array surface is used in certain aspects, the array may be fabricated on a surface of virtually any shape or even a multiplicity of surfaces. Arrays may be nucleic acids on beads, gels, polymeric surfaces, fibers such as fiber optics, glass or any other appropriate substrate, see U.S. Pat. Nos. 5,770,358, 5,789,162, 5,708,153, 6,040,193 and 5,800,992, which are hereby incorporated in their entirety for all purposes.

In addition to the use of arrays and microarrays, it is contemplated that a number of difference assays could be employed to analyze nucleic acids. Such assays include, but are not limited to, nucleic amplification, polymerase chain reaction, quantitative PCR, RT-PCR, in situ hybridization, digital PCR, dd PCR (digital droplet PCR), nCounter (nanoString), BEAMing (Beads, Emulsions, Amplifications, and Magnetics) (Inostics), ARMS (Amplification Refractory Mutation Systems), RNA-Seq, TAm-Seg (Tagged-Amplicon deep sequencing), PAP (Pyrophosphorolysis-activation polymerization), next generation RNA sequencing, northern hybridization, hybridization protection assay (HPA)(Gen-Probe), branched DNA (bDNA) assay (Chiron), rolling circle amplification (RCA), single molecule hybridization detection (US Genomics), Invader assay (ThirdWave Technologies), and/or Bridge Litigation Assay (Genaco).

Amplification primers or hybridization probes can be prepared to be complementary to a genomic region, biomarker, probe, or oligo described herein. The term "primer" or "probe" as used herein, is meant to encompass any nucleic acid that is capable of priming the synthesis of a nascent nucleic acid in a template-dependent process and/or pairing with a single strand of an oligo of the disclosure, or portion thereof. Typically, primers are oligonucleotides from ten to twenty and/or thirty nucleic acids in length, but longer sequences can be employed. Primers may be provided in double-stranded and/or single-stranded form, although the single-stranded form is preferred.

The use of a probe or primer of between 13 and 100 nucleotides, particularly between 17 and 100 nucleotides in length, or in some aspects up to 1-2 kilobases or more in length, allows the formation of a duplex molecule that is both stable and selective. Molecules having complementary sequences over contiguous stretches greater than 20 bases in length may be used to increase stability and/or selectivity of the hybrid molecules obtained. One may design nucleic acid molecules for hybridization having one or more complementary sequences of 20 to 30 nucleotides, or even longer where desired. Such fragments may be readily prepared, for example, by directly synthesizing the fragment by chemical means or by introducing selected sequences into recombinant vectors for recombinant production.

In one embodiment, each probe/primer comprises at least 15 nucleotides. For instance, each probe can comprise at least or at most 20, 25, 50, 75, 100, 125, 150, 175, 200, 225, 250, 275, 300, 325, 350, 400 or more nucleotides (or any range derivable therein). They may have these lengths and have a sequence that is identical or complementary to a gene described herein. Particularly, each probe/primer has relatively high sequence complexity and does not have any ambiguous residue (undetermined "n" residues). The probes/primers can hybridize to the target gene, including its RNA transcripts, under stringent or highly stringent conditions. It is contemplated that probes or primers may have inosine or other design implementations that accommodate recognition of more than one human sequence for a particular biomarker.

For applications requiring high selectivity, one will typically desire to employ relatively high stringency conditions to form the hybrids. For example, relatively low salt and/or high temperature conditions, such as provided by about 0.02 M to about 0.10 M NaCl at temperatures of about 50° C. to about 70° C. Such high stringency conditions tolerate little, if any, mismatch between the probe or primers and the template or target strand and would be particularly suitable for isolating specific genes or for detecting specific mRNA transcripts. It is generally appreciated that conditions can be rendered more stringent by the addition of increasing amounts of formamide.

In one embodiment, quantitative RT-PCR (such as TaqMan, ABI) is used for detecting and comparing the levels or abundance of nucleic acids in samples. The concentration of the target DNA in the linear portion of the PCR process is proportional to the starting concentration of the target before the PCR was begun. By determining the concentration of the PCR products of the target DNA in PCR reactions that have completed the same number of cycles and are in their linear ranges, it is possible to determine the relative concentrations of the specific target sequence in the original DNA mixture. This direct proportionality between the concentration of the PCR products and the relative abundances in the starting material is true in the linear range portion of the PCR reaction. The final concentration of the target DNA in the plateau portion of the curve is determined by the availability of reagents in the reaction mix and is independent of the original concentration of target DNA. Therefore, the sampling and quantifying of the amplified PCR products may be carried out when the PCR reactions are in the linear portion of their curves. In addition, relative concentrations of the amplifiable DNAs may be normalized to some independent standard/control, which may be based on either internally existing DNA species or externally introduced DNA species. The abundance of a particular DNA species may also be determined relative to the average abundance of all DNA species in the sample.

In one embodiment, the PCR amplification utilizes one or more internal PCR standards. The internal standard may be an abundant housekeeping gene in the cell or it can specifically be GAPDH, GUSB and β-2 microglobulin. These standards may be used to normalize expression levels so that the expression levels of different gene products can be compared directly. A person of ordinary skill in the art would know how to use an internal standard to normalize expression levels.

A problem inherent in some samples is that they are of variable quantity and/or quality. This problem can be overcome if the RT-PCR is performed as a relative quantitative RT-PCR with an internal standard in which the internal standard is an amplifiable DNA fragment that is similar or larger than the target DNA fragment and in which the abundance of the DNA representing the internal standard is roughly 5-100 fold higher than the DNA representing the target nucleic acid region.

In another embodiment, the relative quantitative RT-PCR uses an external standard protocol. Under this protocol, the PCR products are sampled in the linear portion of their amplification curves. The number of PCR cycles that are optimal for sampling can be empirically determined for each target DNA fragment. In addition, the nucleic acids isolated from the various samples can be normalized for equal concentrations of amplifiable DNAs.

A nucleic acid array can comprise at least 1, 2, 3, 4, 5, 6, 7, 8, 9, 10, 15, 20, 25, 30, 35, 40, 45, 50, 60, 70, 80, 90, 100, 150, 200, 250 or more different polynucleotide probes, which may hybridize to different and/or the same biomarkers. Multiple probes for the same gene can be used on a single nucleic acid array. Probes for other disease genes can also be included in the nucleic acid array. The probe density on the array can be in any range. In some embodiments, the density may be or may be at least 50, 100, 200, 300, 400, 500 or more probes/$cm^2$ (or any range derivable therein).

Specifically contemplated are chip-based nucleic acid technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization (see also, Pease et al., 1994; and Fodor et al, 1991). It is contemplated that this technology may be used in conjunction with evaluating the expression level of one or more cancer biomarkers with respect to diagnostic, prognostic, and treatment methods.

Certain embodiments may involve the use of arrays or data generated from an array. Data may be readily available. Moreover, an array may be prepared in order to generate data that may then be used in correlation studies.

Aspects of the disclosure comprise reverse transcription of RNA molecules using a reverse transcriptase enzyme (also "RNA-directed DNA polymerase"; EC 2.7.7.49). Examples of reverse transcriptase enzymes which may be used in methods of the disclosure include AMV RT, MMLV RT, SuperScript III, or SuperScript IV. In some embodiments, the reverse transcriptase enzyme is SuperScript IV.

IV. Clinical and Diagnostic Applications

The methods of the disclosure may be useful for evaluating nucleic acid (e.g., DNA, RNA) for clinical, diagnostic, or research purposes. Certain embodiments relate to a method for evaluating a sample comprising RNA molecules. Example RNA molecules which may be analyzed using the disclosed methods and compositions include messenger RNA (mRNA), transfer RNA (tRNA), ribosomal RNA (rRNA), long noncoding RNA (lncRNA), short noncoding RNA (sncRNA), microRNA (miRNA), small nuclear RNA (snRNA), small nucleolar RNA (snoRNA), small interfering RNA (siRNA), and short hairpin RNA (shRNA). Further aspects relate to a method for evaluating a sample comprising DNA molecules. The evaluation may be the detection or determination of a particular nucleotide, such as pseudouridine or 5-hydroxymethylcytosine.

A sample may include but is not limited to, tissue, cells, or biological material from cells or derived from cells of a subject. In some embodiments, the sample comprises cell-free DNA. In some embodiments, the sample comprises a fertilized egg, a zygote, a blastocyst, or a blastomere. The biological sample may be a heterogeneous or homogeneous population of cells or tissues. The biological sample may be obtained using any method known to the art that can provide a sample suitable for the analytical methods described herein. The sample may be obtained by non-invasive methods including but not limited to: scraping of the skin or cervix, swabbing of the cheek, saliva collection, urine collection, feces collection, collection of menses, tears, or semen.

In some embodiments, the methods of the disclosure can be used in the discovery of novel biomarkers for a disease or condition. In some embodiments, the methods of the disclosure can performed on a sample from a patient to provide a prognosis for a certain disease or condition in the patient. In some embodiments, the methods of the disclosure can be performed on a sample from a patient to predict the patient's response to a particular therapy. In some embodiments, the disease comprises a cancer. In some embodiments, the cancer comprises ovarian, prostate, colon, or lung cancer. In some embodiments, the method is for determining novel biomarkers for ovarian, prostate, colon, or lung cancer by evaluating cell-free nucleic acid (e.g., cell-free RNA) using methods of the disclosure. In some embodiments, the methods of the disclosure may be used on fetal RNA isolated from a pregnant female. In some embodiments, the methods of the disclosure may be used for prenantal diagnostics using fetal RNA isolated from a pregnant female.

V. Detecting a Genetic Signature

Particular embodiments concern the methods of detecting a genetic signature in an individual. In some embodiments, the method for detecting the genetic signature may include selective oligonucleotide probes, arrays, allele-specific hybridization, molecular beacons, restriction fragment length polymorphism analysis, enzymatic chain reaction, flap endonuclease analysis, primer extension, 5'-nuclease analysis, oligonucleotide ligation assay, single strand conformation polymorphism analysis, temperature gradient gel electrophoresis, denaturing high performance liquid chromatography, high-resolution melting, DNA mismatch binding protein analysis, surveyor nuclease assay, sequencing, or a combination thereof, for example. The method for detecting the genetic signature may include fluorescent in situ hybridization, comparative genomic hybridization, arrays, polymerase chain reaction, sequencing, or a combination thereof, for example. The detection of the genetic signature may involve using a particular method to detect one feature of the genetic signature and additionally use the same method or a different method to detect a different feature of the genetic signature. Multiple different methods independently or in combination may be used to detect the same feature or a plurality of features.

A. Single Nucleotide Polymorphism (SNP) Detection

Particular embodiments of the disclosure concern methods of detecting a SNP in an individual. One may employ any of the known general methods for detecting SNPs for detecting the particular SNP in this disclosure, for example. Such methods include, but are not limited to, selective oligonucleotide probes, arrays, allele-specific hybridization, molecular beacons, restriction fragment length polymorphism analysis, enzymatic chain reaction, flap endonuclease analysis, primer extension, 5'-nuclease analysis, oligonucleotide ligation assay, single strand conformation polymorphism analysis, temperature gradient gel electrophoresis, denaturing high performance liquid chromatography, high-resolution melting, DNA mismatch binding protein analysis, surveyor nuclease assay, sequencing, or a combination thereof.

In some embodiments of the disclosure, the method used to detect the SNP comprises sequencing nucleic acid material from the individual and/or using selective oligonucleotide probes. Sequencing the nucleic acid material from the individual may involve obtaining the nucleic acid material from the individual in the form of genomic DNA, complementary DNA that is reverse transcribed from RNA, or RNA, for example. Any standard sequencing technique may be employed, including Sanger sequencing, chain extension sequencing, Maxam-Gilbert sequencing, shotgun sequencing, bridge PCR sequencing, high-throughput methods for sequencing, next generation sequencing, RNA sequencing, or a combination thereof. After sequencing the nucleic acid from the individual, one may utilize any data processing software or technique to determine which particular nucleotide is present in the individual at the particular SNP.

In some embodiments, the nucleotide at the particular SNP is detected by selective oligonucleotide probes. The probes may be used on nucleic acid material from the individual, including genomic DNA, complementary DNA that is reverse transcribed from RNA, or RNA, for example. Selective oligonucleotide probes preferentially bind to a complementary strand based on the particular nucleotide present at the SNP. For example, one selective oligonucleotide probe binds to a complementary strand that has an A nucleotide at the SNP on the coding strand but not a G nucleotide at the SNP on the coding strand, while a different selective oligonucleotide probe binds to a complementary strand that has a G nucleotide at the SNP on the coding strand but not an A nucleotide at the SNP on the coding strand. Similar methods could be used to design a probe that selectively binds to the coding strand that has a C or a T nucleotide, but not both, at the SNP. Thus, any method to determine binding of one selective oligonucleotide probe over another selective oligonucleotide probe could be used to determine the nucleotide present at the SNP.

One method for detecting SNPs using oligonucleotide probes comprises the steps of analyzing the quality and measuring quantity of the nucleic acid material by a spectrophotometer and/or a gel electrophoresis assay; processing the nucleic acid material into a reaction mixture with at least one selective oligonucleotide probe, PCR primers, and a mixture with components needed to perform a quantitative PCR (qPCR), which could comprise a polymerase, deoxynucleotides, and a suitable buffer for the reaction; and cycling the processed reaction mixture while monitoring the reaction. In one embodiment of the method, the polymerase used for the qPCR will encounter the selective oligonucleotide probe binding to the strand being amplified and, using endonuclease activity, degrade the selective oligonucleotide probe. The detection of the degraded probe determines if the probe was binding to the amplified strand.

Another method for determining binding of the selective oligonucleotide probe to a particular nucleotide comprises using the selective oligonucleotide probe as a PCR primer, wherein the selective oligonucleotide probe binds preferentially to a particular nucleotide at the SNP position. In some embodiments, the probe is generally designed so the 3' end of the probe pairs with the SNP. Thus, if the probe has the correct complementary base to pair with the particular nucleotide at the SNP, the probe will be extended during the amplification step of the PCR. For example, if there is a T nucleotide at the 3' position of the probe and there is an A nucleotide at the SNP position, the probe will bind to the SNP and be extended during the amplification step of the PCR. However, if the same probe is used (with a T at the 3' end) and there is a G nucleotide at the SNP position, the probe will not fully bind and will not be extended during the amplification step of the PCR.

In some embodiments, the SNP position is not at the terminal end of the PCR primer, but rather located within the PCR primer. The PCR primer should be of sufficient length and homology in that the PCR primer can selectively bind to one variant, for example the SNP having an A nucleotide, but not bind to another variant, for example the SNP having a G nucleotide. The PCR primer may also be designed to selectively bind particularly to the SNP having a G nucleotide but not bind to a variant with an A, C, or T nucleotide. Similarly, PCR primers could be designed to bind to the SNP having a C or a T nucleotide, but not both, which then does not bind to a variant with a G, A, or T nucleotide or G, A, or C nucleotide respectively. In particular embodiments, the PCR primer is at least or no more than 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, or more nucleotides in length with 100% homology to the template sequence, with the potential exception of non-homology the SNP location. After several rounds of amplifications, if the PCR primers generate the expected band size, the SNP can be determined to have the A nucleotide and not the G nucleotide.

B. Copy Number Variation Detection

Particular embodiments of the disclosure concern methods of detecting a copy number variation (CNV) of a particular allele. One can utilize any known method for detecting CNVs to detect the CNVs. Such methods include fluorescent in situ hybridization, comparative genomic hybridization, arrays, polymerase chain reaction, sequencing, or a combination thereof, for example. In some embodiments, the CNV is detected using an array, wherein the array is capable of detecting CNVs on the entire X chromosome and/or all targets of miR-362. Array platforms such as those from Agilent, Illumina, or Affymetrix may be used, or custom arrays could be designed. One example of how an array may be used includes methods that comprise one or more of the steps of isolating nucleic acid material in a suitable manner from an individual suspected of having the CNV and, at least in some cases from an individual or reference genome that does not have the CNV; processing the nucleic acid material by fragmentation, labelling the nucleic acid with, for example, fluorescent labels, and purifying the fragmented and labeled nucleic acid material; hybridizing the nucleic acid material to the array for a sufficient time, such as for at least 24 hours; washing the array after hybridization; scanning the array using an array scanner; and analyzing the array using suitable software. The software may be used to compare the nucleic acid material from the individual suspected of having the CNV to the nucleic acid material of an individual who is known not to have the CNV or a reference genome.

In some embodiments, detection of a CNV is achieved by polymerase chain reaction (PCR). PCR primers can be employed to amplify nucleic acid at or near the CNV wherein an individual with a CNV will result in measurable higher levels of PCR product when compared to a PCR product from a reference genome. The detection of PCR product amounts could be measured by quantitative PCR (qPCR) or could be measured by gel electrophoresis, as examples. Quantification using gel electrophoresis comprises subjecting the resulting PCR product, along with nucleic acid standards of known size, to an electrical current on an agarose gel and measuring the size and intensity of the resulting band. The size of the resulting band can be compared to the known standards to determine the size of the resulting band. In some embodiments, the amplification of the CNV will result in a band that has a larger size than a band that is amplified, using the same primers as were used to detect the CNV, from a reference genome or an individual that does not have the CNV being detected. The resulting band from the CNV amplification may be nearly double, double, or more than double the resulting band from the reference genome or the resulting band from an individual that does not have the CNV being detected. In some embodiments, the CNV can be detected using nucleic acid sequencing. Sequencing techniques that could be used include, but are not limited to, whole genome sequencing, whole exome sequencing, and/or targeted sequencing.

C. DNA Sequencing

In some embodiments, DNA may be analyzed by sequencing. The DNA may be prepared for sequencing by any method known in the art, such as library preparation, hybrid capture, sample quality control, product-utilized ligation-based library preparation, or a combination thereof. The DNA may be prepared for any sequencing technique. In some embodiments, a unique genetic readout for each sample may be generated by genotyping one or more highly polymorphic SNPs. In some embodiments, sequencing, such as 76 base pair, paired-end sequencing, may be performed to cover approximately 70%, 75%, 80%, 85%, 90%, 95%, 99%, or greater percentage of targets at more than 20×, 25×, 30×, 35×, 40×, 45×, 50×, or greater than 50× coverage. In certain embodiments, mutations, SNPS, INDELS, copy number alterations (somatic and/or germline), or other genetic differences may be identified from the sequencing using at least one bioinformatics tool, including VarScan2, any R package (including CopywriteR) and/or Annovar.

D. RNA Sequencing

In some embodiments, RNA may be analyzed by sequencing. The RNA may be prepared for sequencing by any method known in the art, such as poly-A selection, cDNA synthesis, stranded or nonstranded library preparation, or a combination thereof. The RNA may be prepared for any type of RNA sequencing technique, including stranded specific RNA sequencing. In some embodiments, sequencing may be performed to generate approximately 10M, 15M, 20M, 25M, 30M, 35M, 40M or more reads, including paired reads. The sequencing may be performed at a read length of approximately 50 bp, 55 bp, 60 bp, 65 bp, 70 bp, 75 bp, 80 bp, 85 bp, 90 bp, 95 bp, 100 bp, 105 bp, 110 bp, or longer. In some embodiments, raw sequencing data may be converted to estimated read counts (RSEM), fragments per kilobase of transcript per million mapped reads (FPKM), and/or reads per kilobase of transcript per million mapped reads (RPKM). In some embodiments, one or more bioinformatics tools may be used to infer stroma content, immune infiltration, and/or tumor immune cell profiles, such as by using upper quartile normalized RSEM data.

E. Proteomics

In some embodiments, protein may be analyzed by mass spectrometry. The protein may be prepared for mass spectrometry using any method known in the art. Protein, including any isolated protein encompassed herein, may be treated with DTT followed by iodoacetamide. The protein may be incubated with at least one peptidase, including an endopeptidase, proteinase, protease, or any enzyme that cleaves proteins. In some embodiments, protein is incubated with the endopeptidase, LysC and/or trypsin. The protein may be incubated with one or more protein cleaving enzymes at any ratio, including a ratio of pg of enzyme to pg protein at approximately 1:1000, 1:100, 1:90, 1:80, 1:70, 1:60, 1:50, 1:40, 1:30, 1:20, 1:10, 1:1, or any range between. In some embodiments, the cleaved proteins may be purified, such as by column purification. In certain embodiments, purified peptides may be snap-frozen and/or dried, such as dried under vacuum. In some embodiments, the purified peptides may be fractionated, such as by reverse phase chromatography or basic reverse phase chromatography. Fractions may be combined for practice of the methods of the disclosure. In some embodiments, one or more fractions, including the combined fractions, are subject to phosphopeptide enrichment, including phospho-enrichment by affinity chromatography and/or binding, ion exchange chromatography, chemical derivatization, immunoprecipitation, co-precipitation, or a combination thereof. The entirety or a portion of one or more fractions, including the combined fractions and/or phospho-enriched fractions, may be subject to mass spectrometry. In some embodiments, the raw mass spectrometry data may be processed and normalized using at least one relevant bioinformatics tool.

VI. Kits

Certain aspects of the present disclosure also concern kits containing compositions of the disclosure or compositions to implement methods disclosed herein. In some embodiments, disclosed are kits that can be used to modify and/or detect pseudouridine in a target RNA. In some embodiments, disclosed are kits that can be used to modify and/or detect 5-hydroxymethylcytosine in a target RNA or DNA. Each kit may also include additional components that are useful for purifying, amplifying, or sequencing the RNA or DNA, or for other applications of the present disclosure as described herein.

In some embodiments, kits of the present disclosure include a solution comprising a bisulfite salt (also a "bisulfite solution"). In some embodiments, the solution consists essentially of the bisulfite salt. Examples of bisulfite salts which may be included in a solution include sodium bisulfite and ammonium bisulfite. In some embodiments, the bisulfite salt is sodium bisulfite. In some embodiments, the solution has a pH of about, at least about, or at most about 6.5, 6.6, 6.7, 6.81, 6.82, 6.83, 6.84, 6.85, 6.86, 6.87, 6.88, 6.89, 6.9, 6.91, 6.92, 6.93, 6.94, 6.95, 6.96, 6.97, 6.98, 6.99, 7.0, 7.01, 7.02, 7.03, 7.04, 7.05, 7.06, 7.07, 7.08, 7.09, 7.1, 7.2, 7.3, 7.4, 7.5, 7.6, 7.7, 7.8, 7.9, or 8.0, or any range or value derivable therein. In some embodiments, the solution has a pH of 6.5, 6.6, 6.7, 6.81, 6.82, 6.83, 6.84, 6.85, 6.86, 6.87, 6.88, 6.89, 6.9, 6.91, 6.92, 6.93, 6.94, 6.95, 6.96, 6.97, 6.98, 6.99, 7.0, 7.01, 7.02, 7.03, 7.04, 7.05, 7.06, 7.07, 7.08, 7.09, 7.1, 7.2, 7.3, 7.4, 7.5, 7.6, 7.7, 7.8, 7.9, or 8.0, or any range or value derivable therein. In some embodiments, the solution has a pH of about 7.0. In some embodiments, the solution has a pH of 7.0. In some embodiments, the solution has a pH of about 6.95. In some embodiments, the solution has a pH of 6.95. In some embodiments, the solution has a pH of about 7.05. In some embodiments, the solution has a pH of 7.05.

In some embodiments, the solution has at least or about 10, 11, 12, 13, 14, 15, 16, 17, 18, 19, 20, 21, 22, 23, 24, 25, 25.1, 25.2, 25.3, 25.4, 25.5, 25.6, 25.7, 25.8, 25.9, 26, 26.1, 26.2, 26.3, 26.4, 26.5, 26.6, 26.7, 26.8, 26.9, or 27% bisulfite salt (e.g., sodium bisulfite, ammonium bisulfite) by weight (w/w), or any range or value derivable therein. In some embodiments, a bisulfite solution has at least 10% sodium bisulfite by weight. In some embodiments, a bisulfite solution has at least 20% sodium bisulfite by weight. In some embodiments, a bisulfite solution has at least 25% sodium bisulfite by weight. In some embodiments, a bisulfite solution has about 26.4% sodium bisulfite by weight. In some embodiments, a bisulfite solution has at least 10% ammonium bisulfite by weight. In some embodiments, a bisulfite solution has at least 20% ammonium bisulfite by weight. In some embodiments, a bisulfite solution has at least 25% ammonium bisulfite by weight. In some embodiments, a bisulfite solution has about 26.4% ammonium bisulfite by weight.

In some embodiments, a kit of the disclosure comprises instructions for use. In some embodiments, the instructions are instructions for incubating a nucleic acid molecule (e.g., an RNA molecule or a DNA molecule) with an included solution comprising a bisulfite salt. Such instructions may include instructions for providing the conditions necessary for modification of all pseudouridines or 5-hydroxymethylcytosines on the nucleic acid molecule. Such conditions may include, for example, pH conditions, temperature conditions, incubation time, etc. Examples of such conditions necessary for modification of pseudouridines or 5-hydroxymethylcytosines are disclosed herein. In some embodiments, the instructions comprise instructions for incubating the nucleic acid molecule for, for at most, or for at least 12, 11, 10, 9, 8, 7, 6, 5, or 4 hours, or any range or value derivable therein. In some embodiments, the instructions comprise instructions for incubating the nucleic acid molecule for 4 hours. In some embodiments, the instructions comprise instructions for incubating the nucleic acid molecule for at most 30 minutes. In some embodiments, the instructions comprise instructions for incubating the nucleic acid molecule for at most, about, or exactly 30, 25, 20, 15, 10, or 5 minutes, or any range or value derivable therein. In some embodiments, the instructions comprise instructions for incubating the nucleic acid molecule at a temperature of between about 65° C. and about 75° C. In some embodiments, the instructions comprise instructions for incubating the nucleic acid molecule at a temperature of about 60, 61, 62, 63, 64, 65, 66, 67, 68, 69, 70, 71, 72, 73, 74, 75, 76, 77, 78, 79, or 80° C., or any range or value derivable therein. In some embodiments, the instructions comprise instructions for incubating the nucleic acid molecule at a temperature of about 70° C. In some embodiments, the instructions comprise instructions for incubating the nucleic acid molecule at a temperature of 70° C. In some embodiments, the instructions comprise instructions for incubating the nucleic acid (e.g., DNA) molecule at a temperature of at least, about, or exactly 90, 91, 92, 93, 94, 95, 96, 97, 98, 98.5, 99° C., or any range or value derivable therein. In some embodiments, the instructions comprise instructions for incubating the nucleic acid (e.g., DNA) molecule at a temperature of about 98° C. In some embodiments, the instructions comprise instructions for incubating the nucleic acid (e.g., DNA) molecule at a temperature of 98° C.

In some embodiments, the kit comprises a reverse transcriptase (RT) enzyme. In some embodiments, the RT enzyme is AMV RT, MMLV RT, SuperScript III, or SuperScript IV. In some embodiments, the reverse transcriptase enzyme is SuperScript IV.

In some embodiments, the kit comprises a polynucleotide kinase enzyme. In some embodiments, the polynucleotide kinase enzyme is T4 polynucleotide kinase.

The kit may optionally provide additional components that are useful in the procedure. These optional components include buffers, capture reagents, developing reagents, labels, reacting surfaces, means for detection, control samples, instructions, and interpretive information. In certain embodiments, a kit contains, contains at least, or contains at most 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 100, 500, 1,000 or more probes, primers or primer sets, synthetic molecules or inhibitors, or any value or range and combination derivable therein.

In some embodiments, the kit does not comprise hydroquinone. In some embodiments, the kit does not comprise formamide.

Kits may comprise components, which may be individually packaged or placed in a container, such as a tube, bottle, vial, syringe, or other suitable container means.

Individual components may also be provided in a kit in concentrated amounts; in some embodiments, a component is provided individually in the same concentration as it would be in a solution with other components. Concentrations of components may be provided as 1×, 2×, 5×, 10×, or 20× or more.

In certain aspects, negative and/or positive control nucleic acids, probes, and inhibitors are included in some kit embodiments. In addition, a kit may include a sample that is a negative or positive control, for example a nucleic acid that does not comprise a pseudouridine may be included as a negative control and a nucleic acid that does comprise a pseudouridine may be included as a positive control.

It is specifically contemplated that a kit of the present disclosure may exclude any one or more of the described components in certain embodiments.

EXAMPLES

The following examples are included to demonstrate certain embodiments of the invention. It should be appreciated by those of skill in the art that the techniques disclosed in the examples which follow represent techniques discovered by the inventor to function well in the practice of the invention, and thus can be considered to constitute certain modes for its practice. However, those of skill in the art should, in light of the present disclosure, appreciate that many changes can be made in the specific embodiments which are disclosed and still obtain a like or similar result without departing from the spirit and scope of the invention.

Example 1—Development and Validation of Bisulfite-Induced Deletion Sequencing of Ψ (BID-seq)

First, two commercial bisulfite (BS) kits (Zymo and Epigentek) were tested for conventional BS treatment on synthetic 5-mer RNA oligos AGXGA (X=C or Ψ; SEQ ID NO:1). In both cases, quantitative C-to-U conversion was identified but no detectable conversion of Ψ to Ψ-BS adduct at 50-60° C. The BS conditions reported in RBS-seq (adding 100 mL hydroquinone and formamide; Khoddami et al., 2019) were then repeated with the same RNA oligos to examine the efficiency of Ψ-BS conduct generation. Although MALDI-TOF mass spectrometry showed that C-to-U conversion was quantitative, the formation of Ψ-BS adduct was not stable with no better than 30% observed among six replicates, suggesting that the conversion of Ψ to Ψ-BS in RBS-seq was neither robust nor efficient (FIG. 1).

Figure 2:
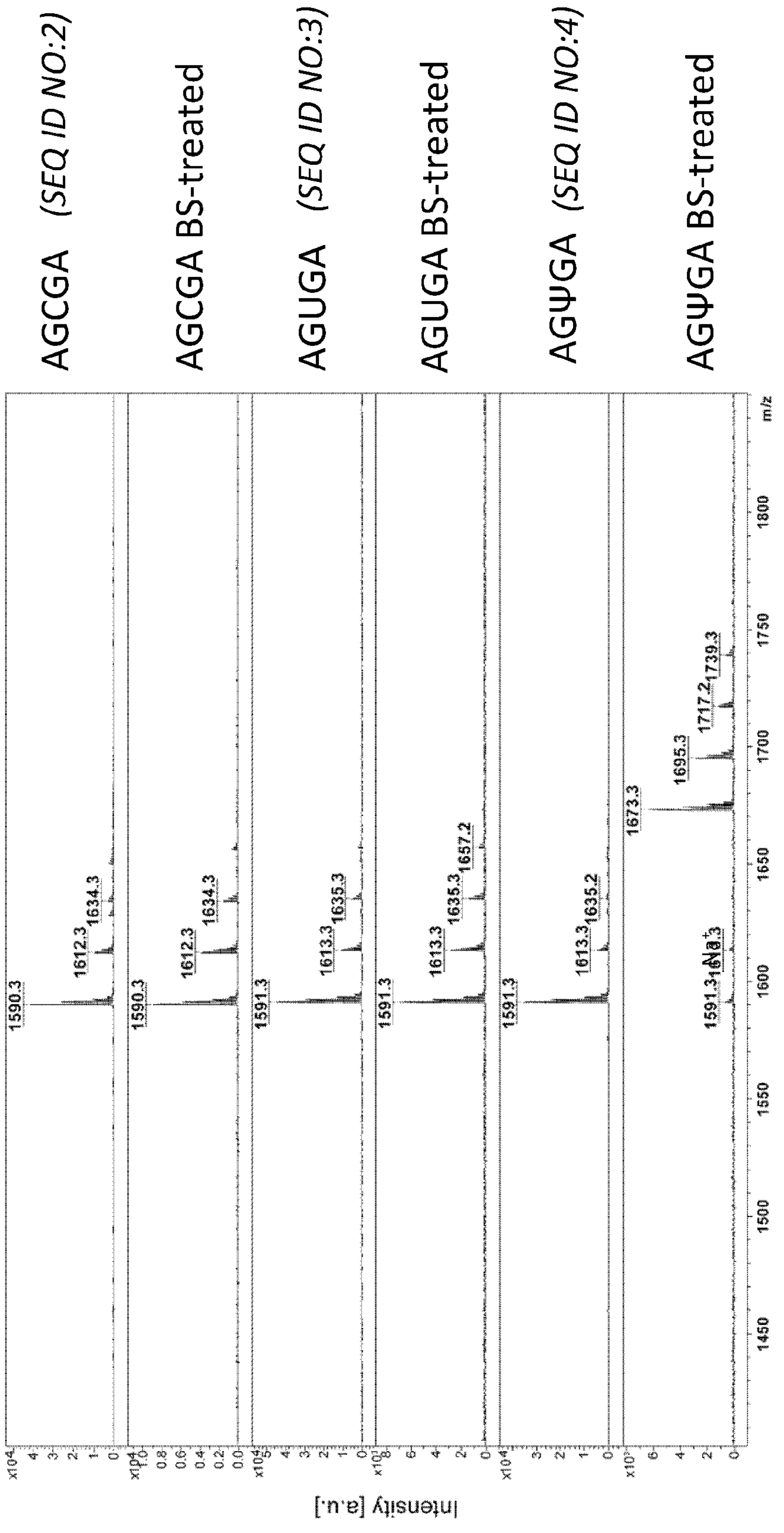
FIG. 2 shows MALDI-TOF mass spectrometry results of AGXGA (X=C, U, or Ψ; SEQ ID NO: 1) reactions with bisulfite under BID-seq conditions described in Example 1. Both C and U showed no change before and after bisulfite treatment, but Ψ was converted to Ψ-BS adduct in almost quantitative yield.

The acidic conditions (pH ~5.1) used by conventional bisulfite treatment and RBS-seq is critical for inducing C-to-U conversion and is known to cause massive RNA degradation. It was hypothesized that neutral pH could inhibit C-to-U conversion and promote formation of the key Ψ-BS adduct and stabilize it upon bisulfite treatment. Indeed, at neutral pH MALDI-TOF showed that Ψ was robustly converted to the Ψ-BS adduct quantitatively, with no C-to-U conversion observed (FIG. 2). The addition of formamide or hydroxyquinone additive used in RBS-seq is not necessary.

Figure 3:
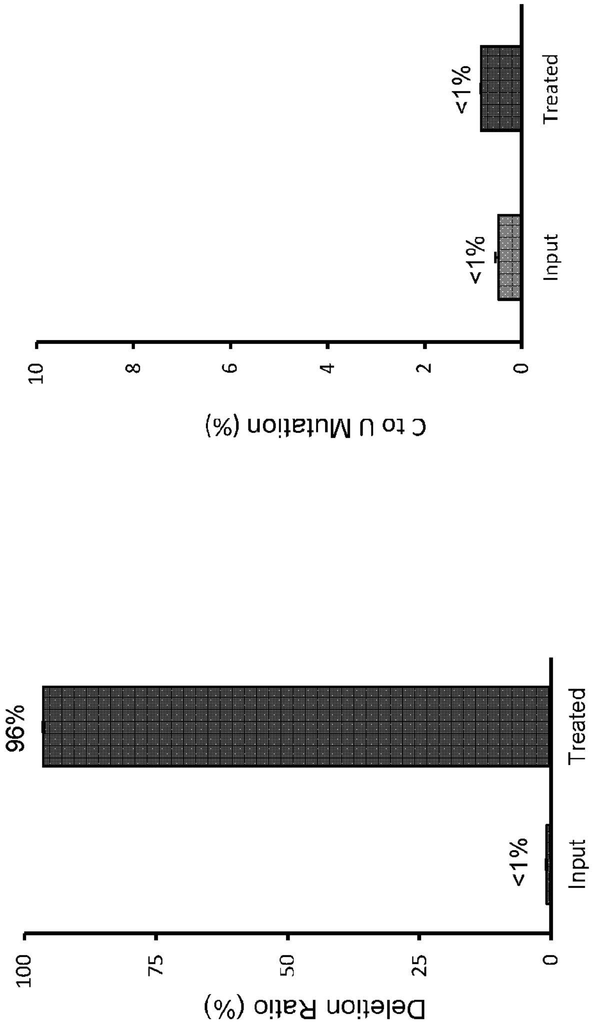
FIG. 3 shows results from optimization of RT enzymes, demonstrating that 96% deletion rate was generated at Ψ site in treated sample, while the input sample's deletion rate was nearly zero. Both the input and treated samples showed nearly no C to U mutation.
Figure 4B:
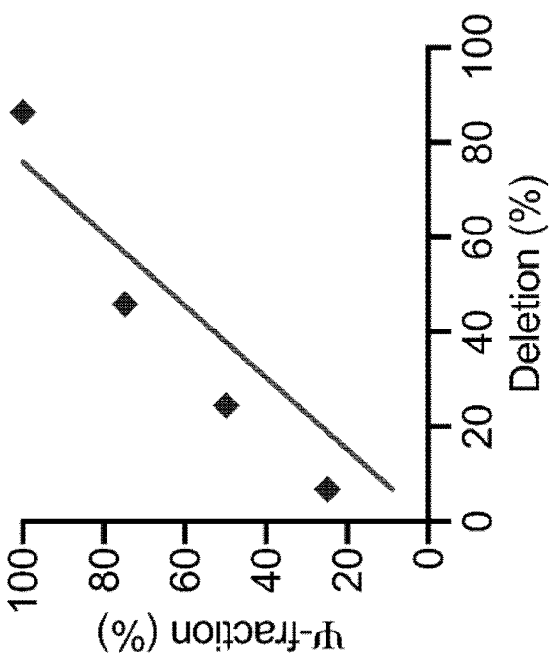
FIG. 4B shows a calibration curve of an oligonucleotide having sequence AGCUAGUCAΨAAUAGUGAC (SEQ ID NO:7).
Figure 4A:
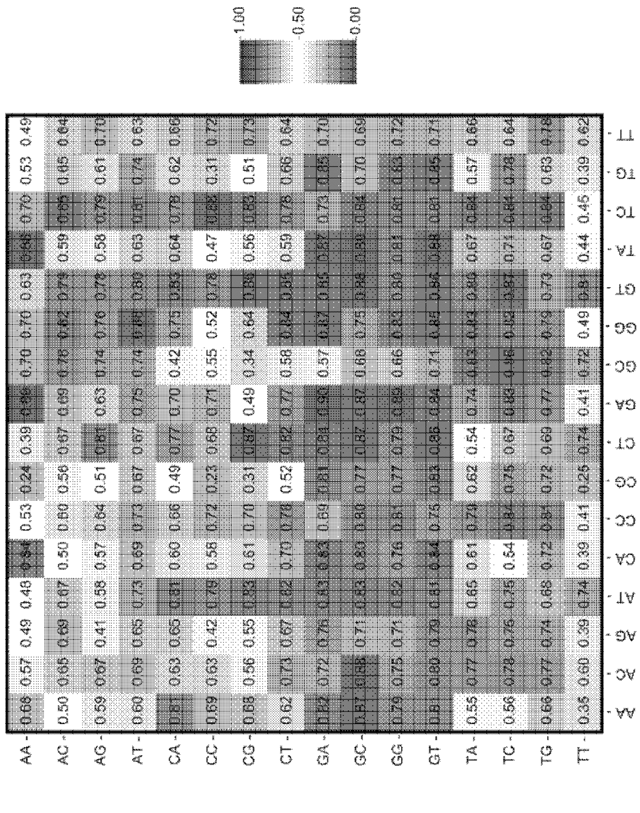
FIG. 4A shows results demonstrating that Ψ deletion rate is dependent on the sequence context.

An RNA model oligo containing one Ψ was then treated with bisulfite at neutral pH and 70° C., and different reverse transcriptases were screened. After RT and PCR amplification, high-throughput sequencing results showed that SuperScript IV (SSIV) RT enzyme afforded a high deletion rate (approximately 96%) specifically at the Ψ site, while the deletion signature was not detectable (<1%) in the untreated control 'input' (FIG. 3). Importantly, the C-to-U conversion rates were <1% in both treated and untreated libraries. To examine the deletion rate dependency on the sequence contexts, libraries were built with another set of RNA oligos carrying one Ψ site, where the oligonucleotides had sequence AGCUAGUNNYNNUAGUGAC (N=A+C+G+U; SEQ ID NO:6). After sequencing, 231 out of 256 motifs exhibited over 50% deletion rates at the Ψ site (FIG. 4A). To calculate the modification fraction at each Ψ site by deletion rates, oligonucleotides having sequence AGCUAGUNNYNNUAGUGAC (N=A+C+G+U; SEQ ID NO:6) or AGCUAGUNNUNNUAGUGAC (N=A+C+G+U; SEQ ID NO:7) were mixed at different ratios to draw calibration curves for each of 256 motifs, with one typical 18S rRNA Ψ motif shown in FIG. 4B. The high mutation rates on 231 motifs, extremely low deletion rate in 'input' background, the use of the Ψ-containing oligos as spike-in calibration probes, and the near linear calibration curves in BID-seq allow sensitive Ψ detection and accurate quantification of Ψ stoichiometry.

Figure 5:
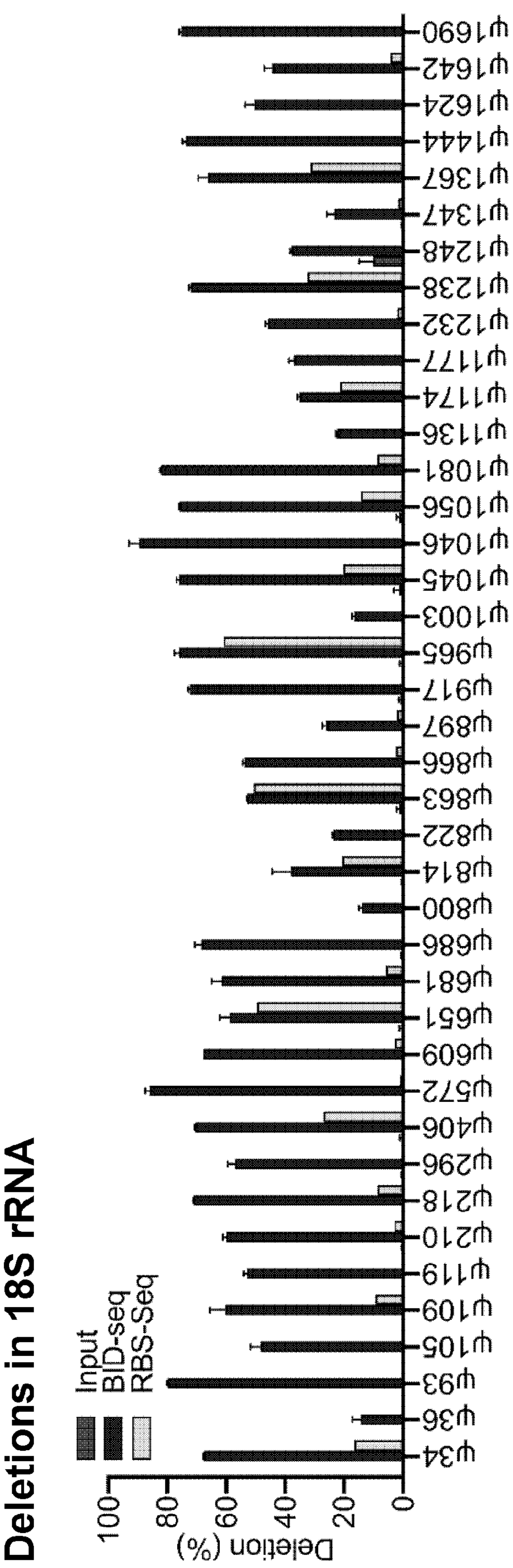
FIG. 5 shows a comparison of deletion rates of the Ψ sites in human 18S rRNA between the BID-seq protocol as described in Example 1 and the RBS-seq protocol of Khoddami, et al., 2019.

To validate BID-seq in biological samples, libraries were built with HeLa total RNA and all known 40 18S rRNA Ψ sites were identified with significant deletion rates of 14-90% in treated libraries (FIG. 5). Deletion rates were 0.01-1.3% at these sites in the untreated input controls, with Ψ1248 as the only exception which turned out to be a different modification of $m^1acp^3\Psi$ (Babaian, A. et al., 2020). The fractions of these 40 Ψ sites were calculated to be 16-99% based on the calibration curve. As comparison, 15 Ψ sites in 18S rRNA were detected by RBS-seq with detectable deletion ratio, but for other Ψ sites the deletion signatures were close to zero (FIG. 5), confirming drastically improved Ψ detection sensitivity by the disclosed BID-seq approach.

Figure 6A:
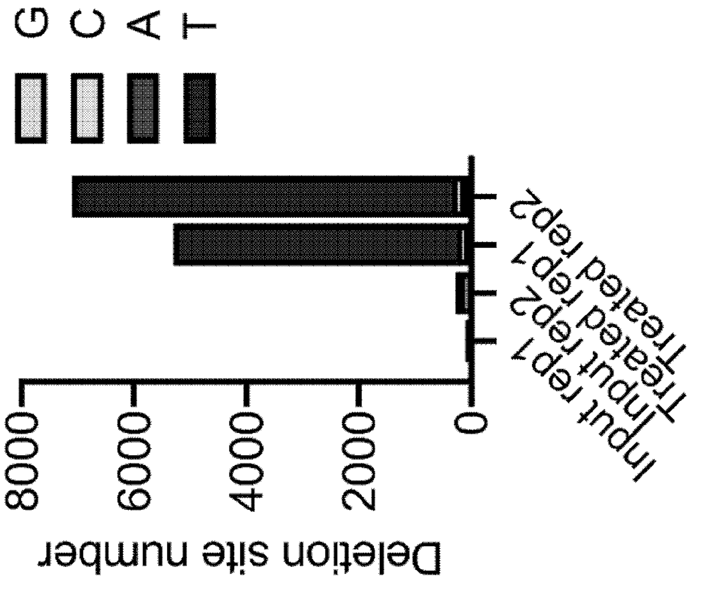
FIGS. 6A-6F show results from analysis of Ψ sites in HeLa mRNA.
Figure 6B:
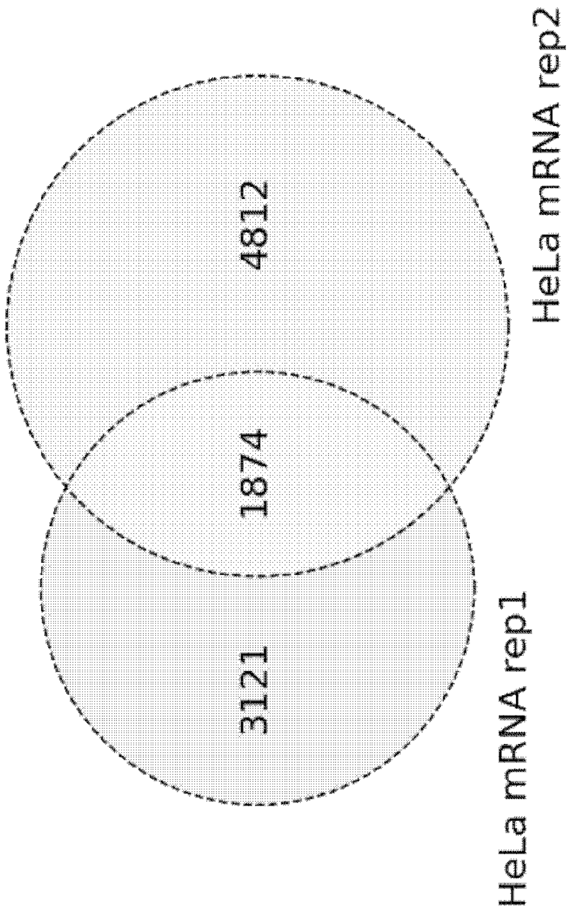
Figure 6C:
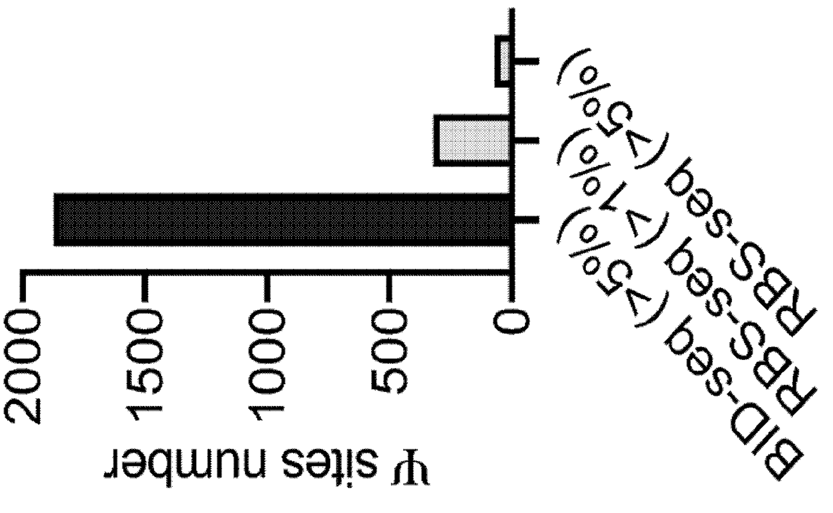
Figure 6D:
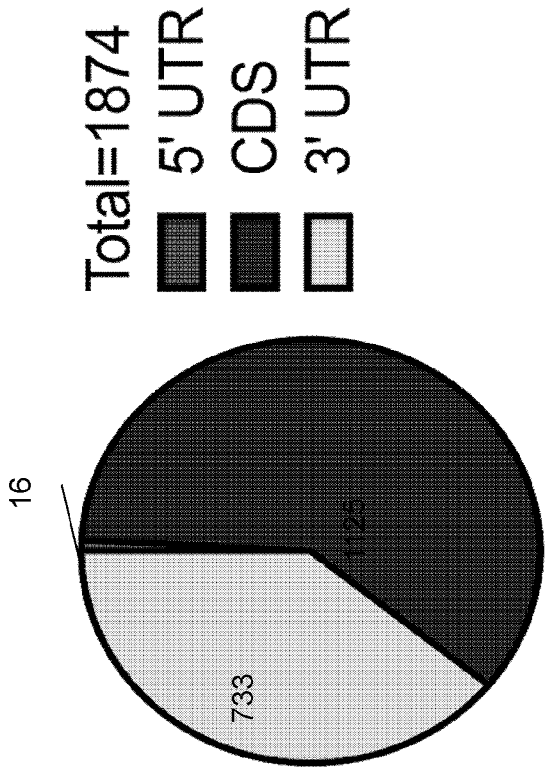
Figure 6F:
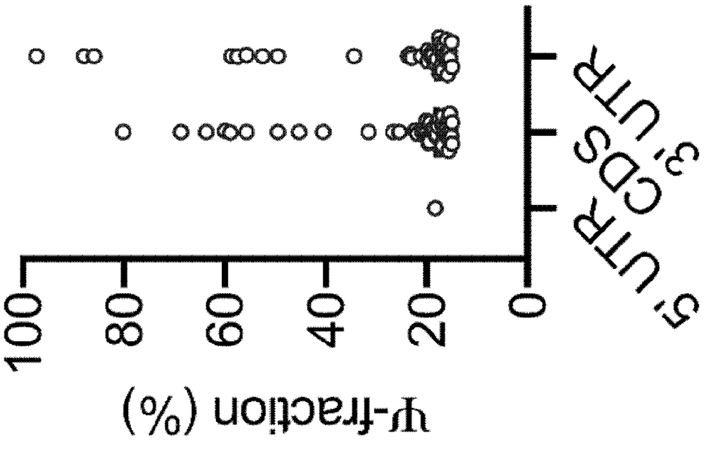
Figure 6E:
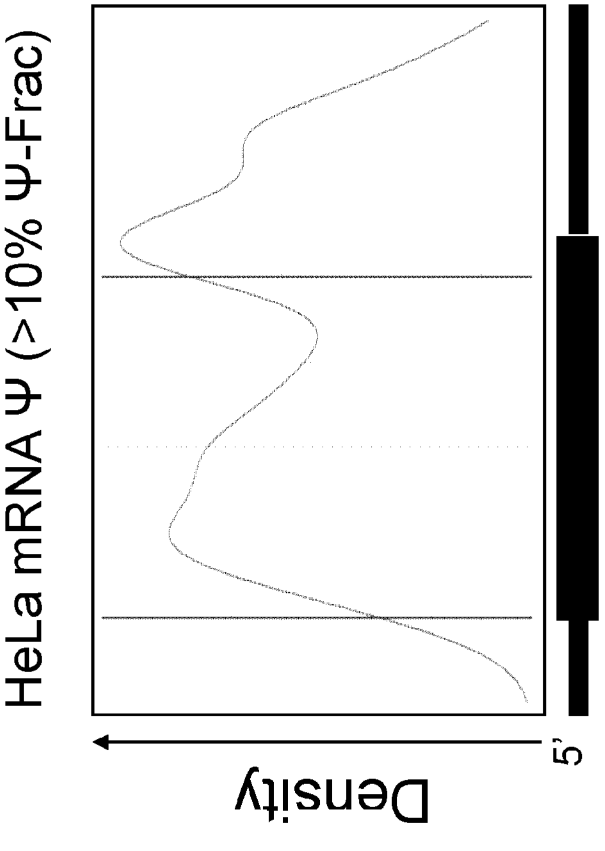

Next, BID-seq was applied to map Ψ in HeLa polyA-tailed RNA. All deletion signals were analyzed for A/C/G/U bases in 'input' and 'BS-treated' libraries. In 'treated' samples (2 replicates), 5305 and 7101 sites were harvested with deletion rate >5.0% (vs. <0.1% in the 'input' library), in which 5037 and 6736 deletions were derived from 'U' sites, respectively (FIG. 6A); however, very few sites with natural deletion rate >5.0% were detected in 'input' samples (2 replicates), suggesting that the deletion signatures were dominantly derived from Ψ. From the 5027 and 6736 Ψ mRNA candidate sites, the confident Ψ sites were chosen by removing the 'U' deletion sites appearing in 'input' and Ψ sites in lncRNA to obtain 1874 mRNA Ψ sites (overlapped by 4995 and 6686 with deletion rate >5%) for downstream studies (FIG. 6B). For comparison, the published RBS-seq datasets were analyzed and it was found that a number of reads that could not be mapped to mRNA due to lower reads complexity (caused by C-to-U conversion). For the reported 322 Ψ sites (RBS-seq) identified in HeLa mRNA with deletion rate >1%, only 72 Ψ sites were above our quality control cutoff deletion rate >5% (FIG. 6C), among which 14 sites (>5% deletion) and 7 sites (>10% deletion) overlapped with BID-seq [1,874 sites (>5%) and 425 (>10%) sites], respectively. Ψ sites in HeLa mRNA mainly distributed in 3'-UTR and CDS (FIGS. 6D-6F), similar to the pattern revealed by CeU-Seq(Li, X. et al., 2015).

BID-seq was used to perform additional analysis of Ψ in rRNA from HeLa cells. To identify highly confident Ψ deletion signatures, the Ψ detection criteria were set as follows: (1) the deletion rate above 5% (with deletion count above 5) in BID-seq libraries; (2) the deletion rate below 1% in 'Input' libraries; (3) total reads coverage depth above 20 in both BID-seq and 'Input' libraries; (4) the deletion rate above 1.5-fold over background in any given sequence motif (defined as the deletion rates detected from RNA probes containing 0% P). In addition, sites were excluded which tend to be false positives, specifically uracil sites at the neighboring nucleotide 3' or 5' to the known Ψ sites.

Figure 7A:
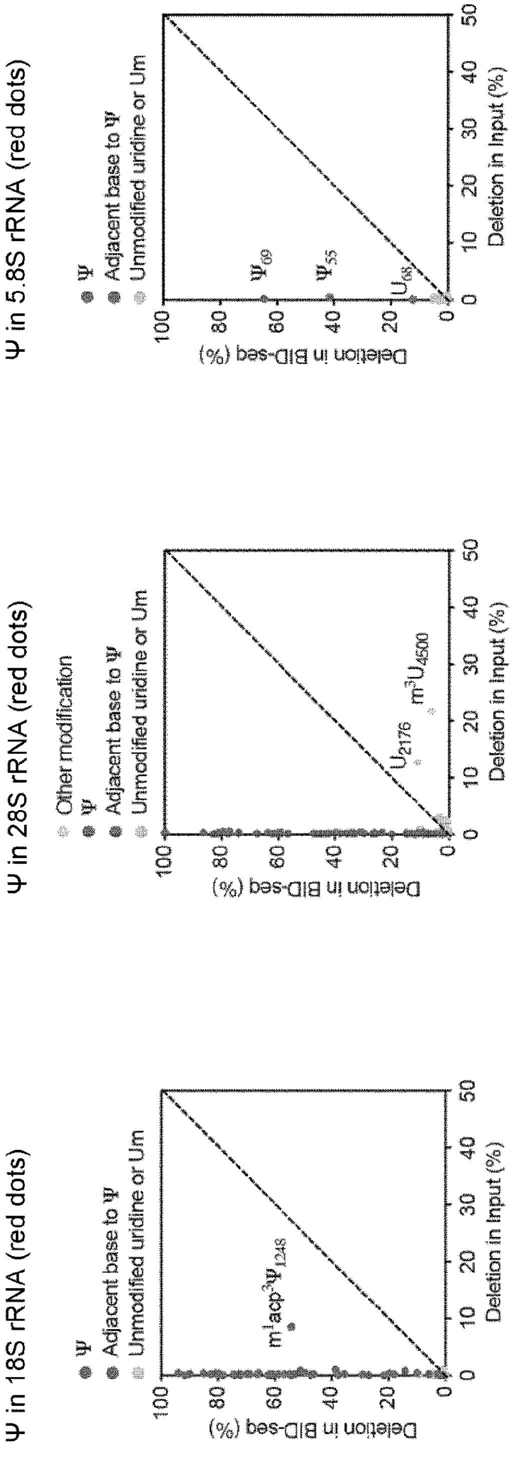
FIGS. 7A-7C show results from analysis of deletion of known Ψ sites in HeLa 18S, 28S, and 5.8S ribosomal RNA.
Figure 7B:
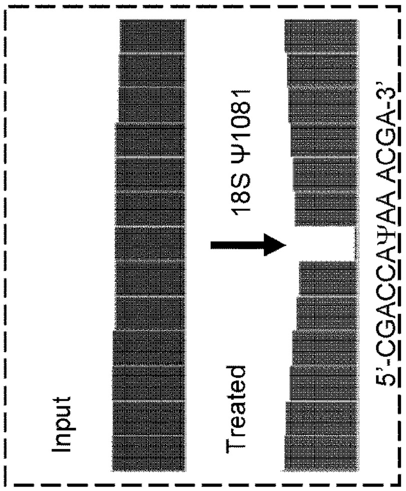
Figure 7C:
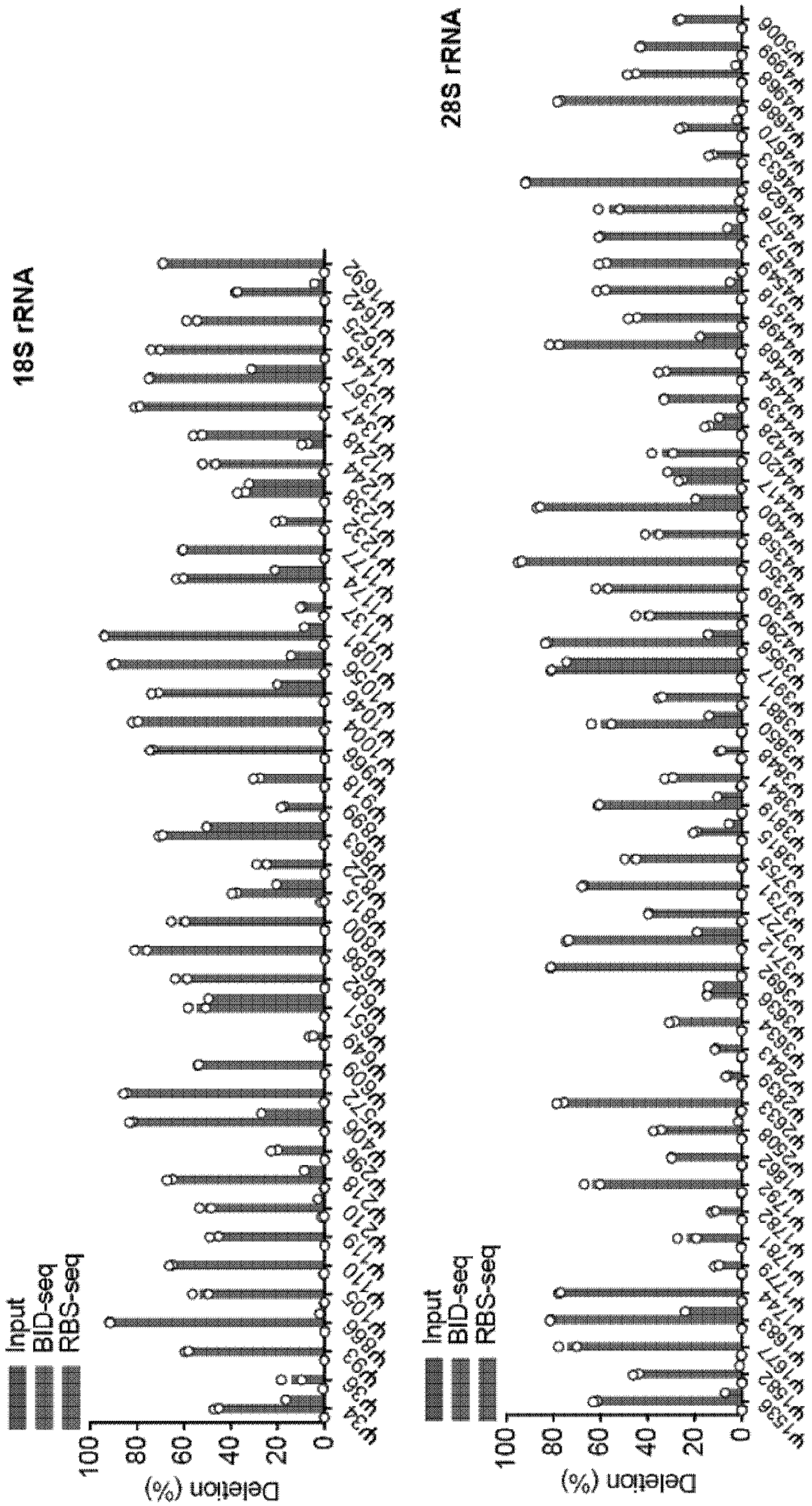

Applying all these criteria for Ψ detection, all 41, 53 and 2 known Ψ sites in HeLa 18S, 28S and 5.8 rRNAs[22], respectively, were identified without any false positives; these known Ψ sites all exhibited significant deletion rates ranging from 5% to 95% in BID-seq (FIG. 7A). A representative highly modified P1081 site in HeLa 18S rRNA is visualized in an original IGV plot (FIG. 7B). Notably, the deletion rates at these Ψ sites in untreated 'input' were <1%, except a few known modifications such as $m^1acp^3\Psi_{1248}$ at 18S rRNA[23], $m^3U_{4500}$ at 28S rRNA and an interesting uncharacterized $U_{2176}$ site at 28S rRNA. Compared to BID-seq, RBS-seq detected 12 and 15 Ψ sites in 18S and 28S rRNA, respectively, because of low deletion rates, with deletion rates close to zero for other known Ψ sites (FIG. 7C).

Figure 8A:
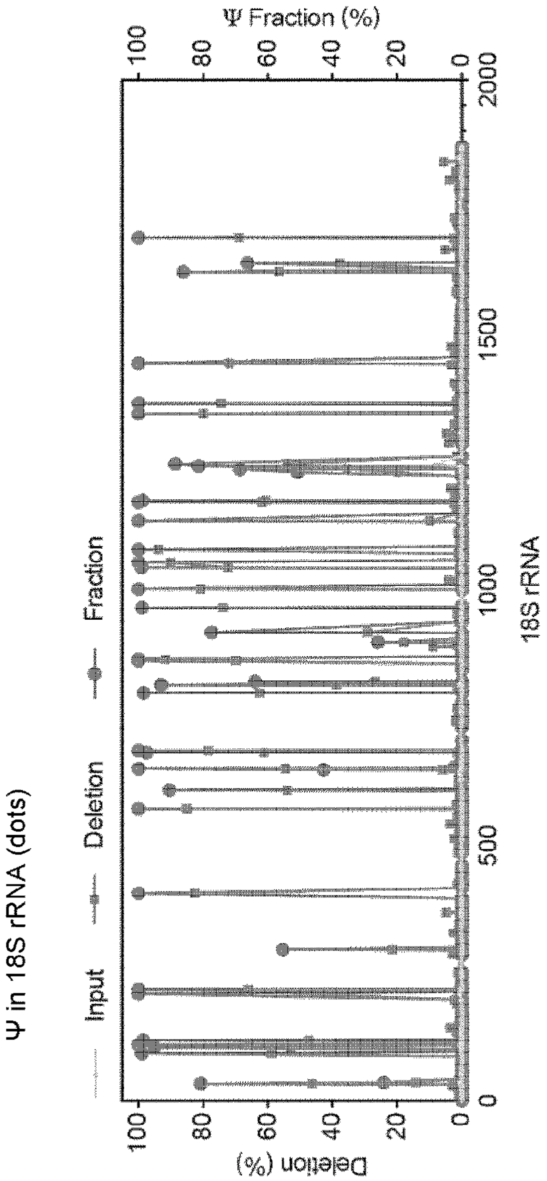
FIGS. 8A-8B show deletion and Ψ fraction detected by BID-seq in HeLa 18S rRNA (FIG. 8A) and 28S rRNA (FIG. 8B).
Figure 8B:
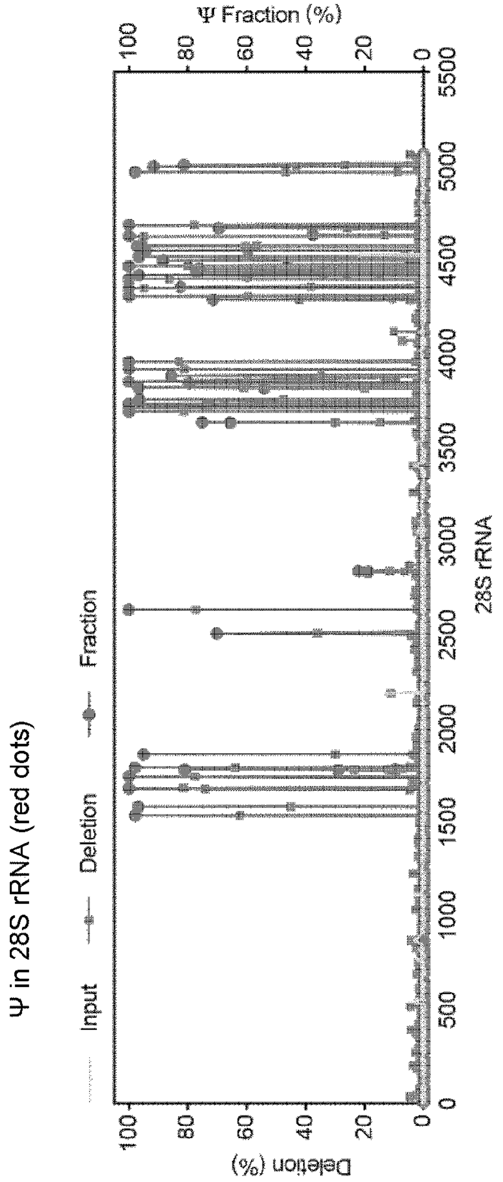

To quantify the modification fraction at each Ψ site by deletion rate, oligo probes were mixed containing NNΨNN and NNUNN (with different stoichiometry of Ψ) as controls to plot calibration curves for these sequence contexts The high mutation rates on 232 motifs, low background for most of these motif contexts, and the approximately hyperbola calibration curves in BID-seq enabled sensitive detection of Ψ as well as estimation of Ψ stoichiometry. Based on the calibration curves, the fractions of these Ψ sites in HeLa 18S, 28S and 5.8S rRNAs were calculated to be ~20-100%, (FIGS. 8A and 8B). BID-seq was also applied to small RNAs (<200 nt) from HeLa cells, and highly modified Ψ sites were validated in both H/ACA box and C/D box snoRNAs, including snoRNA Ψ sites previously revealed by Ψ-seq.

Figure 9:
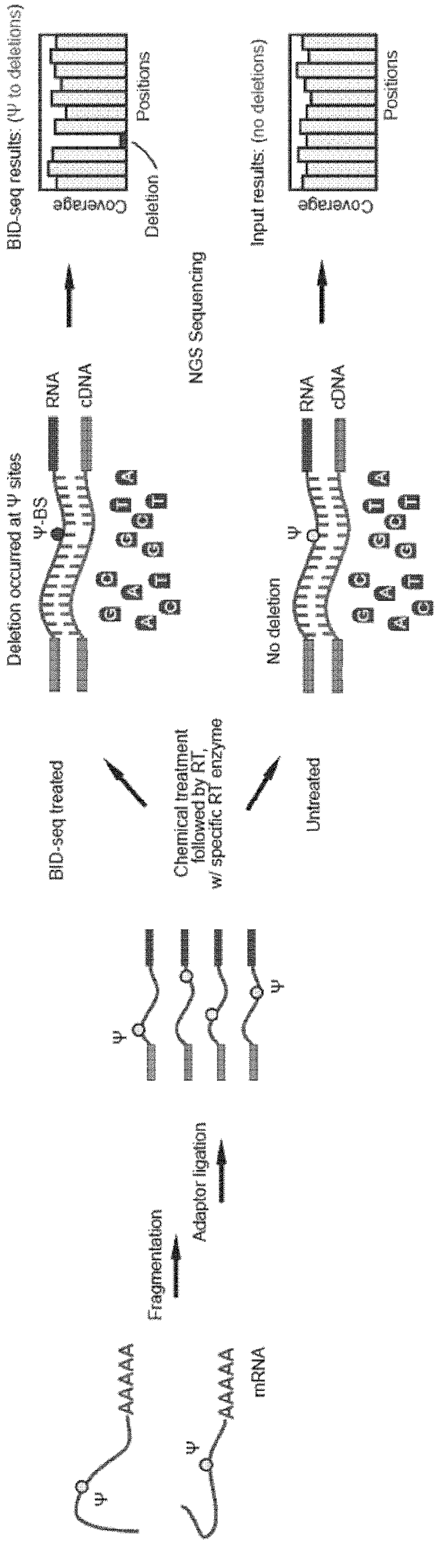
FIG. 9 shows a flowchart of library construction pipeline for BID-seq, revealing Ψ modification fraction by deletion ratio signature.
Figure 10A:
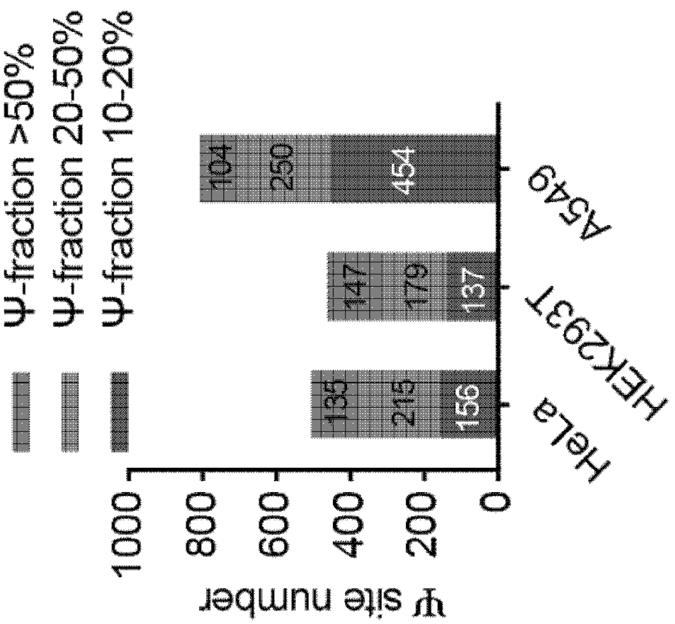
FIGS. 10A-10E show detected Ψ sites in human mRNA.
Figure 10B:
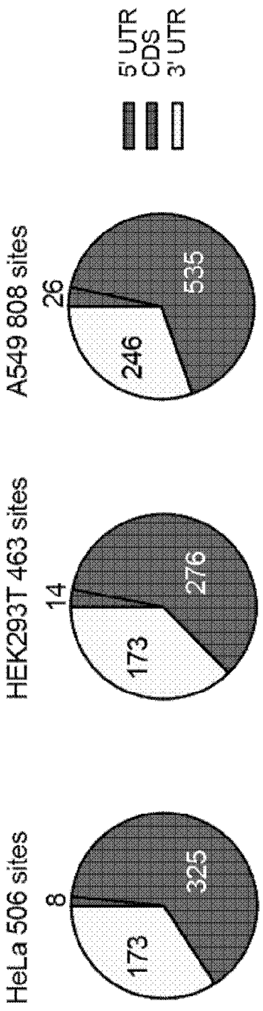
Figure 10C:
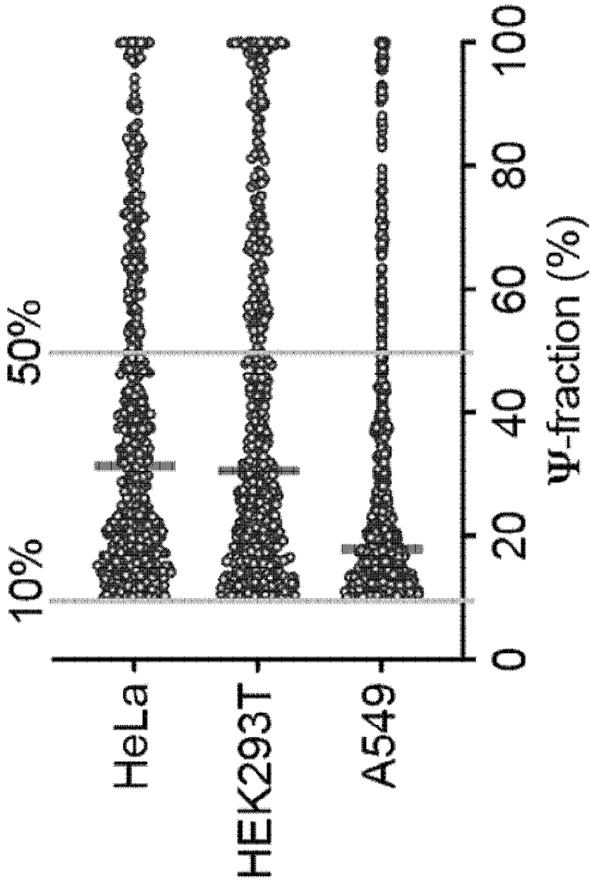
Figure 10D:
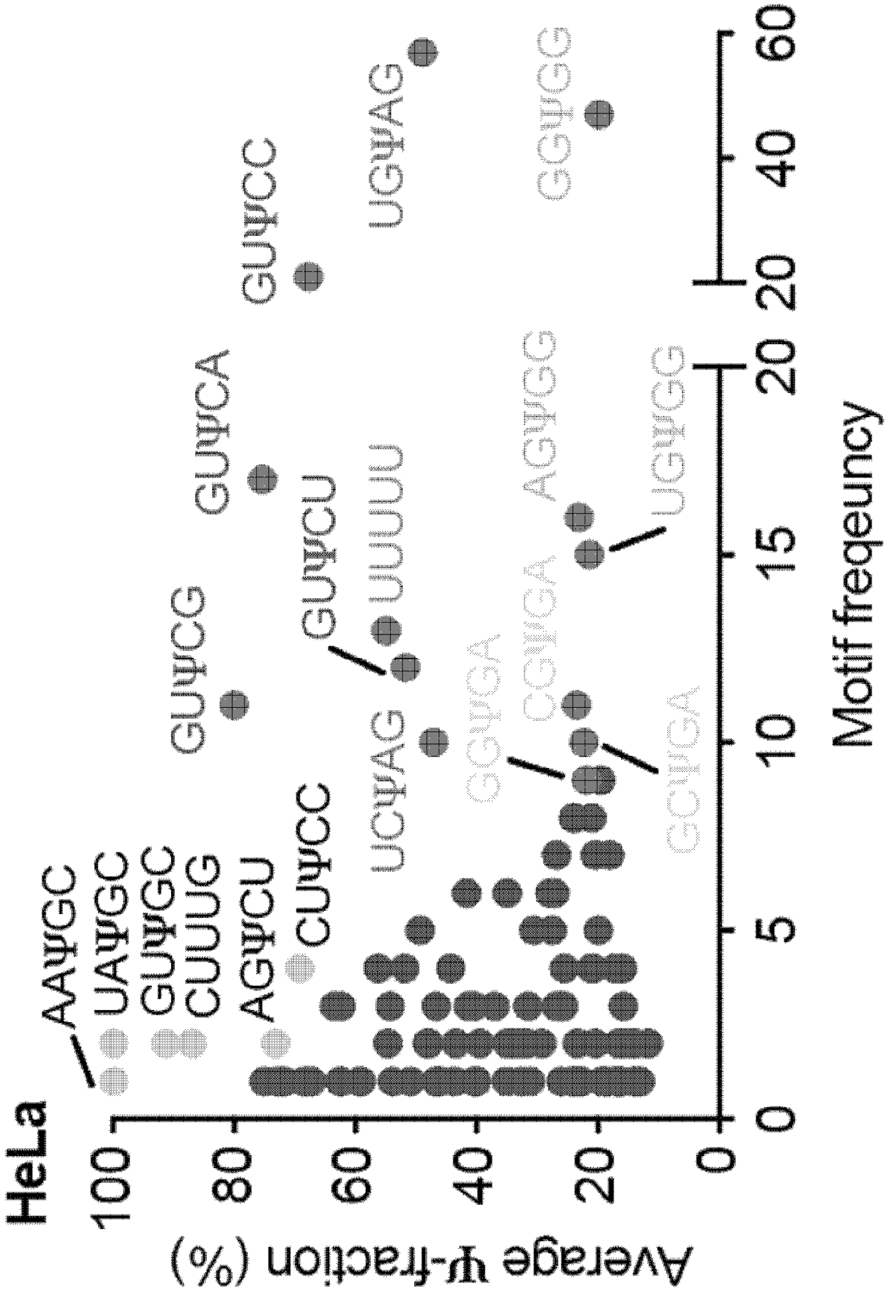
Figure 10E:
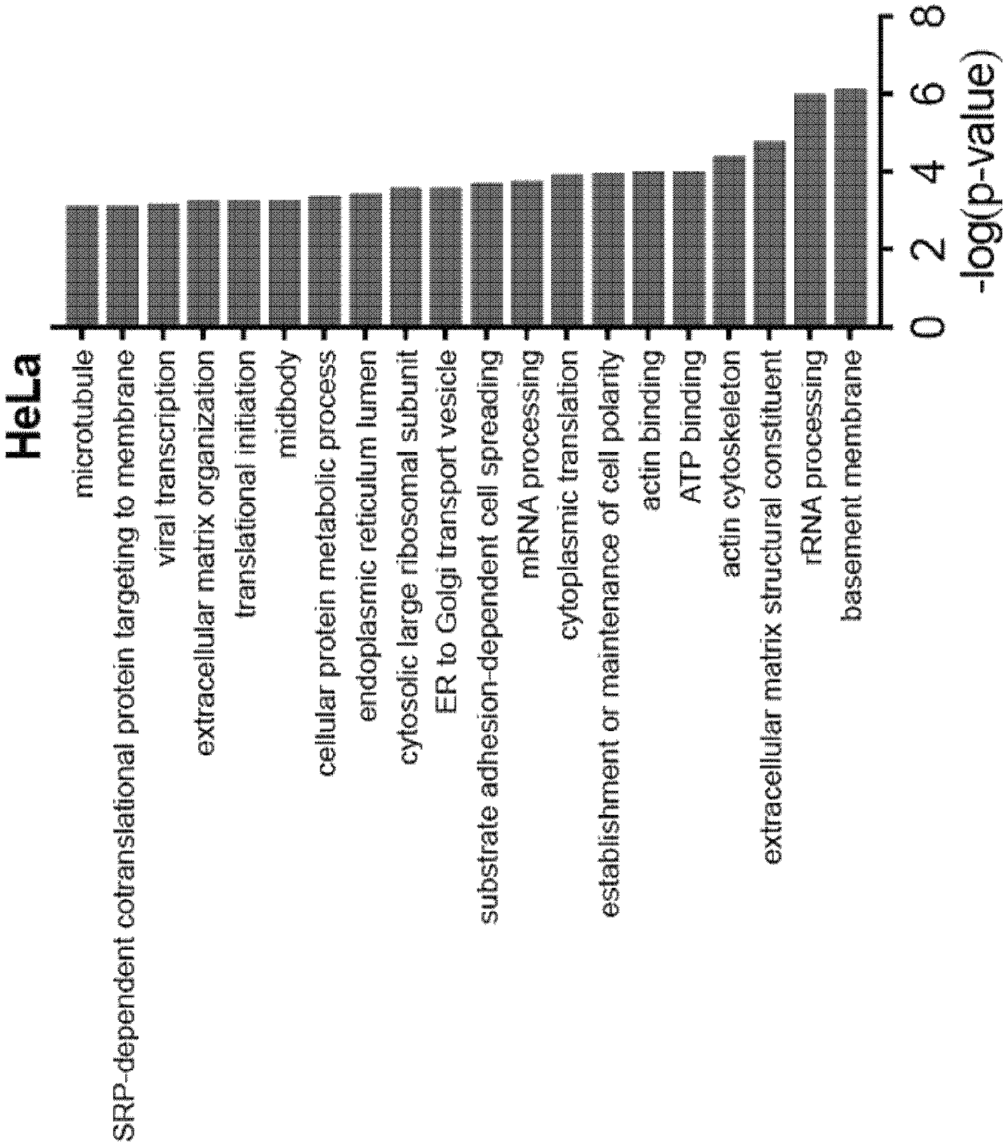
Figure 10F:
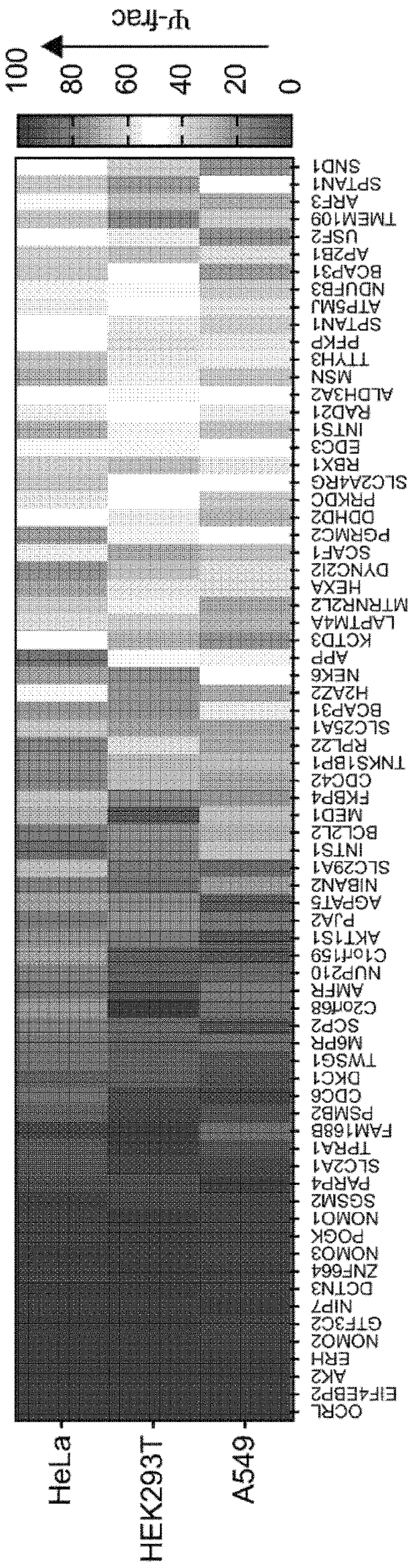
FIG. 10F—The heatmap plot of Ψ-fraction for 72 Ψ sites with above 50% Ψ-fraction in at least one human cell line and above 10% Ψ-fraction in three cell lines, in a matrix of the corresponding gene name vs. each cell line.

BID-seq was optimized to be compatible with low RNA input, then applied to 10-20 ng polyA-tailed RNA from HeLa, HEK293T and A549 cells based on the workflow shown in FIG. 9. In addition to the aforementioned criteria for Ψ detection, one more Ψ modification fraction cutoff was added to focus on mRNA sites >10% Ψ stoichiometry as the confident sites. 506, 463 and 808 confident Ψ sites were identified in mRNA from HeLa, HEK293T and A549 cells, respectively (FIG. 10A), which all showed clear internal deletion signatures. Most of these mRNA Ψ sites displayed the modification fraction at 10-30% (FIG. 10A). 135, 147 and 104 highly modified mRNA Ψ sites (>50% Ψ fraction) were identified in the three human cell lines (FIG. 10A), with a continuous distribution of Ψ fraction from 50% all the way to close to 100% (FIG. 10C). The confident mRNA Ψ sites distribute mostly in CDS and 3'-UTR (FIG. 10B), similar to the distribution pattern observed previously using CeU-seq. In metagene profile, an example of the confident mRNA Ψ sites in A549 cells showed accumulation in the CDS region (FIG. 10B). The common GO clusters of HeLa and A549 cells enrich functions such as microtubule/cytoskeleton, ribosome, membrane, actin binding, ATP binding, protein folding, mRNA processing, etc. (FIG. 10D). Note that Ψ can be commonly shared or cell line specific. 114 sites were uncovered as cell-line-specific highly modified Ψ (>50% Ψ fraction) and 72 sites as highly modified Ψ in at least one human cell line and detectable (>10% Ψfraction) in all three cell lines (FIG. 10E).

Example BID-Seq Protocol

Reagents:

(1). Freshly prepared bisulfite: Saturated bisulfite (26.4% w/w) adjust pH to 7.0. To a mixture of 270 mg sodium sulfite and 34 mg sodium bisulfite, 850 μl RNase-free water was added, pH adjusted, and the mixture was vortexed to ensure the solid was completely dissolved.

```
(2). 3'-NNadaptor:
                                    (SEQ ID NO: 10)
5'rApp-NN NNN CGA TGT AG ATC GGA AGA GCA CAC GTC
T-biotin (Self-made, 11.25 uM, barcode 2)
```

-continued

```
(3). 5'-NNadaptor:
                                    (SEQ ID NO: 11)
5'-GU UCA GAG UUC UAC AGU CCG ACG AUC NNN NN
(Self-made, 11.25 uM)

(4). NEB small RNA library kit

(5). NEB T4 PNK (M0201S)
```

(4). NEB small RNA library kit
(5). NEB T4 PNK (M0201S)

Procedure:

1. Alkaline hydrolysis—Take out RNA and add water to 36 μl, then add 4 μl 1 M $NaHCO_3$ pH=9.2 and incubated at preheated PCR at 95 C for 8 min.

2. Adjust pH to 7.6—Add 1 μl 3 M NaOAc to adjust pH to 7.6.

3. 3'-Repair and 5'-phosphorylation—Added 5 μl T4 PNK buffer and 1 μl T4 PNK and incubated at 37 C for 30 min, then added 5 μl ATP and 0.5 μl T4 PNK and incubated at 37° C. for 1 h, followed by inactivating T4 PNK by heating at 65° C. for 20 min.

4. RCC clean/OCC clean—Purify the samples by RCC eluting with 7.5 μl. Measure the concentration by nanodrop. Purify the 11-12 samples by OCC, eluting with 7.5 μl. Measure the concentration by nanodrop.

5. 3'-Ligation—Take 6 μl around 100 ng RNA and add 1 μl 3'-adaptor, incubated at 70 C for 2 min and immediate put it onto ice, and then add 10 μl buffer and 3 μl 3'-RNA ligase and incubated at 16 C for 16 h.

6. RT primer annealing—Add 4.5 μl water 1 μl RT primer and incubated at 70 C for 5 min, 37 C for 15 min and then 25 C for 15 min. (12 μl)

7. 5'-Ligation—Incubate the 5' adaptor at 70 C for 2 min and transfer to ice. Add to the sample 1 μl 11.25 M 5' adaptor, 1 μl 5' ligation reaction buffer and 2.5 μl 5' ligation enzyme mix. Incubate at 25° C. overnight. Purified by OCC, eluting with 10 μl water.

8. Bisulfite (BS) treatment—Take 2 μl+10.5 μl water to do RT using SSIV for input libraries. Take 2×2.5 μl out+22 μl freshly prepared BS reagent, incubated at 70° C. for 4 h. Then 25 μl 1.5 M Tris 8.8 was added and incubated at 37° C. for 1 h, followed by purification by spin column and OCC, eluting with 14 μl water.

9. Reverse Transcription (RT) reaction—For BS-treated and input libraries: denature and annealing at 65° C. for 5 min, put into ice for 1 min. Prepare the enzyme mix: 1 μl 10 mM dNTP+1 μl 0.1 M DTT, 0.5 μl RNaseOut, 4 μl 5× buffer and 1 μl RT enzyme. Add 7.5 μl enzyme mix to 12.5 μl denatured sample, total 20 μl, incubated at 50° C. for 10 min and then 80 C for 10 min.

10. qPCR—Use 1 μl cDNA. Add 10 μl 2× qPCR MIX, 1 μl SR primer, 1 μl mix primer, 7 μl water. Run the following protocol:

| | |
|---|---|
| Pre-incubation | 95° C.; 600 s |
| x25 | 95° C.; 20 s |
| | 60° C.; 20 s |
| | 72° C.; 20 s |
| Melting curves | 95° C.; 10 s |
| | 65° C.; 60 s |
| | 97° C.; 1 s |

11. PCR amplification & Gel Size Selection—Use 10 μl cDNA to perform PCR and 0.625 μl index primer (see the table below). Add 14.38 μl of PCR mix to each sample and run following protocol:

| | |
|---|---|
| | 94° C.; 30 s |
| x cycles # | 94° C.; 15 s |
| | 62° C.; 30 s |
| | 70° C.; 15 s |
| | 70° C.; 5 min |
| | 4° C. |

PCR Mix;

| | x1 |
|---|---|
| 2x Longamp Taq | 12.5 μl |
| SR primer | 0.625 μl |
| water | 1.25 μl |
| sum | 14.38 μl |

12. Run the 2% agarose gel to purify the libraries.

Additional Example Ψ Treatment Conditions for BID-Seq Method:

To a mixture of 270 mg sodium sulfite and 34 mg sodium bisulfite, 850 μl RNase-free water was added, pH adjusted to between 6.8 and 7.2 (e.g., about 7.0), and the mixture was vortexed to ensure the solid was completely dissolved.

To RNA in 5 μl RNase-free water was added 45 μl freshly prepared reagent, and the mixture was vortexed and spin, and then incubated at 70° C. for 3 h, followed by desulphonation.

Example 2—5hmC Profiling

5hmC-modified loci can serve as informative biomarkers for a variety of human cancers and other complex diseases. Existing methods for studying 5hmC-modified loci include "5hmC-Seal", a chemical labeling and pull-down method to enrich 5hmC-containing fragments for 200-fold, followed by next-generation sequencing (NGS). 5hmC-Seal suffers several limitations in its application to cfDNA for disease biomarker seeking: (1) the chemical labeling of the 5hmC introduces a bulky group at the C5 position, which may partially block DNA polymerases reading through 5hmC sites. (2) 5hmC-Seal uses expensive reagents such as azido-glucose and biotinylation click reaction. Given that hundreds of patients' samples need to be sequenced, the higher cost of the reagents may be prohibitive. (3) 5hmC-Seal includes two steps for introducing biotin handle for enrichment (enzymatic reaction to introduce azido-glucose and click reaction to introduce biotin), and both these two steps need a purification step, thus more hands-on work and more starting cfDNA may be needed for each library construction. Therefore, a more practical 5hmC profiling method which can overcome the above drawbacks is highly desired.

Previously, 5hmC antibody has been used for 5hmC enrichment with the advantage that antibody can be reversibly removed from 5hmC so that DNA polymerase can read through the unmodified 5hmC efficiently. However, 5hmC antibody can only provide 10~20-fold enrichment for 5hmC against C, which may lead to high background and false positives due to non-specific binding.

It has been reported that 5hmC can be converted to cytosine-5-methylenesulfonate (CMS) under conventional (i.e., acidic such as pH<6.5, for example pH 5.1) BS conditions and anti-CMS antibody performed much better than 5hmC antibody in term of enrichment efficiency (Huang, Y. et al., 2012 and Pastor, W. A. et al., 2011). After 5hmC was converted to CMS, anti-CMS antibody enriched CMS with 200-fold enrichment. Therefore, the profiling of 5hmC using anti-CMS antibody is superior to using an anti-5hmC antibody. However, one of the caveats of this method is that conventional BS also converts all cytosines to uracils and thus reduces the complexity of the reads and caused mapping issues. In addition, conventional BS treatment under acidic conditions can lead to severe DNA degradation. Since the non-conventional BS (ncBS) conditions used for BID-seq did not cause C-to-U mutation, it was hypothesized that 5hmC in DNA could be quantitatively converted to the corresponding CMS under ncBS conditions.

Figure 11A:
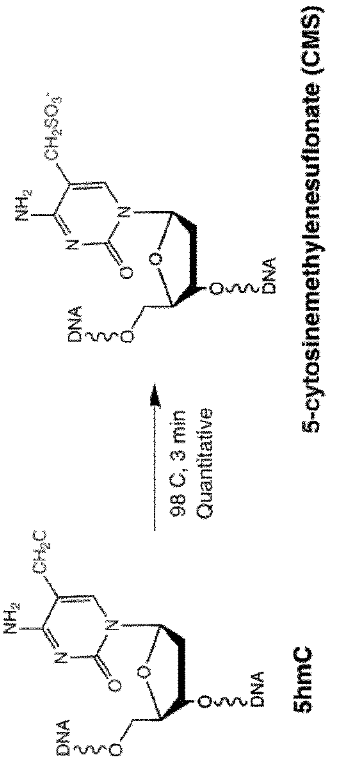
FIGS. 11A-11B show MALDI TOF MS results demonstrating that 5hmC in a 5mer DNA oligo containing a 5hmC modification can be quantitatively converted into CMS within 3 min.
Figure 11B:
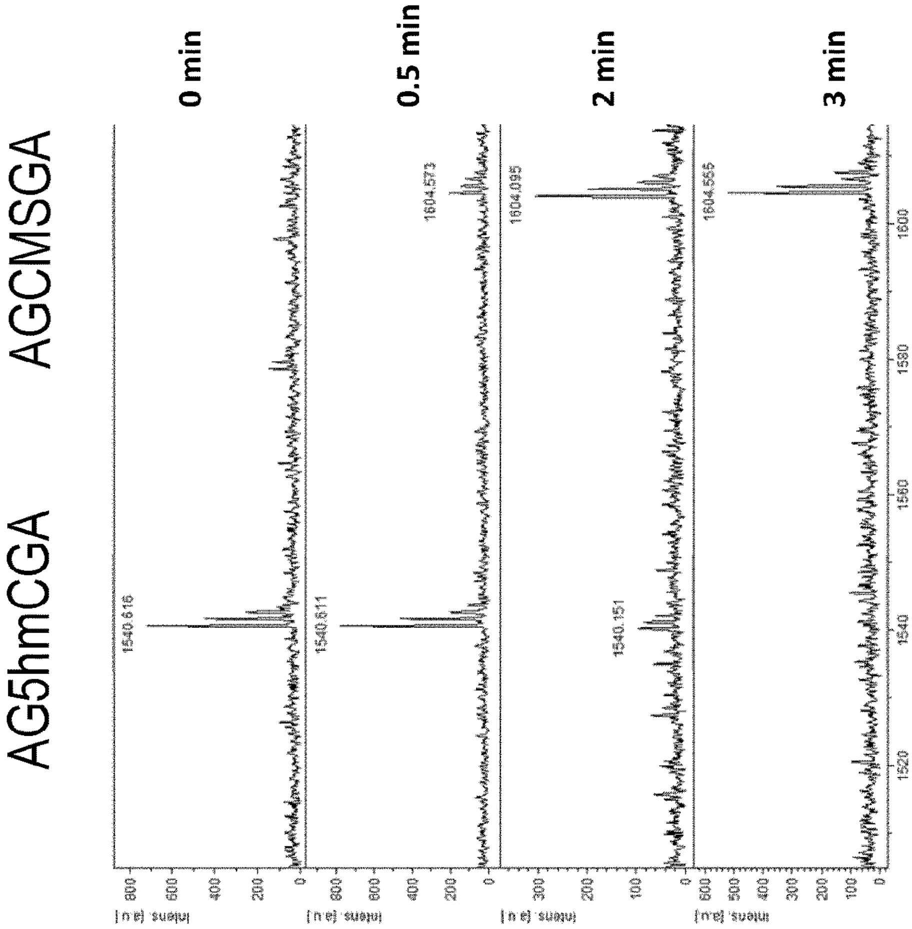
Figure 12B:
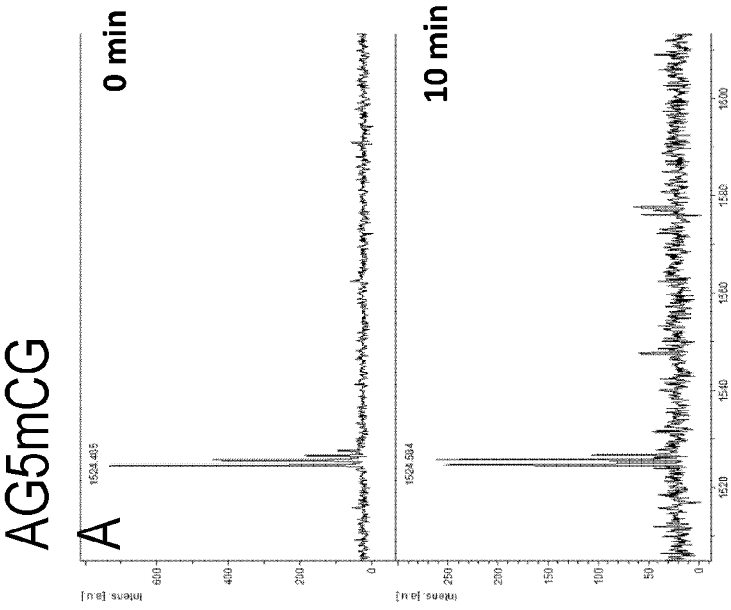
FIGS. 12A-12C show Maldi TOF MS results demonstrating that none of C (FIG. 12A), 5mC (FIG. 12B) or T (FIG. 12C) reacted with BS under the optimized conditions.
Figure 12A:
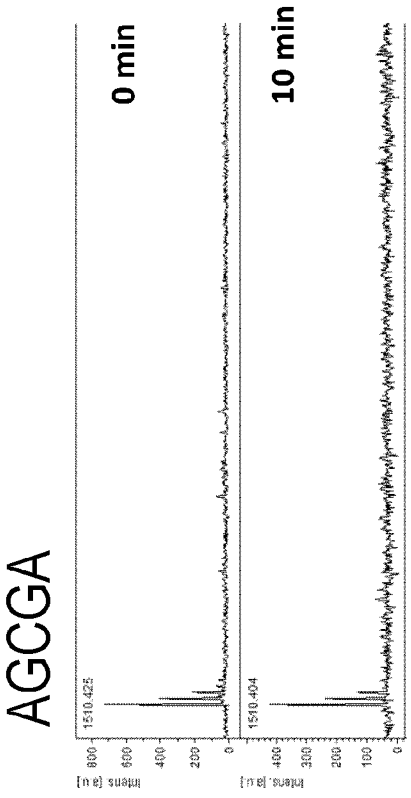
Figure 12C:
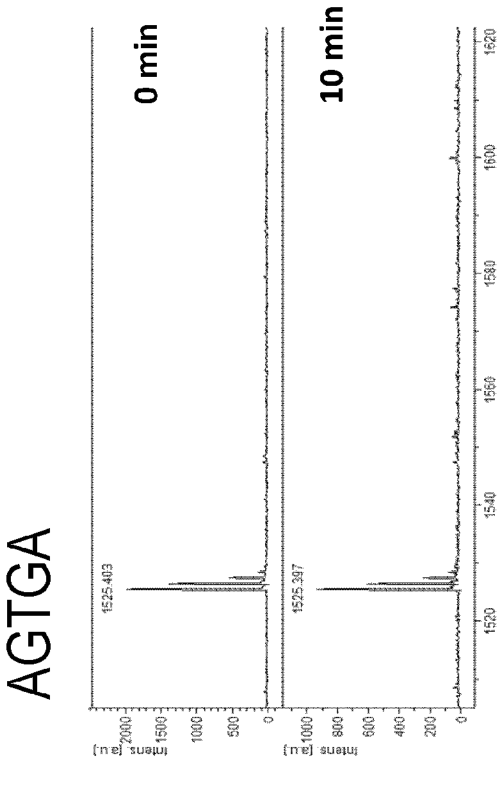

To test the hypothesis, a synthetic DNA 5mer oligo GAXAG (X=5hmC) was treated to screen different BS recipes and conditions, and Maldi TOF MS was used to monitor the reactions. It was found that treatment under ncBS conditions (e.g., pH between 6.8 and 7.2) could convert 5hmC to CMS quantitatively within 3 min at 98° C. (FIG. 11B). Under these conditions, no reaction between cytosine in DNA oligo with BS was observed within 10 min (FIGS. 12A-12C). Other oligos were also tested containing the corresponding T and 5mC and it was found that none of them showed any reaction with BS, suggesting that the reaction of BS with 5hmC under the disclosed conditions is highly efficient and specific.

Figure 13A:
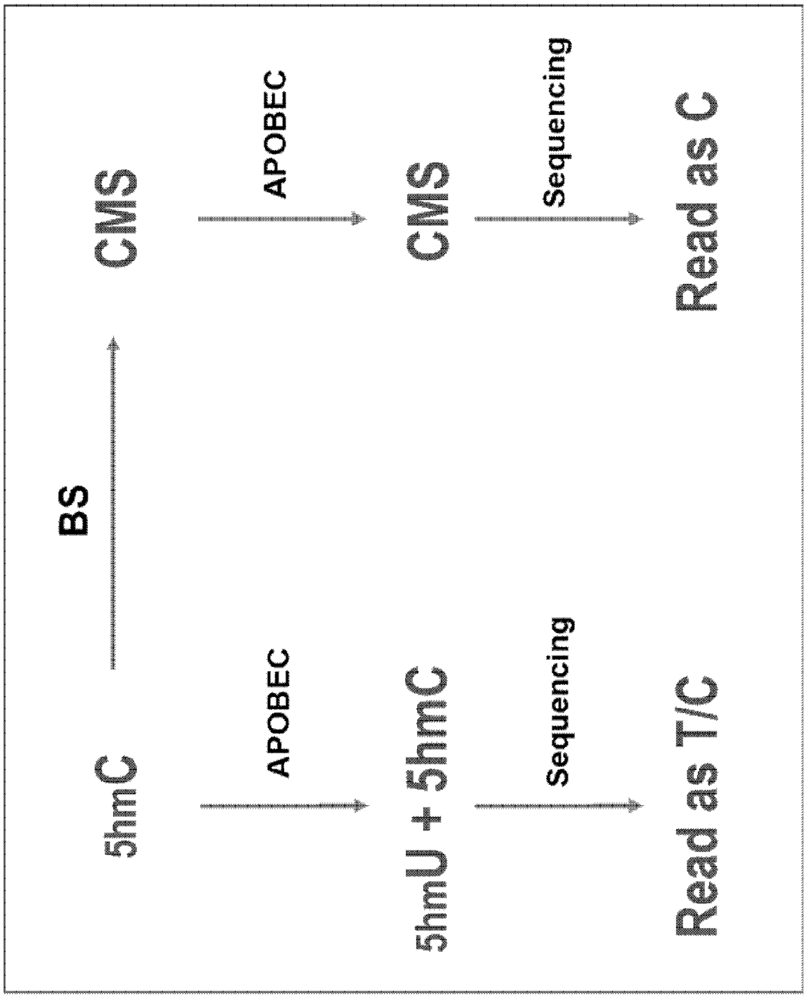
FIG. 13A shows an overview of evaluation of 5hmC to CMS conversion efficiency by Sanger sequencing.
Figure 13B:
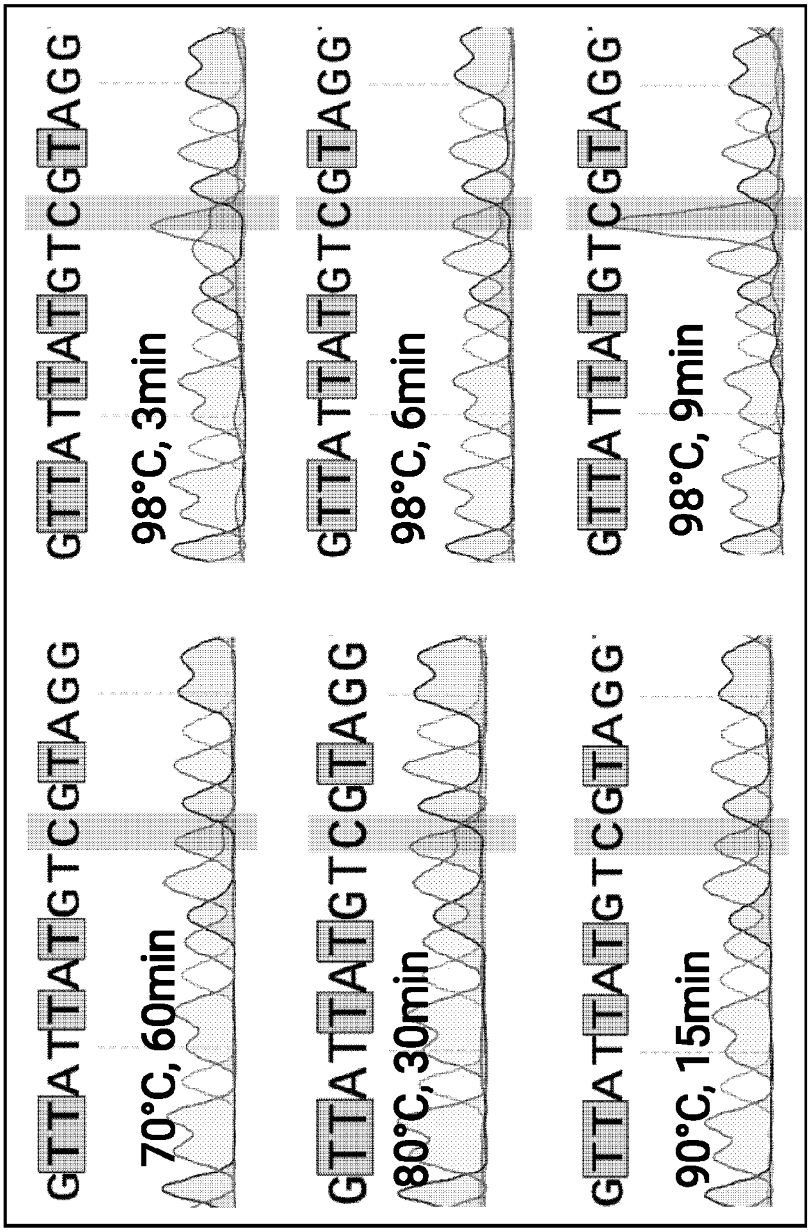
FIG. 13B shows Sanger sequencing results indicating that increased reaction time or temperature enhanced the CMS conversion. At 98° C., 9 min of BS treatment converted the majority of 5hmC sites into CMS.

An APOBEC-assisted Sanger sequencing strategy was then used to measure the conversion rate of 5hmC to CMS in an 82mer DNA oligo containing one 5hmC modification. Since both 5hmC and CMS are read as C in direct Sanger sequencing, direct Sanger sequencing cannot distinguish CMS from 5hmC. However, it was found that APOBEC treatment can partially deaminate 5hmC so that 5hmC will be read as a mixture of C and T, while CMS resists deaminate upon APOBEC treatment completely so that it will be read as C only (FIG. 13A). By testing different combinations of reaction temperature and time, it was found that longer reaction time or higher temperature will increase the conversion rate of 5hmC to CMS. At 98° C. under ncBS conditions, it was found that there was no T signal at 5hmC site after 9 min treatment, suggesting that 5hmC was quantitatively converted to CMS within 9 min. In comparison, conventional BS treatment required 10 min at 98° C., followed by 64° C. for 2.5 h (FIG. 13B).

Figure 14A:
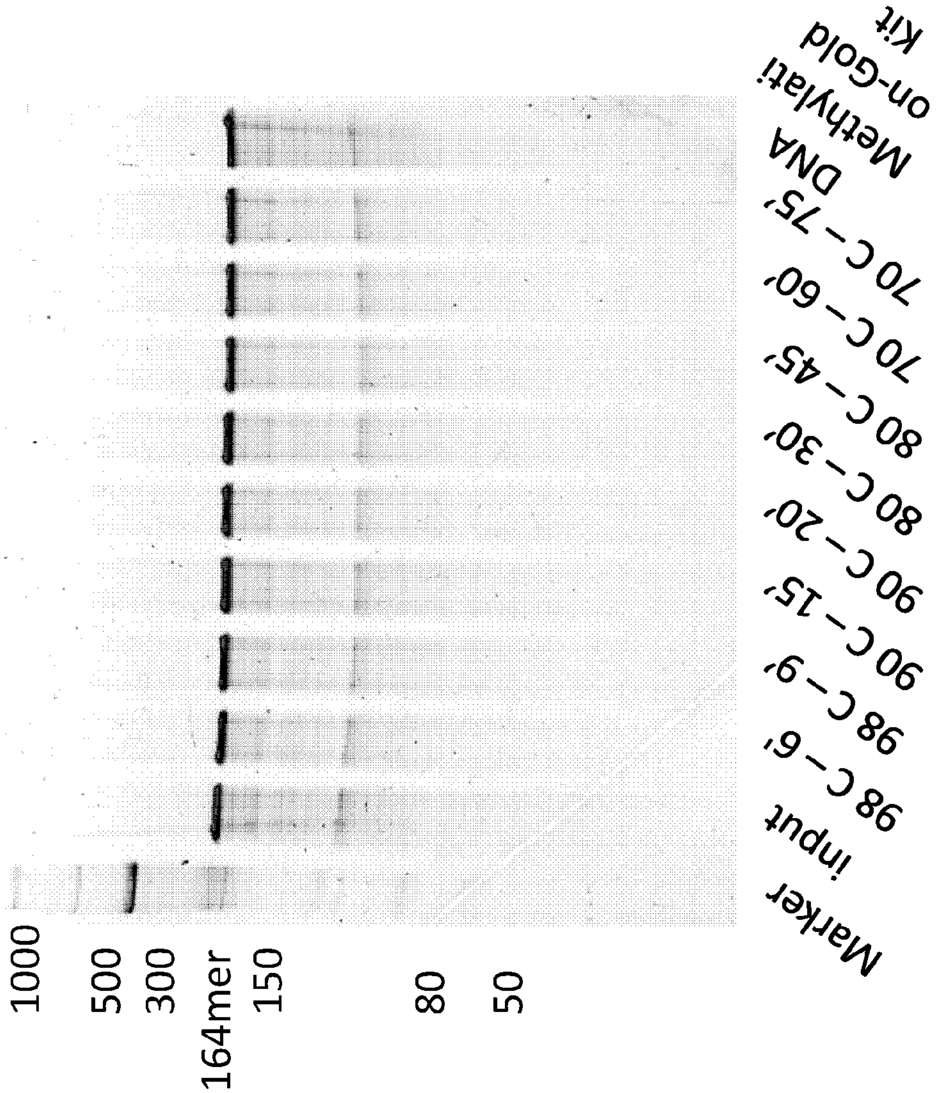
FIGS. 14A-14B show results from comparison of DNA damage between the disclosed non-conventional bisulfite treatment and commercial Zymo Methylation-Gold Kit.
Figure 14B:
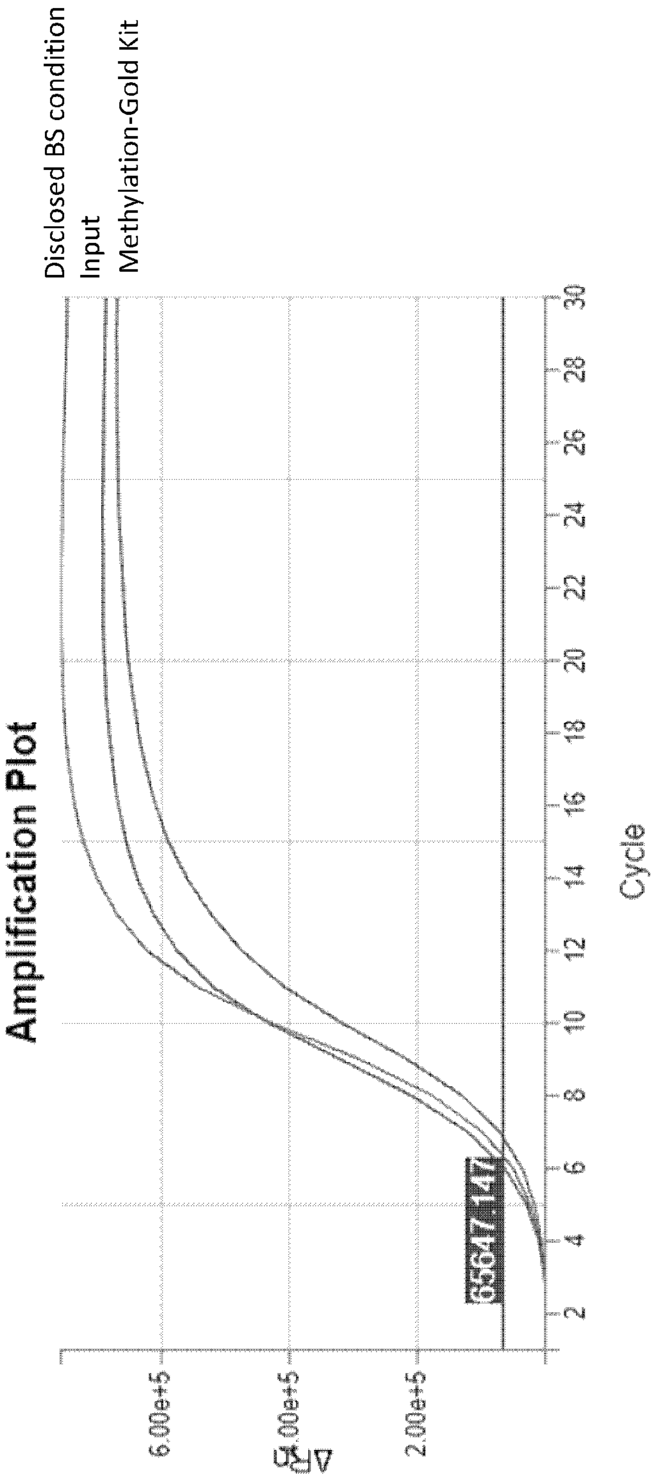

Next the DNA damage caused by the disclosed ncBS conditions was compared to that of the commercially available Zymo kit. To this end, a 164mer DNA oligo was used and treated with the disclosed BS recipe with different time and temperature and then a PAGE gel run to evaluate the DNA damage. It was found that all BS treatments using the disclosed ncBS recipe and conditions gave no DNA degradation while obvious DNA degradation was observed when the same amount of DNA was treated with BS reagents under the conditions suggested in the Zymo commercial kit (FIG. 14A). A qPCR assay was also conducted, in which the same amount of DNA was treated with the disclosed BS reagent or BS reagent from the Zymo kit. qPCR results showed that the Ct value for the disclosed BS conditions was very similar to the untreated sample, while that for the sample treated with Zymo kit gave one more cycle, further confirming that the disclosed BS conditions caused less DNA damage (FIG. 14B).

Figure 15A:
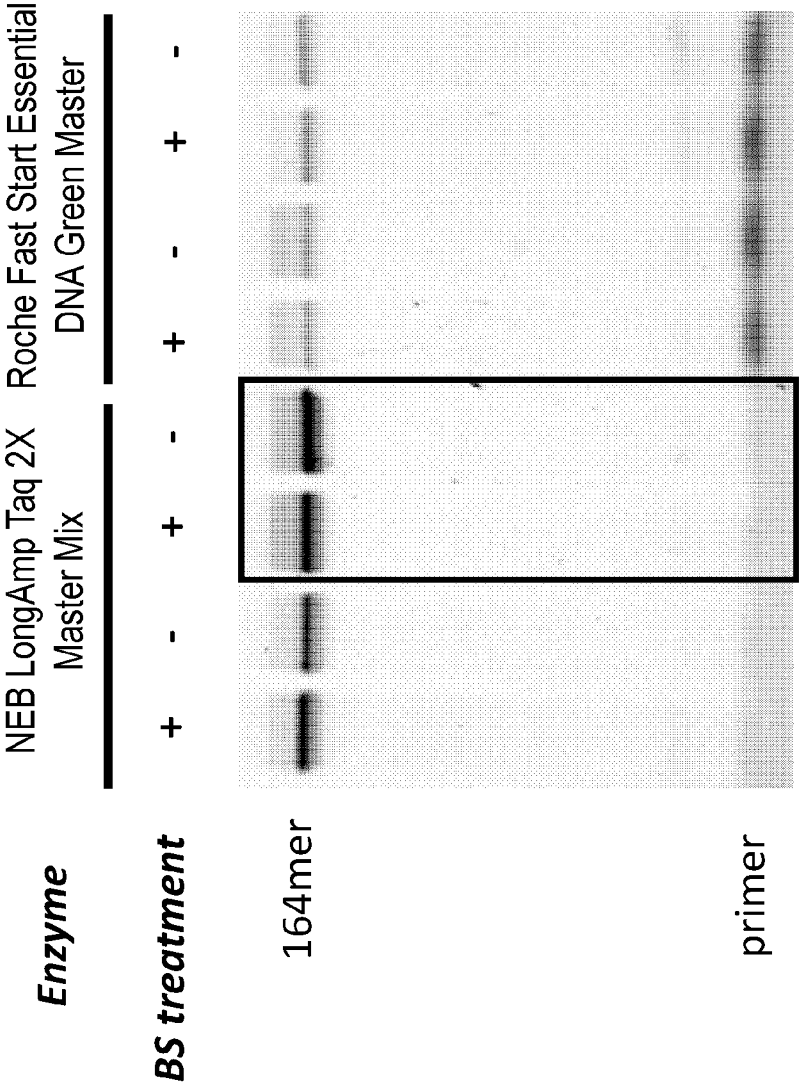
FIGS. 15A-15B show results demonstrating that NEB® LongAmp® Taq Enzyme has the highest efficiency in amplifying the BS treated DNA, as demonstrating by gel electrophoresis (FIG. 15A) and qPCR (FIG. 15B).
Figure 15B:
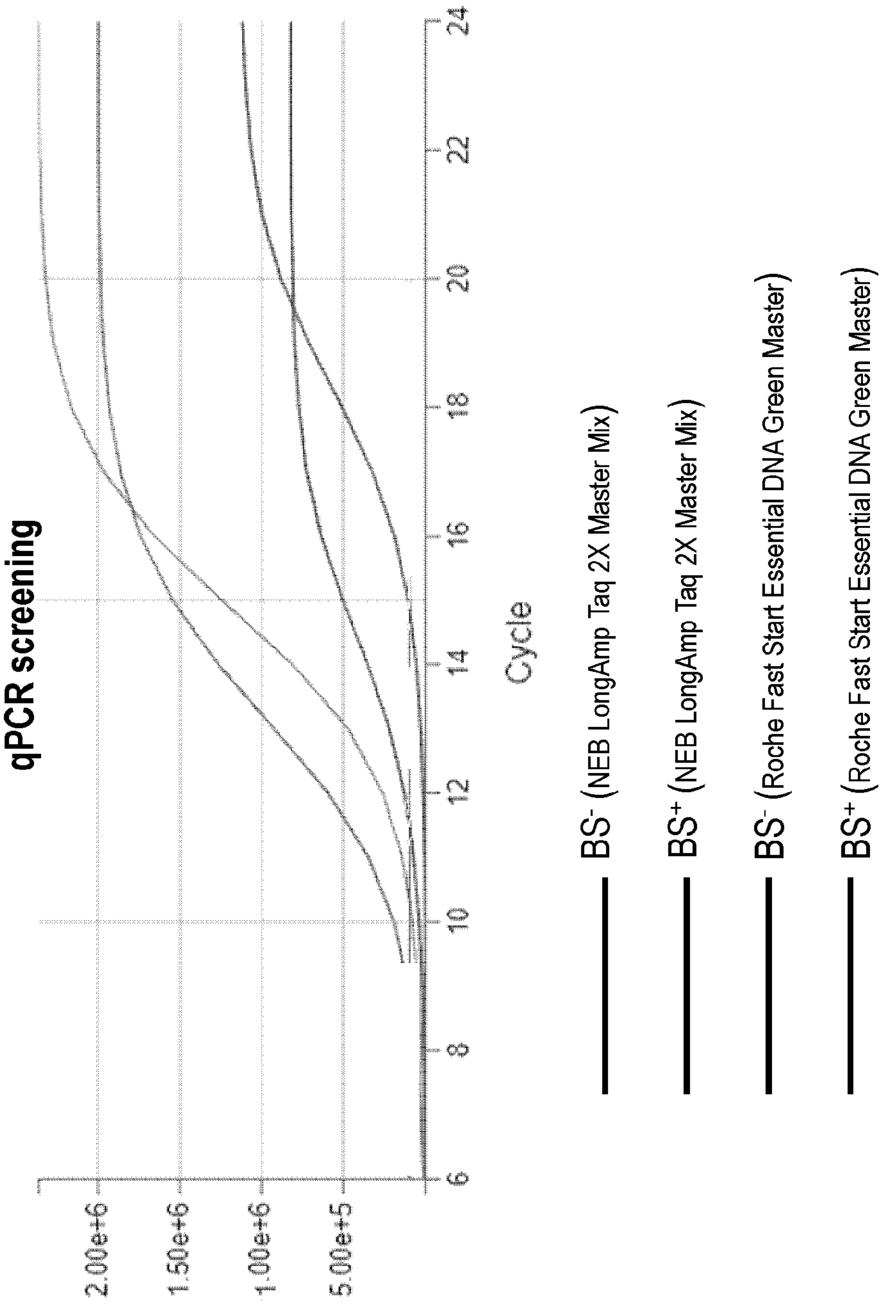

To identify a polymerase capable of efficient CMS read-through, an 82mer DNA oligo containing a CMS site was used to screen all the commercial DNA polymerases, and it was identified that NEB LongAmp DNA polymerase can readthrough CMS efficiently. As shown in FIG. 15A, NEB LongAmp DNA polymerase can readthrough CMS with very high efficiency similar to 5hmC and 5mC to give much more product than using Roche DNA polymerase (FIG. 15A). qPCR results gave similar results as well (FIG. 18B). For the same amount of DNA containing a CMS site, the Ct value using NEB LongAmp taq DNA polymerase was 4 cycles less than that using Roche DNA polymerase.

Figure 16A:
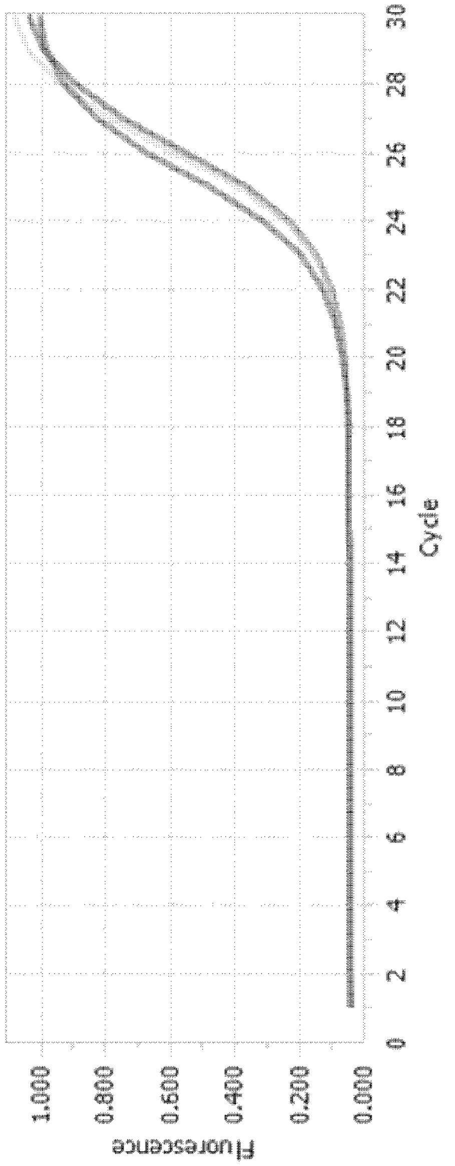
FIGS. 16A-16C show results from analysis of the specificity of use of the anti-CMS antibody.
Figure 16B:
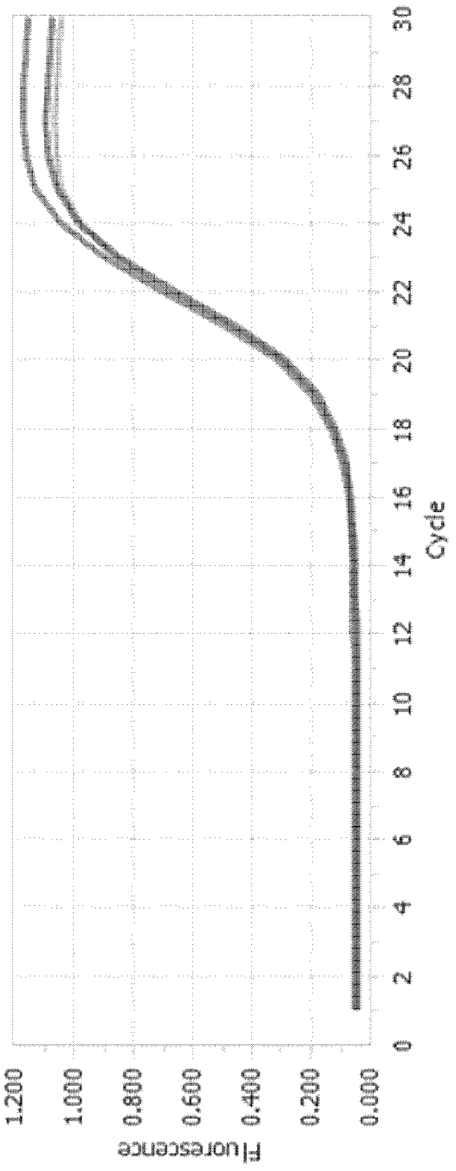
Figure 16C:
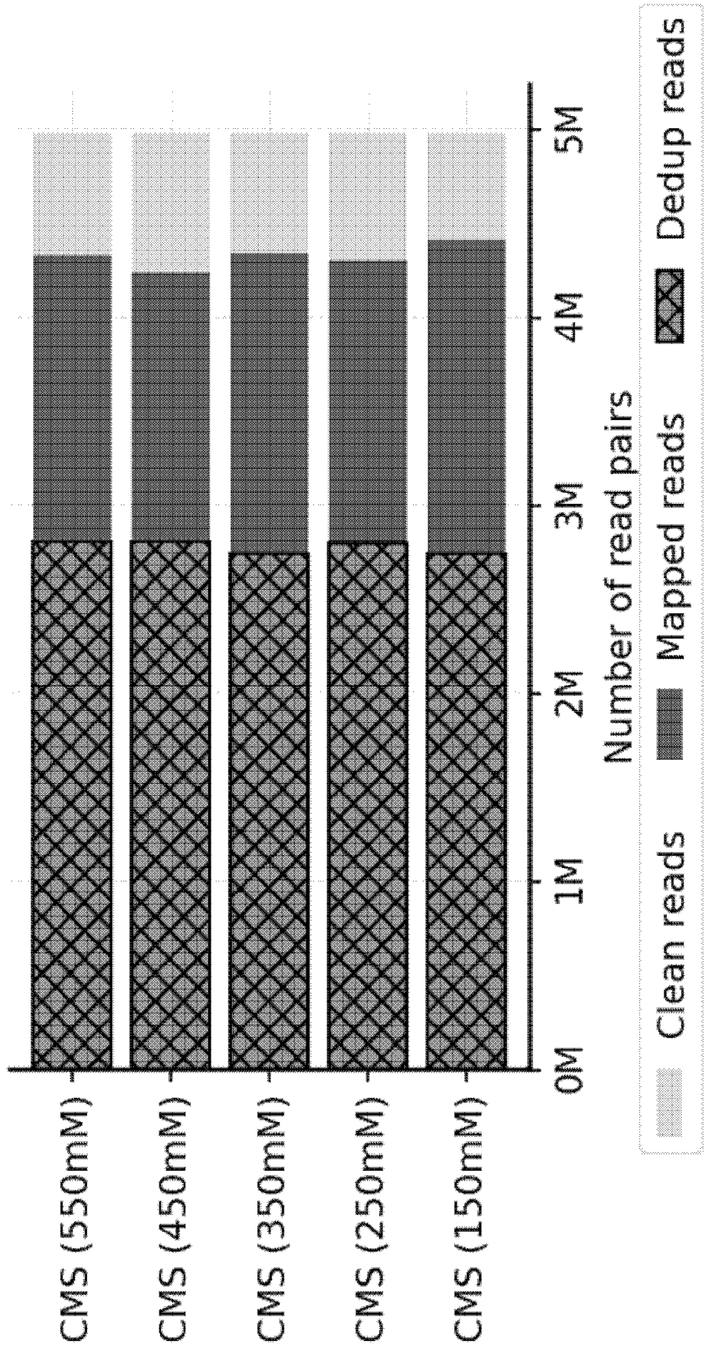

After establishing the effective BS treatment recipe and conditions, and identifying a DNA polymerase capable of reading through CMS efficiently, next the washing conditions after anti-CMS-antibody binding with CMS were optimized. To remove the non-specific binding as much as possible to reduce the background and improve the enrichment efficiency, a higher salt wash step is desirable. After pulldown, the beads were divided equally into five parts and washed each part with buffer containing different NaCl concentrations from 150 to 550 mM. After washing, the beads were heated to 98° C. to release the DNA from the antibody and qPCR assay used to evaluate the amount of DNA recovered. It was found that in all cases, the Ct value remained 22 cycles in the case of CMS, suggesting that anti-CMS antibody binds CMS very tightly and can survive very stringent wash even with 550 mM salt concentration (FIG. 16B), and changing the salt concentration in washing buffer has only a minimal effect on mapping ratio (FIG. 16C). In comparison, when the same amount of DNA containing 5hmC (without BS treatment to convert to CMS) and anti-CMS antibody was used to do the same experiment, it was found the Ct value was 26-27, and became even greater when higher salt concentration was used, suggesting that anti-CMS antibody binds with 5hmC much weaker than anti-CMS antibody binds CMS and thus could not bear more stringent wash conditions (FIG. 16A).

Figure 17:
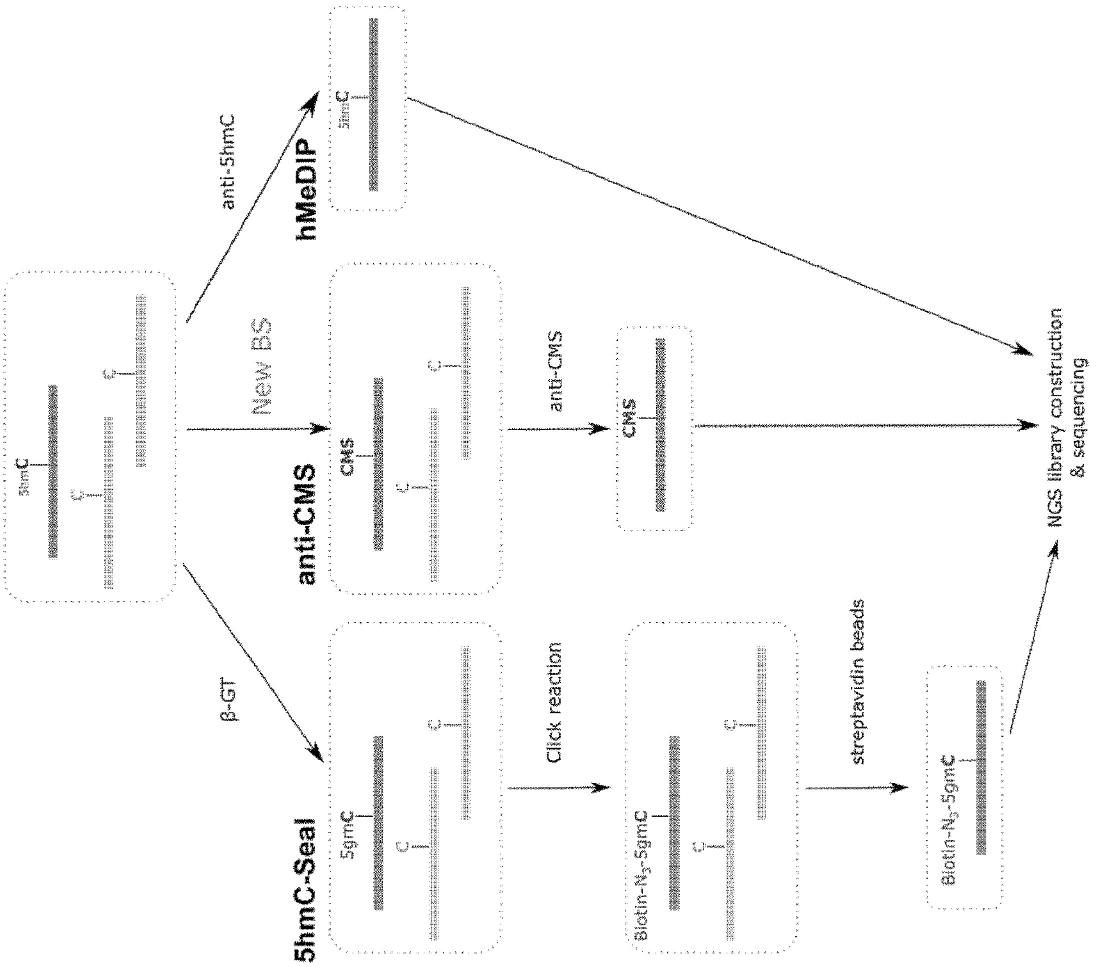
FIG. 17 shows a schematic of a comparison of the disclosed anti-CMS method with other 5hmC analysis methods.
Figure 18:
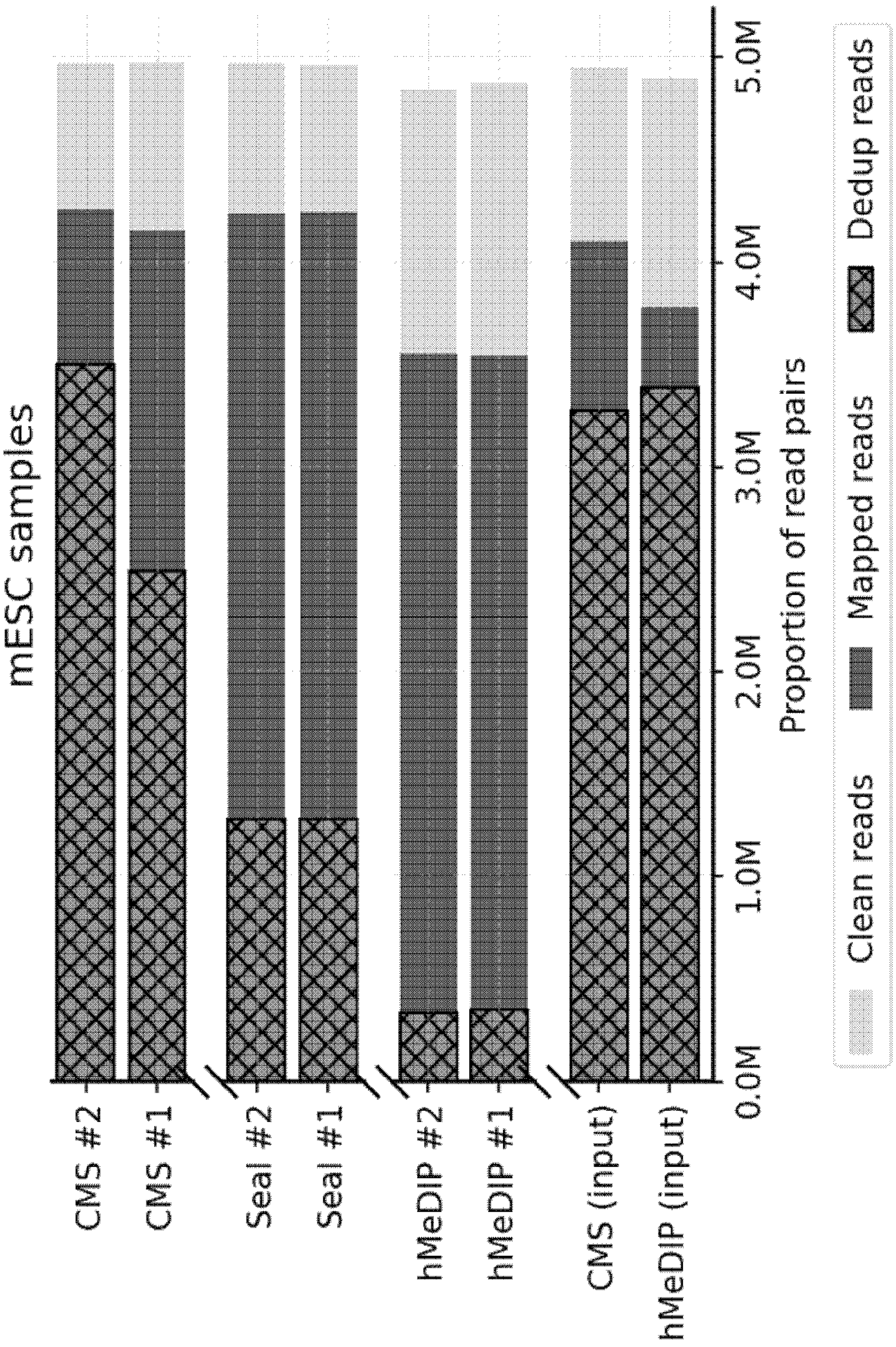
FIG. 18 shows results comparing the mapping ratio and duplicate ratio of the three 5hmC analysis methods: the disclosed methods ("CMS"), hMeDIP, and 5hmC-Seal ("Seal").
Figure 19:
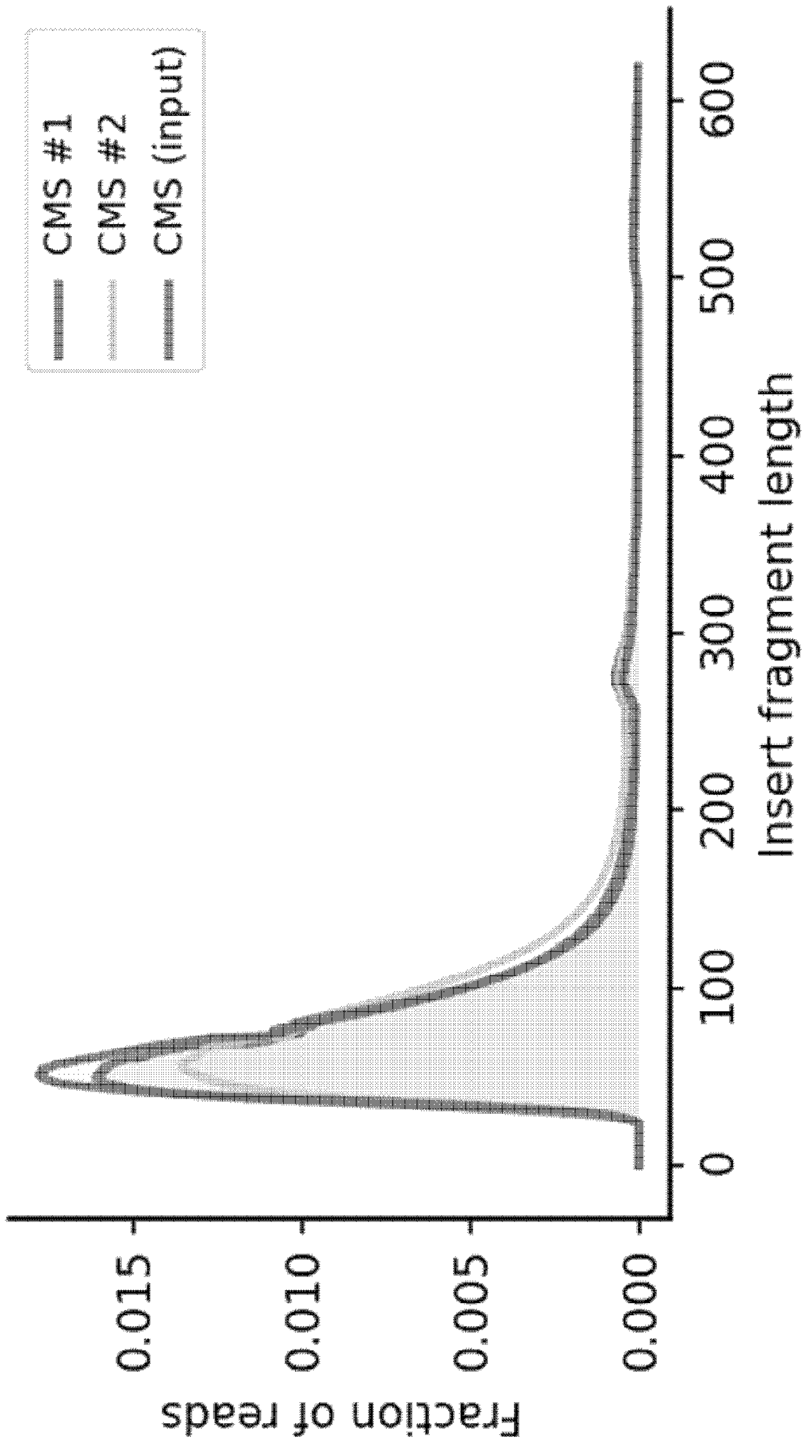
FIG. 19 shows results demonstrating that insert fragment of BS treated libraries are similar to the input library, suggesting that BS treatment did not cause obvious DNA degradation.
Figure 20A:
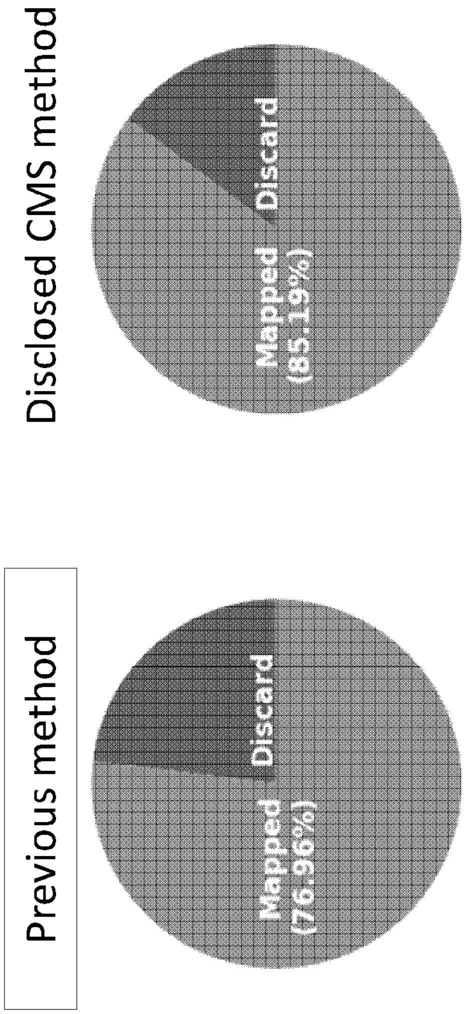
FIGS. 20A-20B shows results from comparison of the disclosed CMS method to the method disclosed in Huang et al. (*PLoS ONE*. 5:e8888, (2010)
Figure 20B:
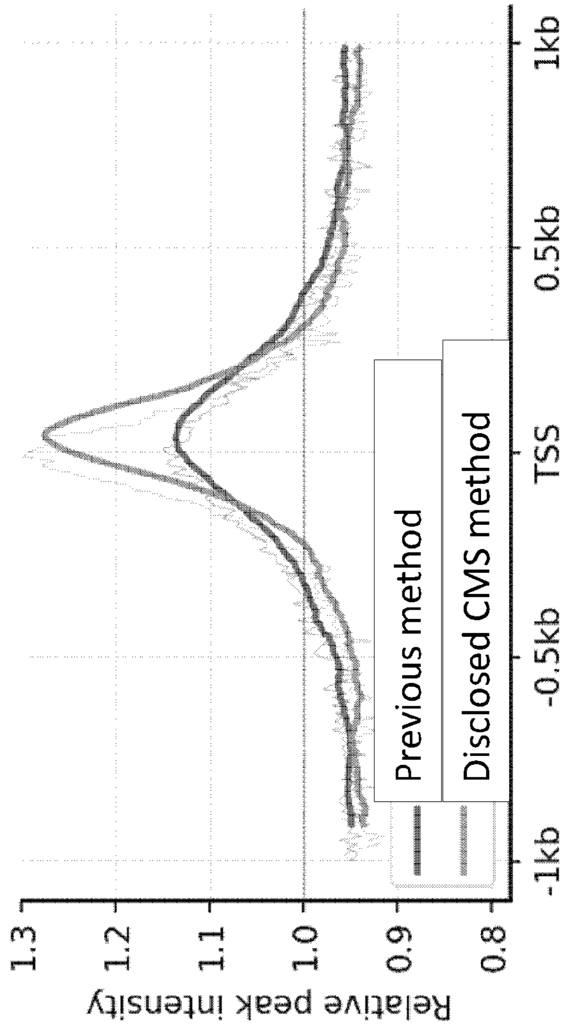

The inventors then tried to build libraries starting from a low amount of starting DNA (50 ng mES gDNA) to compare hMeDIP, 5hmC-Seal and the disclosed ncBS/anti-CMS antibody ("anti-CMS") methods in parallel. FIG. 17 shows the workflow of the three methods. Then, the mapping ratio and PCR duplicate ratio were evaluated by high throughput sequencing. To do this comparison, the sequencing data was randomly subsampled for each library into equal amounts (5 M reads). Both anti-CMS and 5hmC-Seal yielded approximately 85% mapping ratio compared to the 75% of hMeDIP method. Unique mapping ratio of anti-CMS method (~70%) is higher than the 30% of 5hmC-Seal and 10% of the hMeDIP method (FIG. 18). Insert fragment of CMS libraries were similar to the input library, suggesting that the new BS treatment did not cause obvious DNA degradation (FIG. 19). Compared with the original CMS method using conventional BS conditions, the disclosed new CMS libraries showed higher mapping ratio than the data extracted from Huang et al. (PLoS ONE. 5:e8888, (2010), incorporated herein by reference in its entirety) due to the lower complexity generated by their BS treatment (FIG. 20A). More importantly, the new CMS method also showed higher efficiency. Enrichment signal near the TSS (Transcription Starting Sites) showed the same distribution pattern but higher signal than that in the original CMS method of Huang et al. (FIG. 20B).

Figure 21:
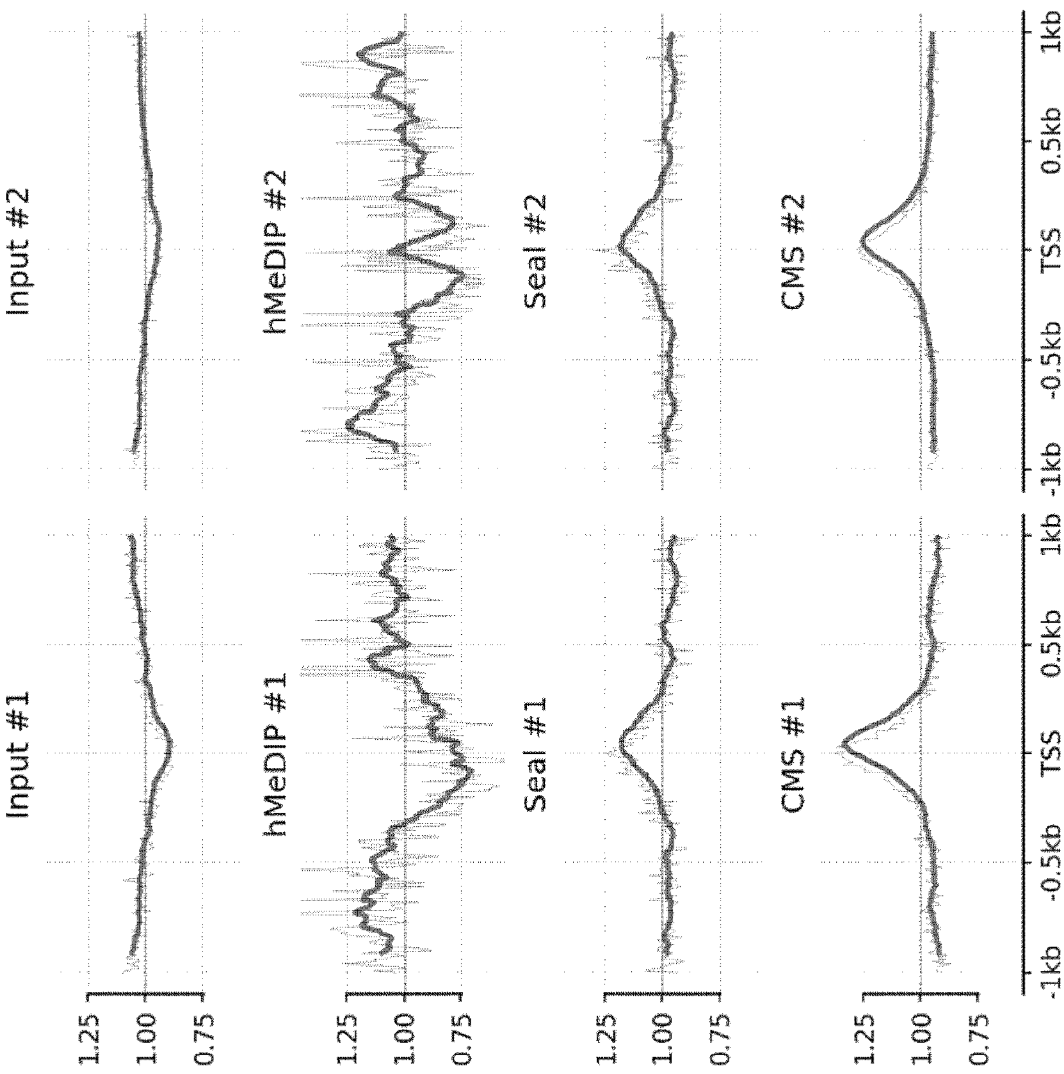
FIG. 21 shows results demonstrating that the disclosed CMS methods also show higher enrichment near the transcription start site (TSS) than 5hmC-Seal and hMeDIP methods.
Figure 22:
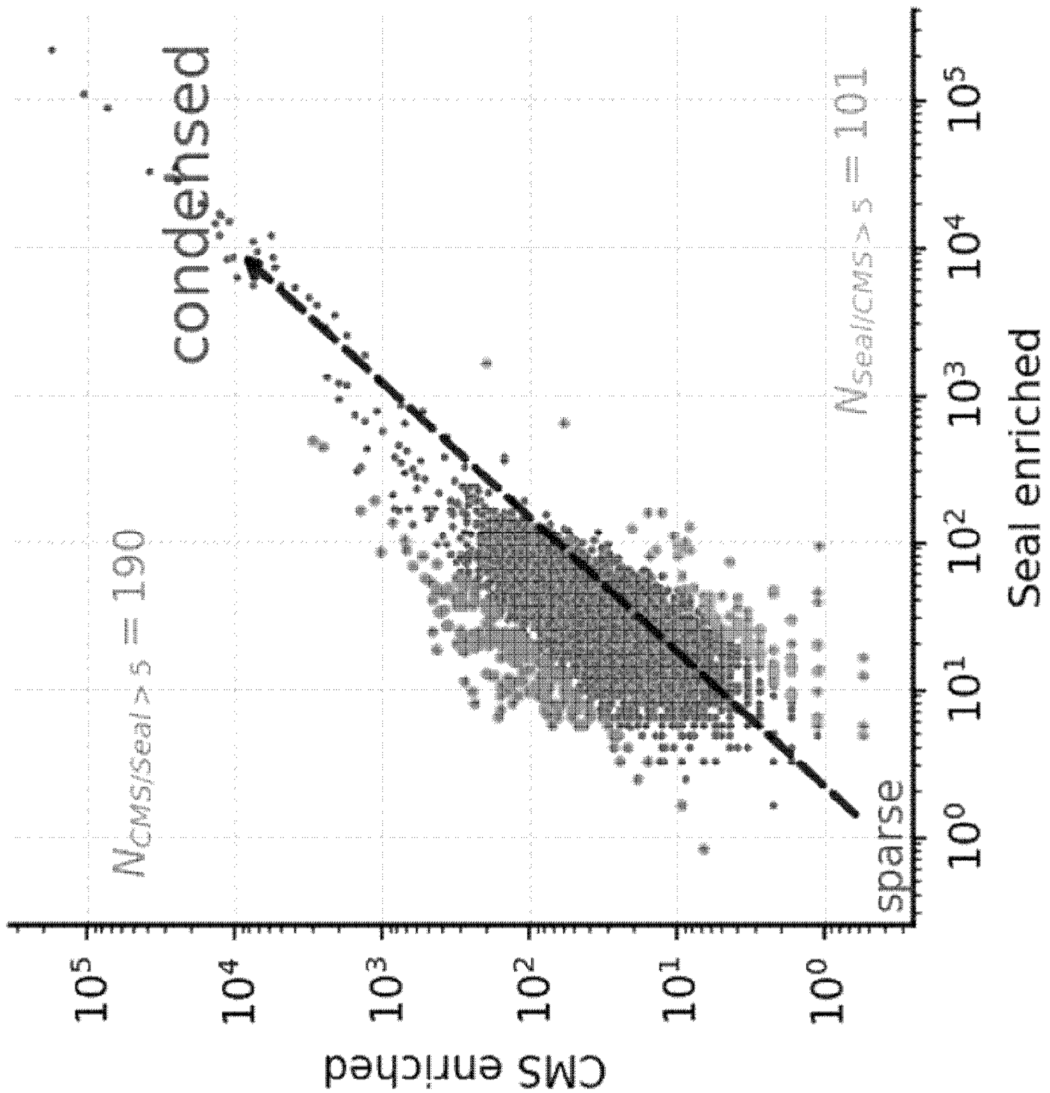
FIG. 22 shows a dot plot comparing the enrichment profile of the new CMS method and that of the 5hmC-Seal method.
Figure 23A:
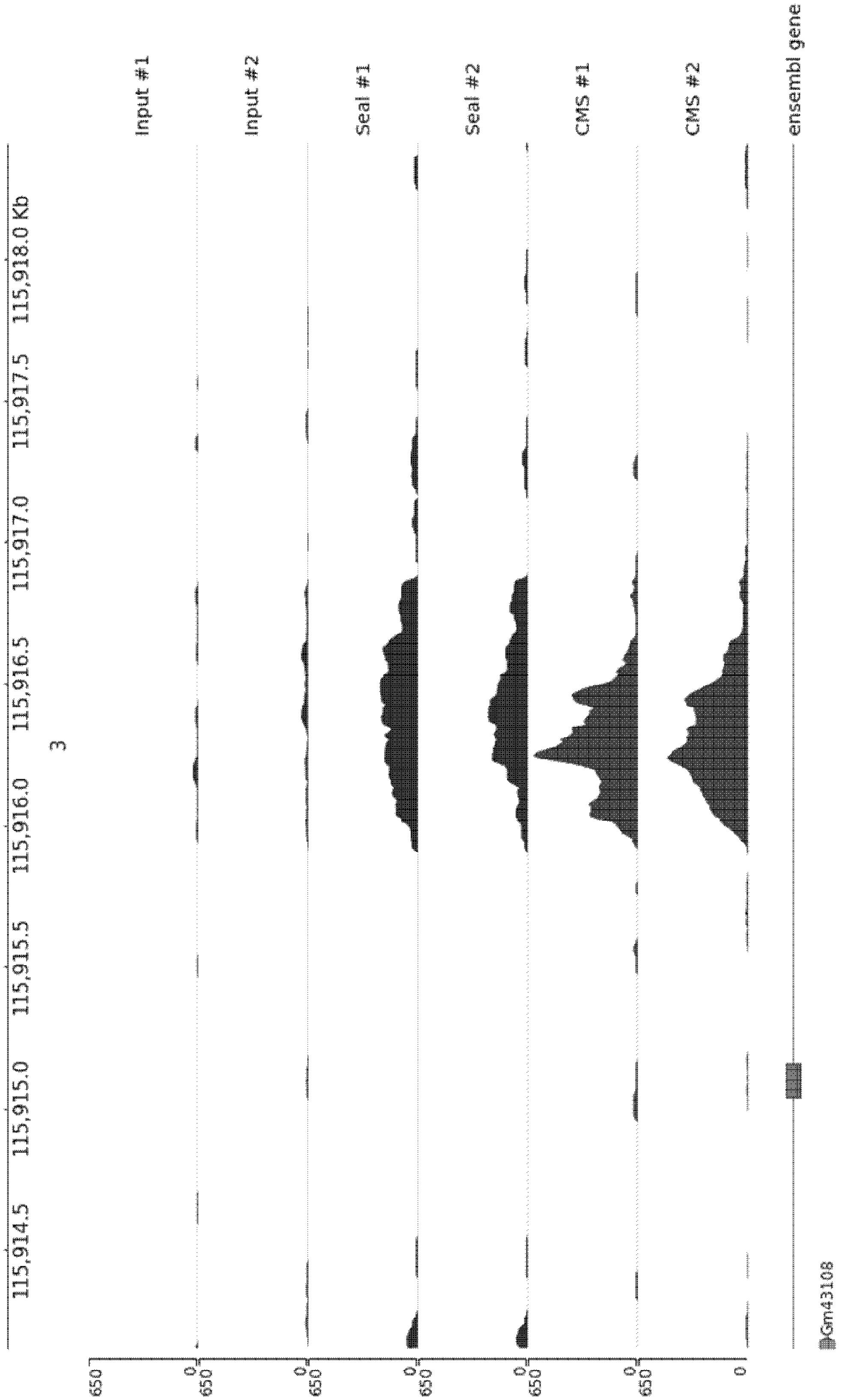
FIGS. 23A-23D show four example regions in the mouse genome, highlighting enrichment in each region using the different techniques.
Figure 23B:
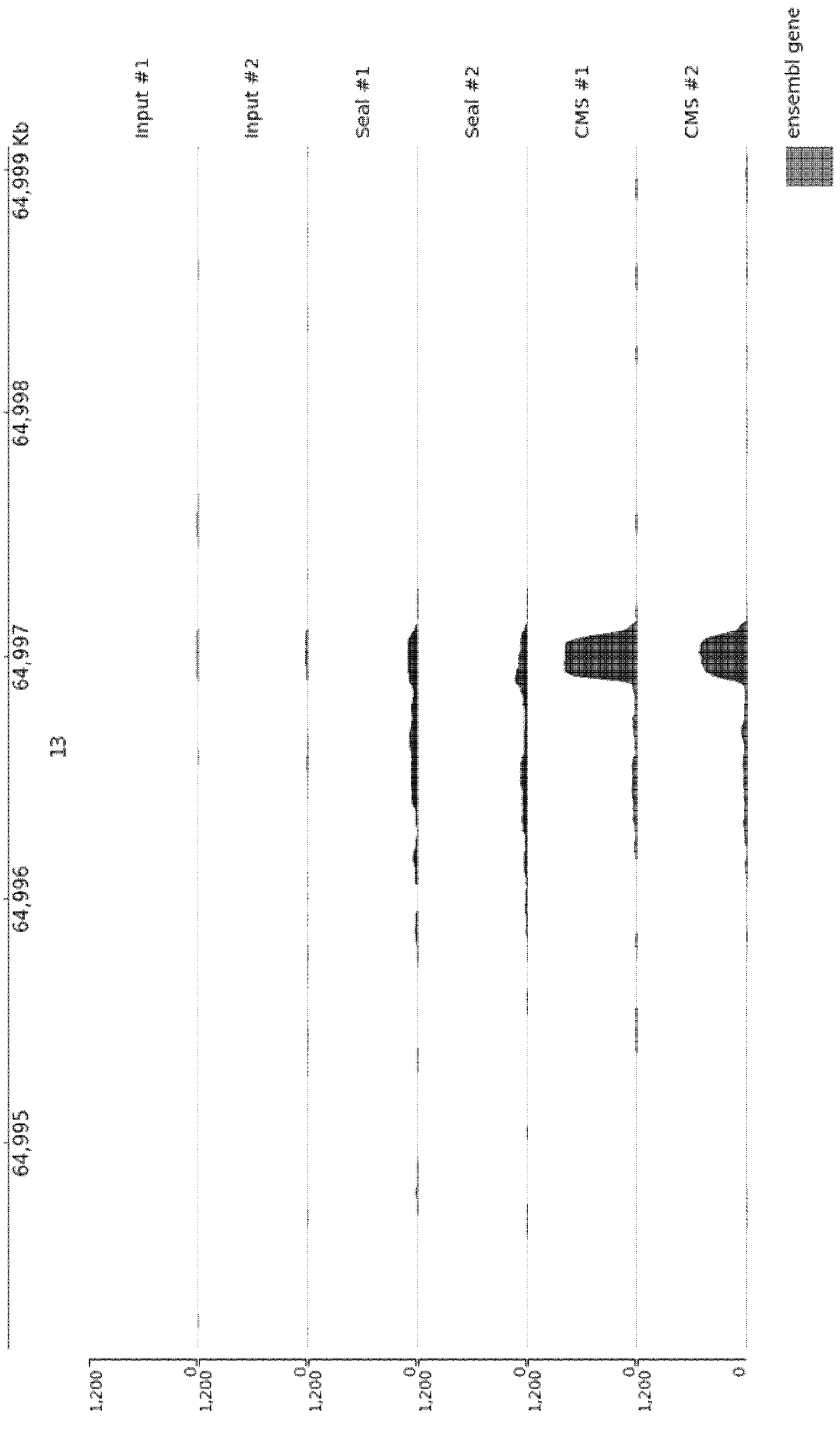
Figure 23C:
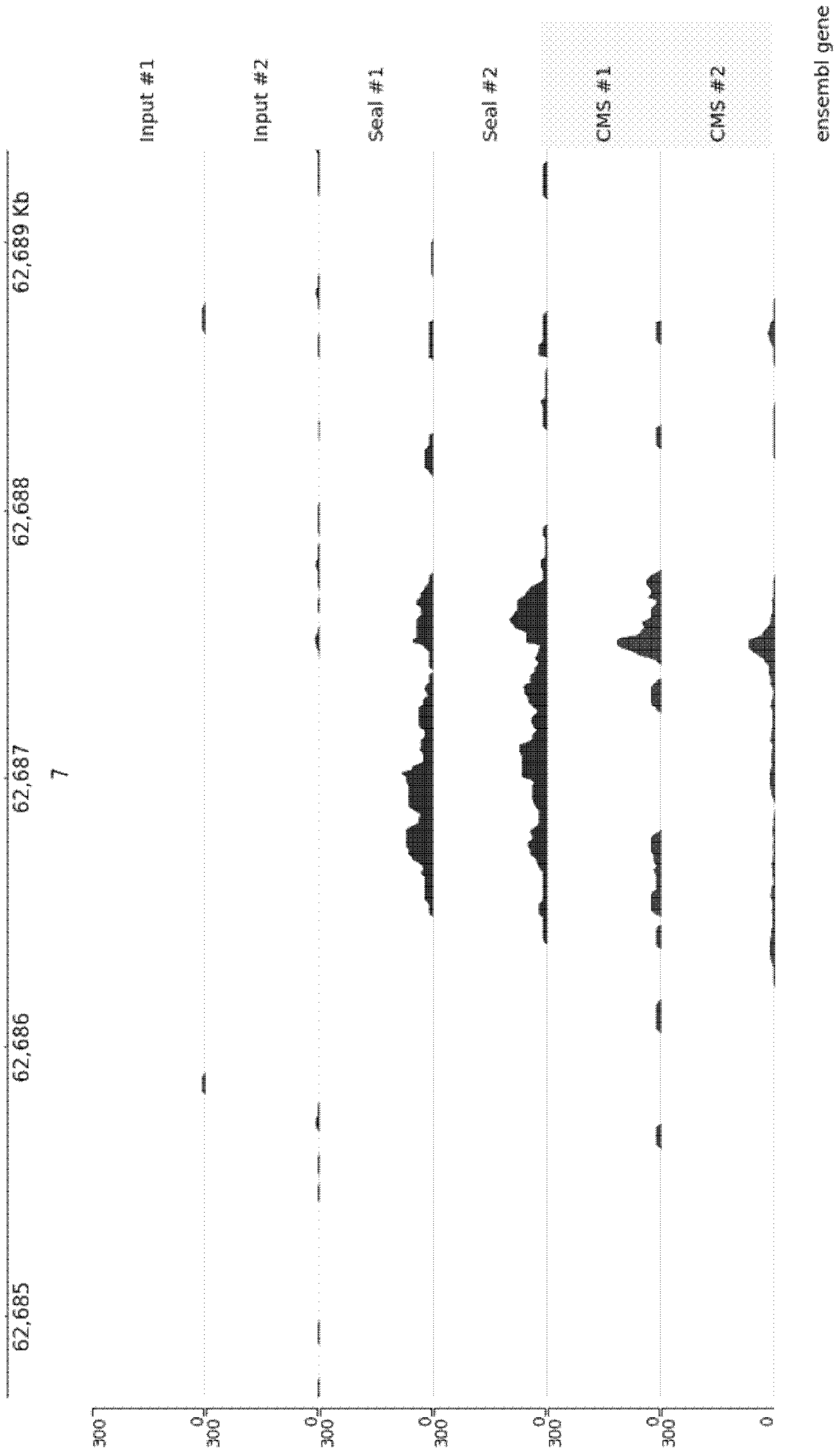
Figure 23D:
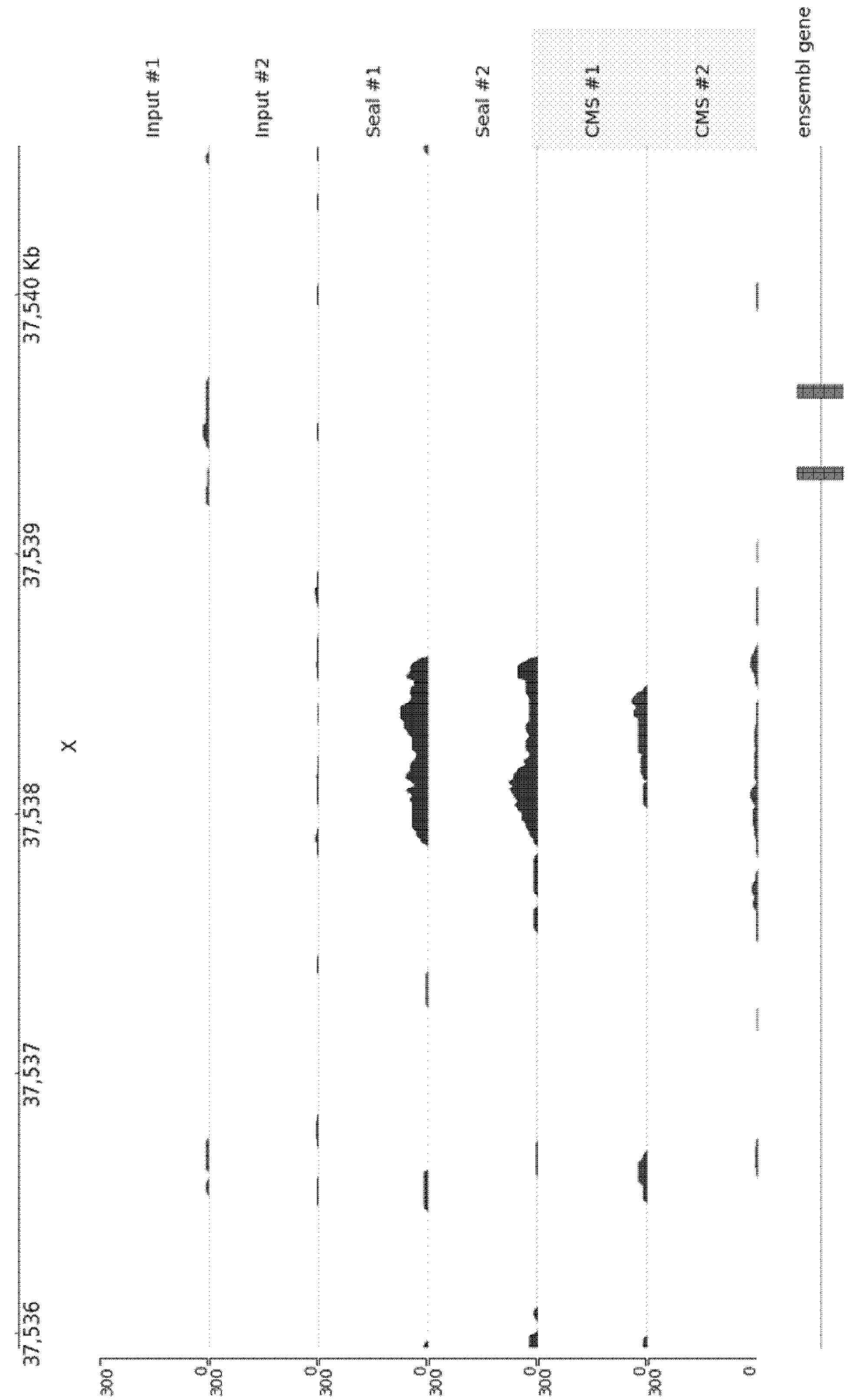

Enrichment signal near the TSS was also calculated for the hMeDIP and 5hmC-Seal libraries. By comparison, it was found that anti-CMS enrichment was slightly better than the 5hmC-Seal method, but much better than the hMeDIP methods (FIG. 21). Principal component analysis (PCA) indicated that different pulldown method favors different 5hmC profile (FIG. 22). To investigate the differences between anti-CMS and 5hmC-Seal, the enrichment score observed for each matched peak from the two methods was compared (FIG. 22). High enrichment peaks (5hmC enriched regions) showed higher enrichment scores in the anti-CMS library, while low abundance peaks (5hmC sparse regions) showed higher enrichment scores in the 5hmC-Seal library. Based on analysis of the read coverage in some representative regions (FIGS. 23A-23D), the disclosed new CMS method enriched regions that are more condensed in 5hmC distribution, while 5hmC-Seal method enriched peaks that are sparser in 5hmC distribution.

Figure 24:
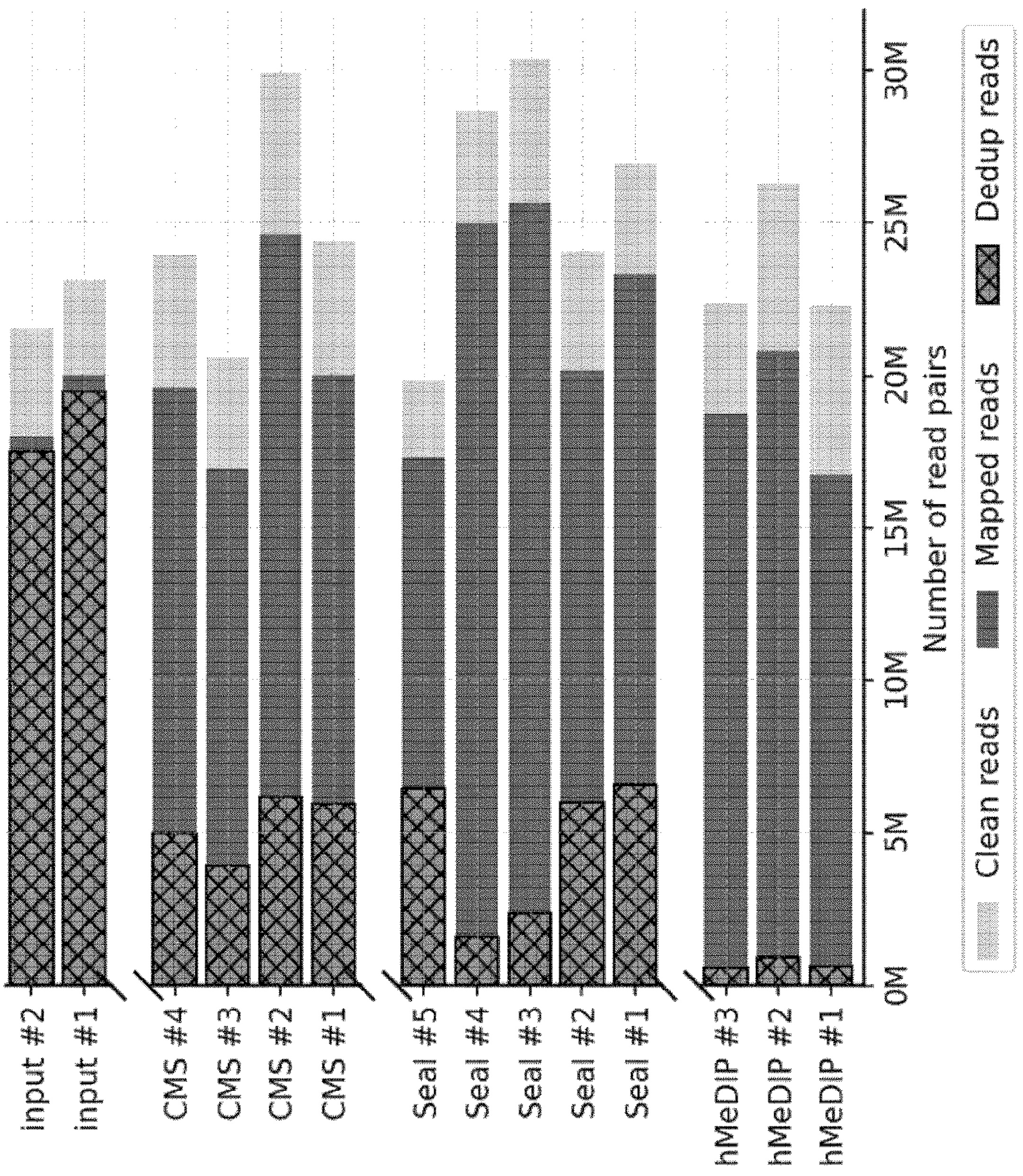
FIG. 24 shows data demonstrating that the disclosed new CMS method is more robust in pulldown efficiency for cfDNA (low input samples).
Figure 25:
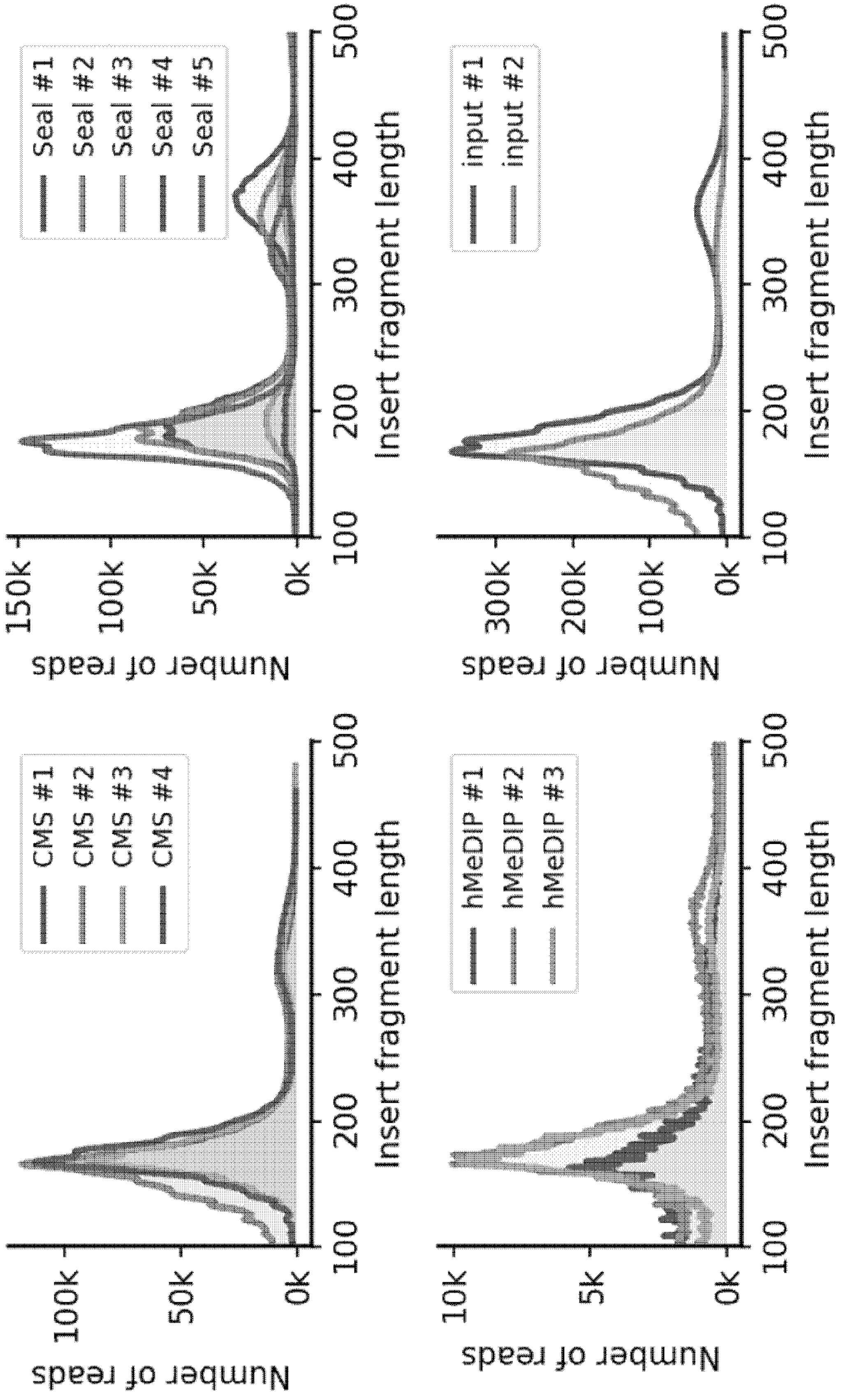
FIG. 25 shows insert fragment size distribution for each sample as analyzed by each of the shown analysis methods.
Figure 26:
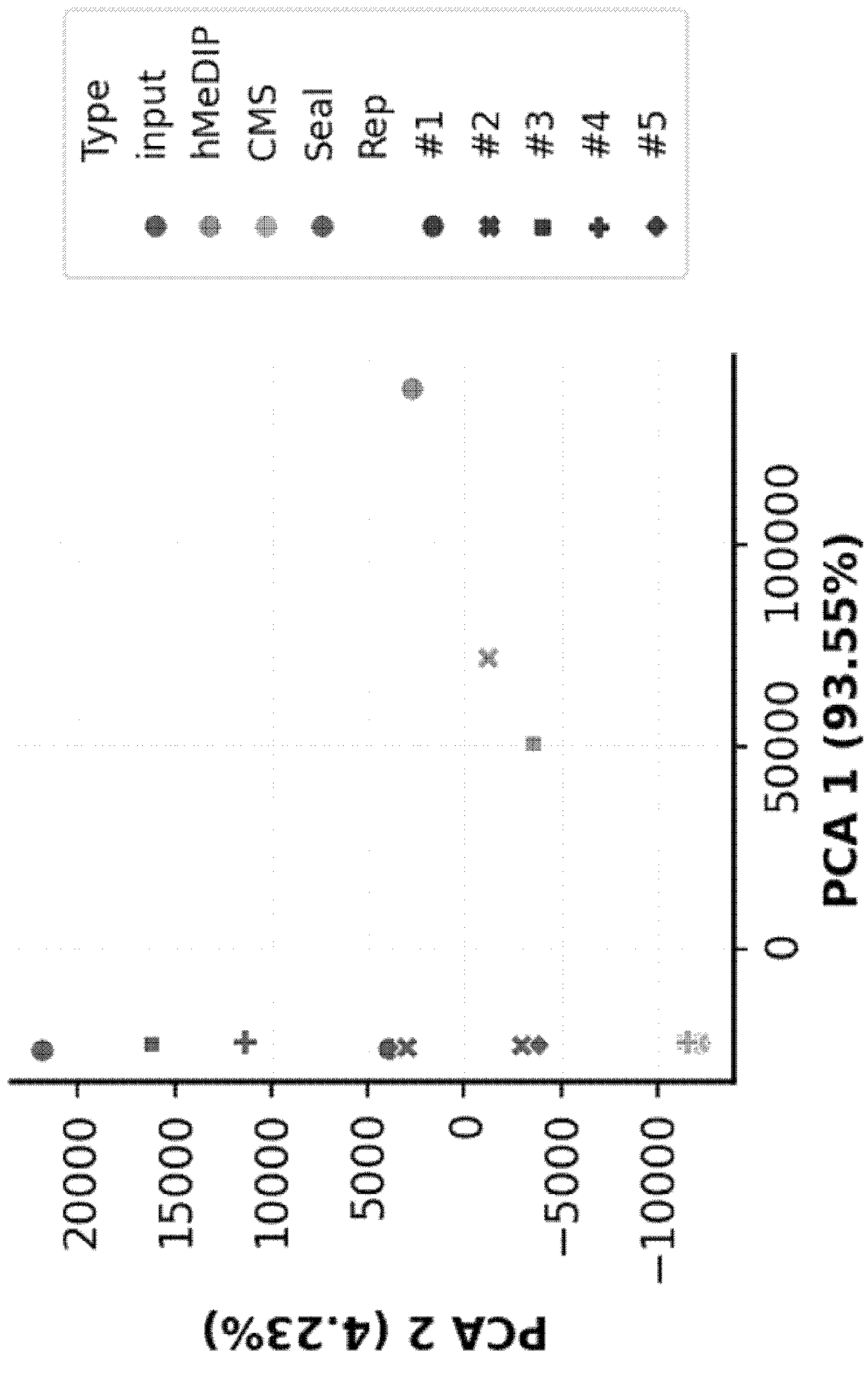
FIG. 26 shows a PCA analysis using all 5hmC peaks, demonstrating that the disclosed new CMS method was more robust than 5hmC-Seal and hMeDIP method, and showed unique profile compared to the input libraries.
Figure 27:
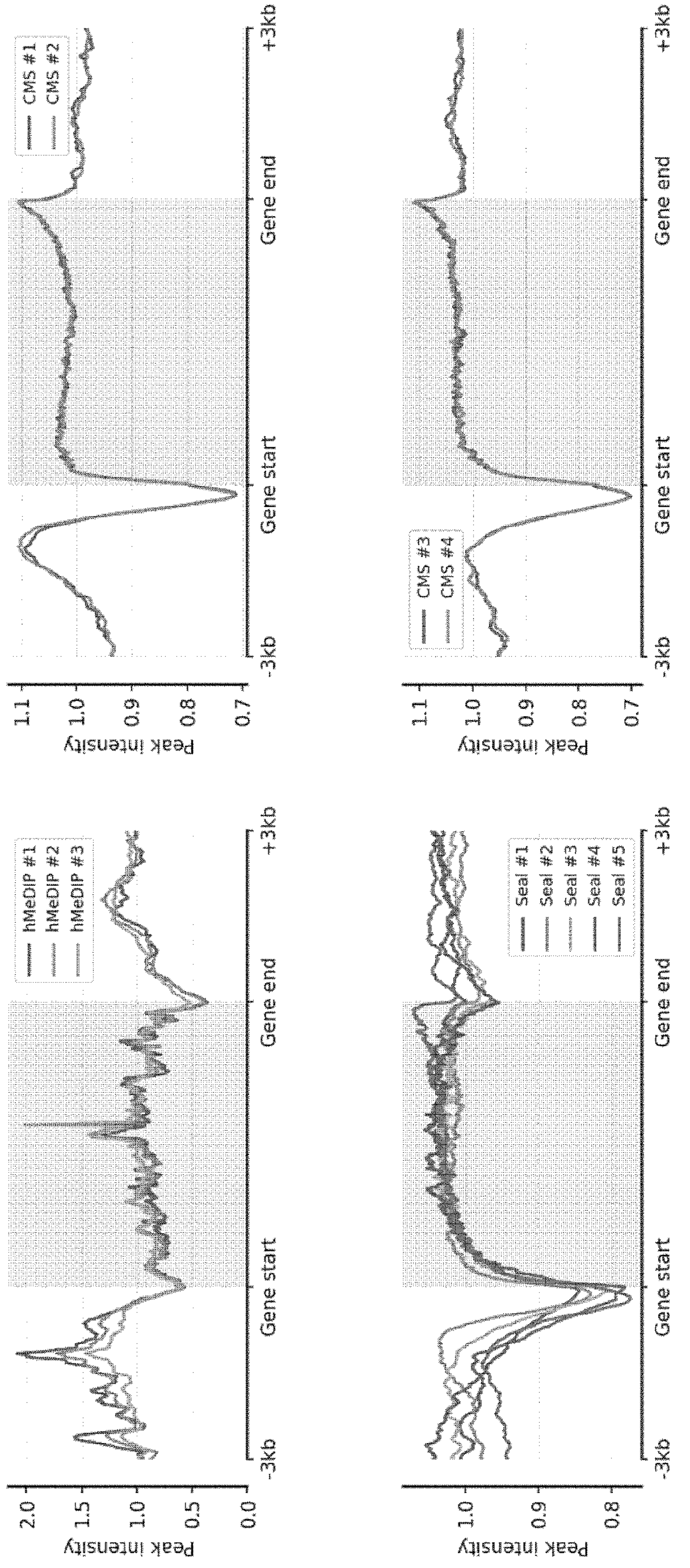
FIG. 27 shows results demonstrating that hMeDIP, 5hmC-Seal and new CMS method showed different metagene profile. CMS #1 and CMS #2 are two technical replicates of the healthy plasma donor. CMS #3 and CMS #4 are two technical replicates of a cancer patient.
Figure 28:
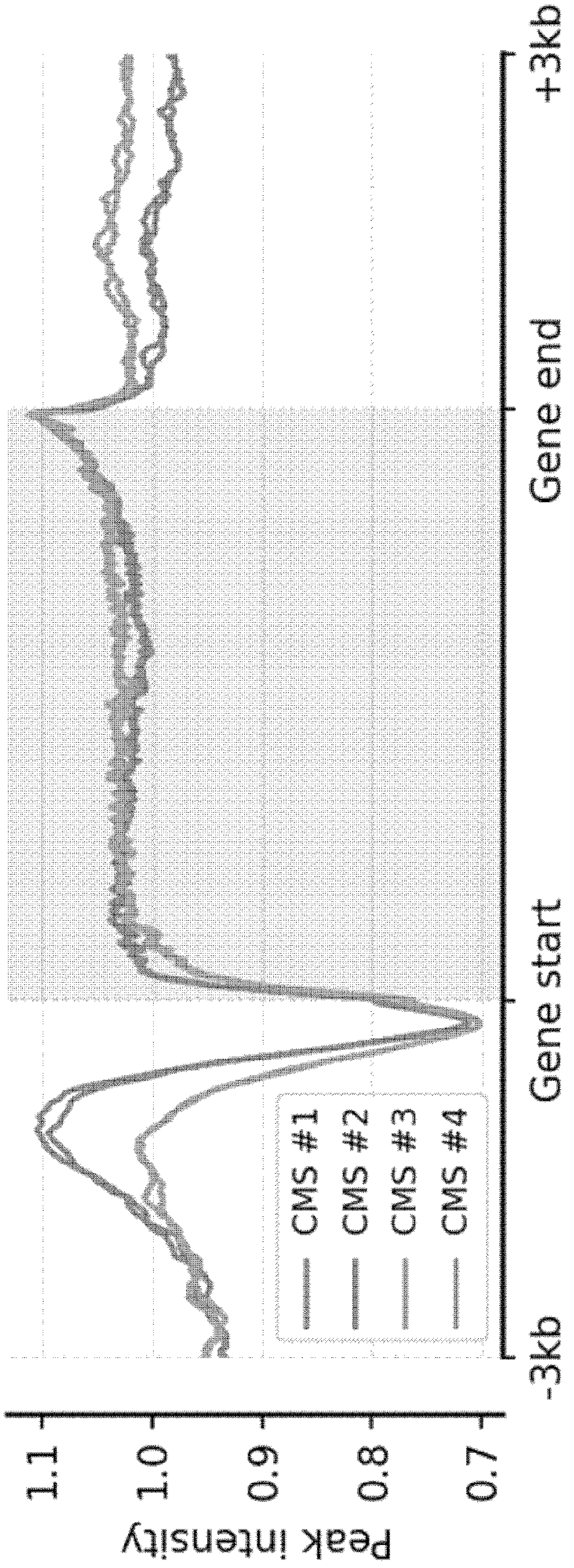
FIG. 28 shows results demonstrating that the disclosed new CMS method can distinguish different biological samples. CMS #1 and CMS #2 are two technical replicates of the healthy plasma donor. CMS #3 and CMS #4 are two technical replicates of a cancer patient.
Figure 29:
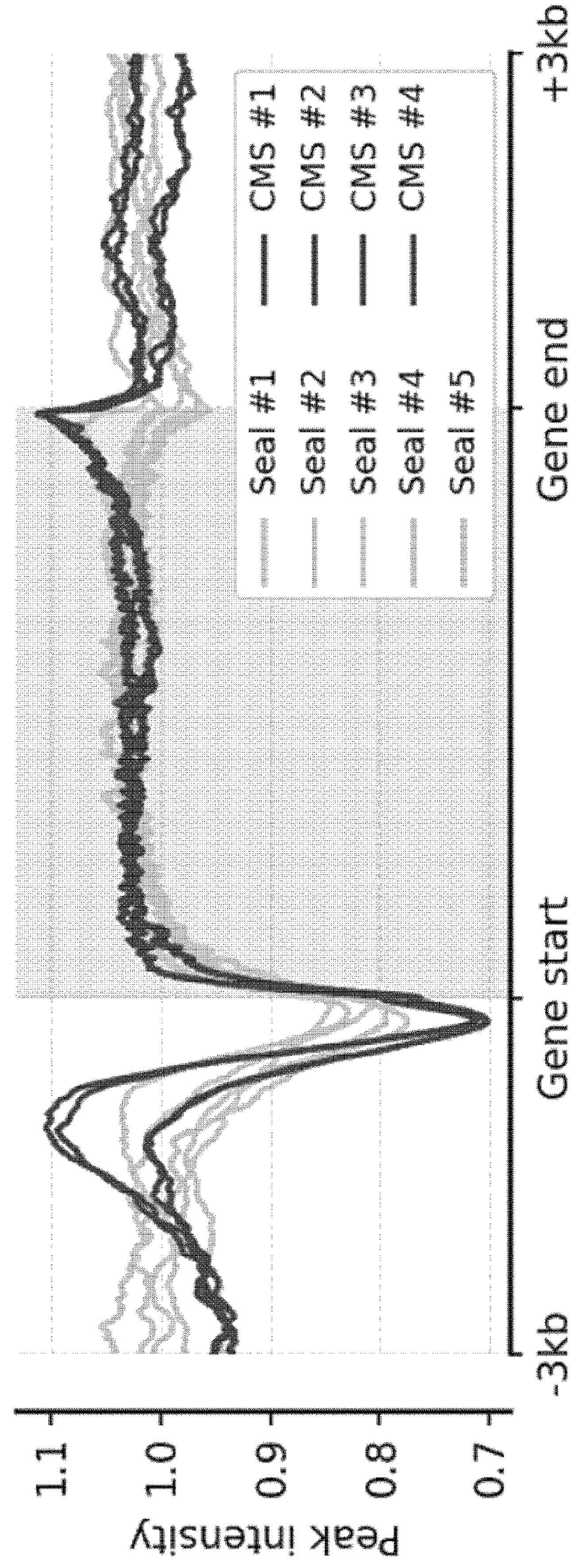
FIG. 29 shows results demonstrating that the new CMS method can capture 5hmC signal near the transcript end sites (TES).
Figure 30:
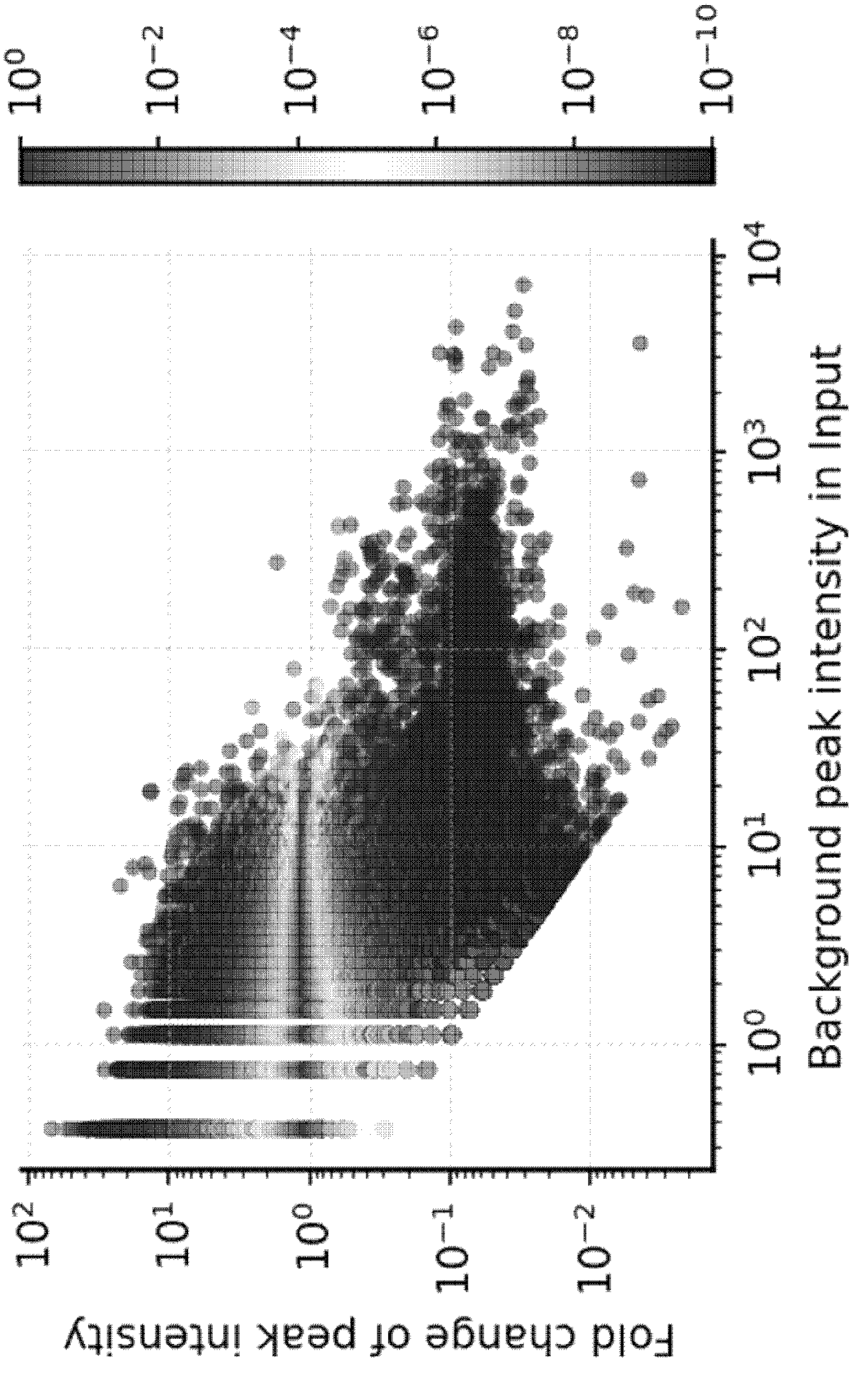
FIG. 30 shows fold change (y axis) of 5hmC enriched peaks.
Figure 31A:
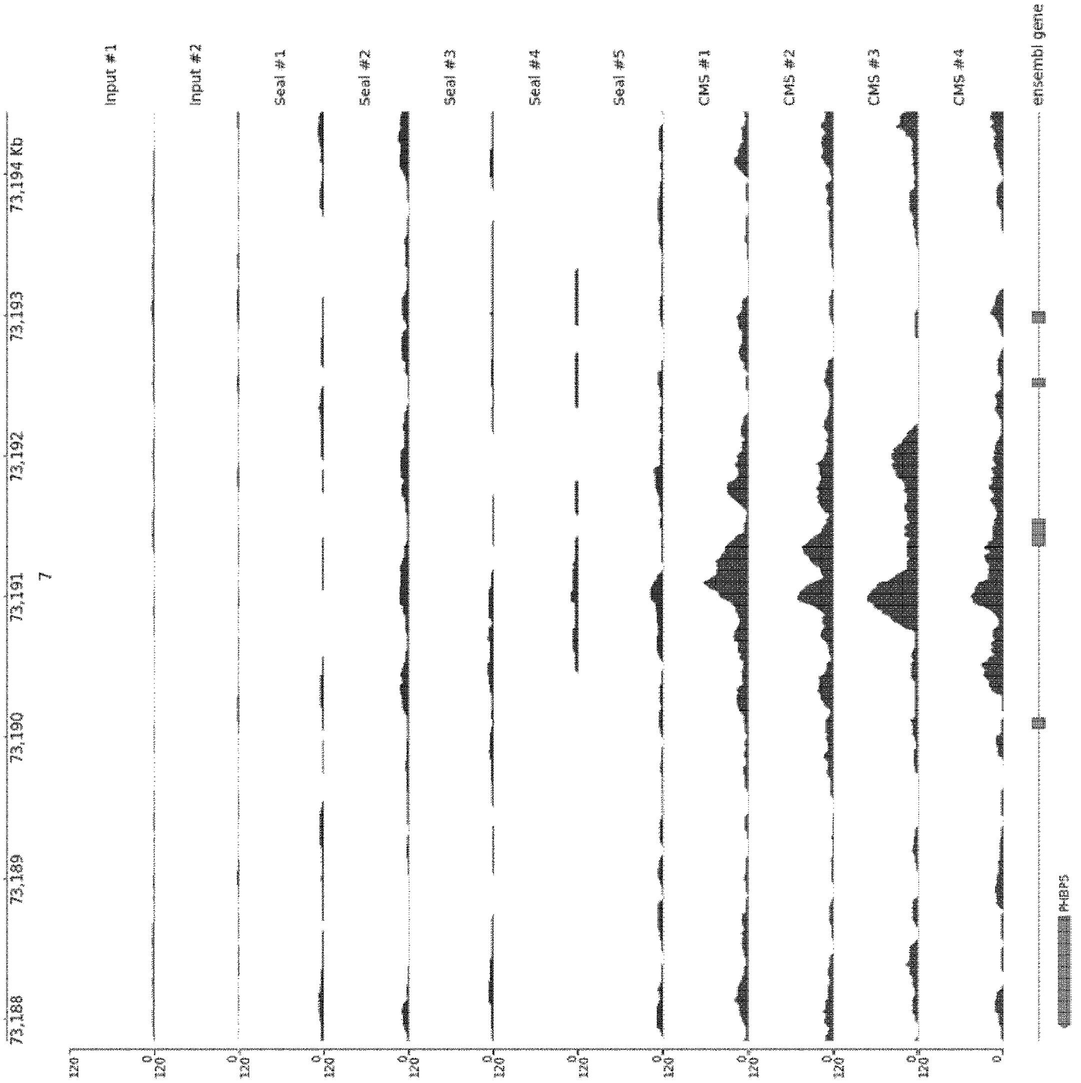
FIGS. 31A-31B show two example regions in the human genome, highlighting enrichment in each region using the different techniques
Figure 31B:
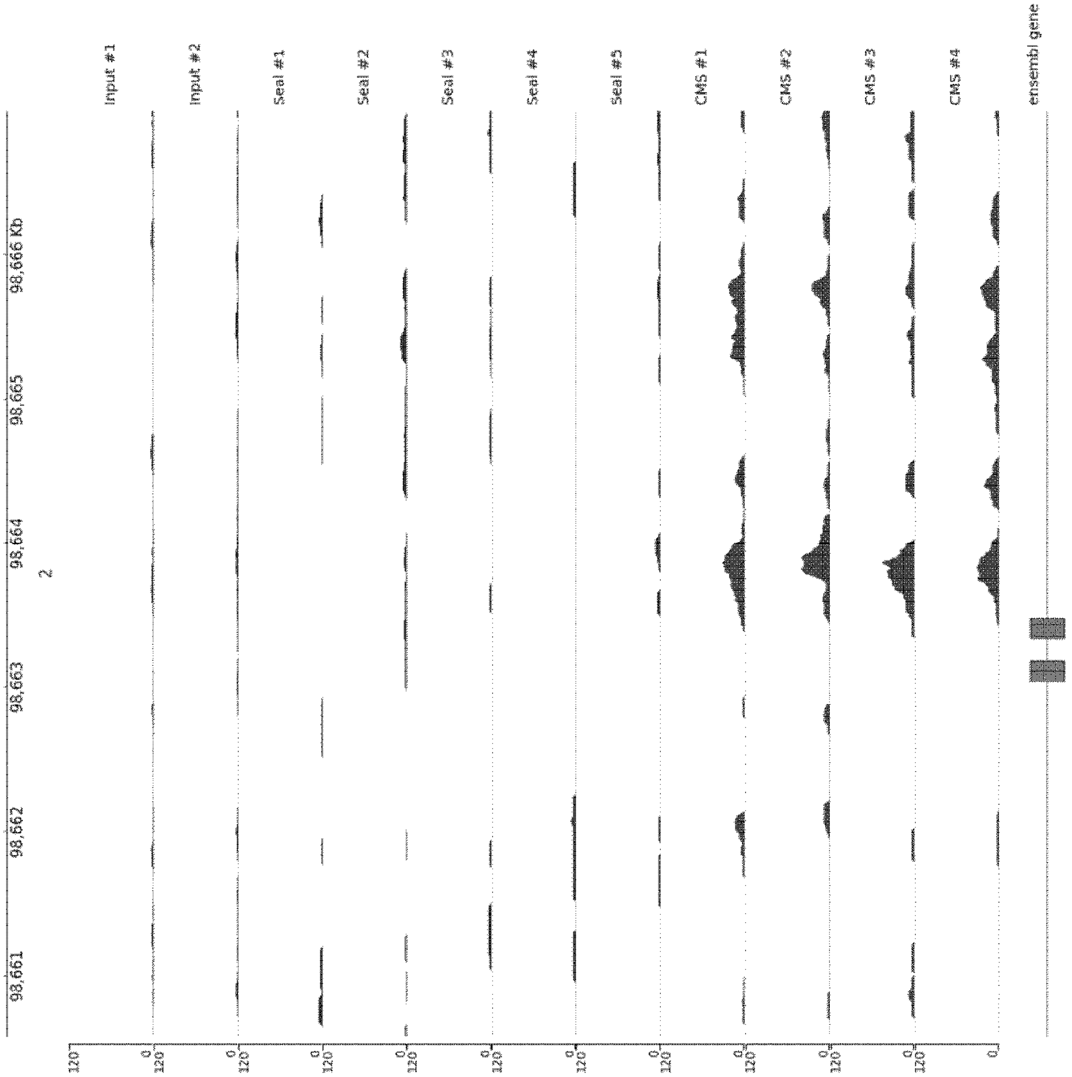

Encouraged by the good results starting from 50 ng mES gDNA, next the method was applied to cell-free DNA (cfDNA). 5-Hydroxymethylcytosine signatures in circulating cfDNA can be used as diagnostic biomarkers for cancers and some other diseases. For cfDNA, it is challenging to get a large amount of cfDNA from each patient, but 10 ng is usually practical. Therefore, the inventors tried to build NGS sequencing libraries using 10 ng cfDNA from healthy people and cancer patients to compare the library quality of hMeDIP, 5hmC-Seal and new anti-CMS method. The fraction of unique reads in both the new CMS and 5hmC-Seal method was higher than hMeDIP method, and the new CMS method was more consistent among replicates (FIG. 24). The size of insert fragments in all the libraries showed similar pattern, which is consistent with the cfDNA fragment length in plasma (FIG. 25). The PCA using all the detected peaks from cfDNA samples showed that the new CMS method was more robust than 5hmC-Seal and hMeDIP method (FIG. 26). In addition, the distribution of the 5hmC peak along the gene body (metagene profile) can also be used as a method to assess the enrichment efficiency of hMeDIP, 5hmC-Seal and the disclosed new CMS method. The new CMS method was more consistent with the 5hmC-Seal method, while the hMeDIP signal appeared very noisy (FIG. 27). For the new CMS method, 2 technical replicates libraries were built for 2 kinds of cfDNA samples, one was from healthy plasma donor (CMS #1 and CMS #2), and the other was from a cancer patient (CMS #3 and CMS #4). All technical replicates were highly consistent (FIG. 27). Meanwhile, the new CMS method could show the difference between healthy and cancer samples. Similar to 5hmC-Seal, the new CMS method could capture the 5hmC valley near the transcription starting site (FIG. 28). Interestingly, the CMS method could detect a 5hmC peak near the transcription end site (TES), while only one of the 5hmC-Seal libraries shows enrichment near the TES (FIG. 29). By comparing the fold change of peak intensity, it was discovered that the new CMS method could capture more than 5,000 significant enrichment region in the human genome (FIG. 30). This provides a greater opportunity to identify a potential biomarker. Compared with other methods, the new CMS method produced some specific peaks suggesting higher enrichment efficiency (FIGS. 31A-31B).

Example 5hmC Treatment Conditions for CMS Method:

400 μl amount of water was added to 400 mg ammonium sulfite monohydrate to prepare 50% ammonium sulfite. Then, 450 μl of this 50% ammonium sulfite solution was mixed with 40 μl 70% ammonium bisulfite, the solution was pH adjusted to between 6.8 and 7.2, vortexed and spun.

45 μl freshly prepared reagent was added to sample DNA in 5 μl DNase-free water was added, vortexed and spun, then incubated at 98° C. for 10 min, followed by desulphonation.

Example 3—Enrichment of RNA Fragments Containing $hm^5C$

A sample of RNA fragments, a portion of which contain hydroxymethyl cytosine ($hm^5C$), are treated with non-conventional bisulfite conditions as described in Example 2 to convert the $hm^5C$ into CMS. The modified RNA fragments containing the CMS are incubated with an anti-CMS antibody, purified from the mixture, and subjected to reverse transcription to generate cDNA. The cDNA is subjected to next generation sequencing to identify the location of each $hm^5C$ in the original sample.

All of the methods disclosed and claimed herein can be made and executed without undue experimentation in light of the present disclosure. While the compositions and methods of this invention have been described in terms of certain embodiments, it will be apparent to those of skill in the art that variations may be applied to the methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

[1] Khoddami, V. et al. Transcriptome-wide profiling of multiple RNA modifications simultaneously at single-base resolution. *Proc. Natl. Acad. Sci. U.S.A* 116, 6784-6789 (2019).

[2] Li, X. et al. Chemical pulldown reveals dynamic pseudouridylation of the mammalian transcriptome. *Nat. Chem. Biol.* 11, 592-7 (2015).

[3] Rintala-Dempsey, A. C. & Kothe, U. Eukaryotic standalone pseudouridine synthases-RNA modifying enzymes and emerging regulators of gene expression? *RNA Biology* 14, 1185-1196 (2017).

[4] Hamma, T. & Ferré-D'Amaré, A. R. Pseudouridine synthases. *Chemistry and Biology* 13, 1125-1135 (2006).

[5] Penzo, M., Guerrieri, A. N., Zacchini, F., Trere, D. & Montanaro, L. RNA pseudouridylation in physiology and medicine: For better and for worse. *Genes* (*Basel*) 8, (2017).

[6] Grozdanov P N, Fernandez-Fuentes N, Fiser A, Meier U T. Pathogenic NAP57 mutations decrease ribonucleoprotein assembly in dyskeratosis congenita. *Hum Mol Genet.* 2009; 18(23):4546-51. PMID: 19734544; PMCID: PMC2773269.

[7] Heiss, N. S. et al. X-linked dyskeratosis congenita is caused by mutations in a highly conserved gene with putative nucleolar functions. *Nat. Genet.* 19, 32-38 (1998).

[8] Hee Lee, S., Kim, I. & Chul Chung, B. Increased urinary level of oxidized nucleosides in patients with mild-to-moderate Alzheimer's disease. *Clin. Biochem.* 40, 936-938 (2007).

[9] Safra, M., Nir, R., Farouq, D., Slutzkin, I. V. & Schwartz, S. TRUB1 is the predominant pseudouridine synthase acting on mammalian mRNA via a predictable and conserved code. *Genome Res.* 27, 393-406 (2017).

[10] Jambhekar, A. & Derisi, J. L. Cis-acting determinants of asymmetric, cytoplasmic RNA transport. *RNA* 13, 625-642 (2007).

[11] Kudla, G., Murray, A. W., Tollervey, D. & Plotkin, J. B. Coding-sequence determinants of expression in *Escherichia coli. Scienc.* 324, 255-258 (2009).

[12] Somogyi, P., Jenner, A. J., Brierley, I. & Inglis, S. C. Ribosomal pausing during translation of an RNA pseudoknot. *Mol. Cell. Biol.* 13, 6931-6940 (1993).

[13] Shah, P., Ding, Y., Niemczyk, M., Kudla, G. & Plotkin, J. B. Rate-limiting steps in yeast protein translation. *Cell* 153, 1589-1601 (2013).

[14] Tan, X. et al. Tiling genomes of pathogenic viruses identifies potent antiviral shRNAs and reveals a role for secondary structure in shRNA efficacy. *Proc. Natl. Acad. Sci. U.S.A* 109, 869-874 (2012).

[15] Bakin, A. & Ofengand, J. Four newly located pseudouridylate residues in *Escherichia coli* 23S ribosomal RNA are all at the peptidyltransferase center: analysis by the application of a new sequencing technique. *Biochemistry* 32, 9754-9762 (1993).

[16] Schwartz, S. et al. Transcriptome-wide mapping reveals widespread dynamic-regulated pseudouridylation of ncRNA and mRNA. *Cell* 159, 148-162 (2014).

[17] Carlile, T. M. et al. Pseudouridine profiling reveals regulated mRNA pseudouridylation in yeast and human cells. *Nature* 515, 143-146 (2014).

[18] Hayatsu, H., Wataya, Y., Kai, K. & Iida, S. Reaction of sodium bisulfite with uracil, cytosine, and their derivatives. Biochemistry 9, 2858-2865 (1970).

[19] Babaian, A. et al. Loss of $m^1acp^3\Psi$ ribosomal RNA modification is a major feature of cancer. Cell Rep. 31, (2020).

[20] Huang, Y. et al The anti-CMS technique for genome-wide mapping of 5-hydroxymethylcytosine, *Nat Protoc.* 7, 1897-1908 (2012).

[21] Pastor, W. A. et al. Genome-wide mapping of 5-hydroxymethylcytosine in embryonic stem cells, *Nature* 473, 394-7 (2011).

[22] Delatte, B. et al. Transcriptome-wide distribution and function of RNA hydroxymethylcytosine, *Science* 351, 282-5 (2016)

The invention claimed is:

1. A method for modifying a pseudouridine comprising incubating a ribonucleic acid (RNA) molecule comprising the pseudouridine with bisulfite at a pH of between about 6.9 and about 7.1, to generate a modified RNA molecule comprising a modified pseudouridine, wherein incubating the RNA molecule is performed at a temperature of between about 65° C. and about 75° C. for between 2 hours and 6 hours.

2. The method of claim 1, wherein incubating the RNA molecule with the bisulfite does not comprise adding hydroquinone.

3. The method of claim 1, wherein the bisulfite is at least 10% sodium bisulfite by weight.

4. The method of claim 1, further comprising subjecting the modified RNA molecule to reverse transcription using a reverse transcriptase enzyme to generate a deoxyribonucleic acid (DNA) molecule.

5. The method of claim 4, further comprising sequencing the DNA molecule.

6. The method of claim 1, wherein the RNA molecule is an RNA molecule of a plurality of RNA molecules, wherein the method further comprises quantifying the number of pseudouridines in the plurality of RNA molecules.

7. The method of claim 1, wherein the RNA molecule is from a cell-free RNA sample.

8. A method for modifying a 5-hydroxymethylcytosine comprising incubating a ribonucleic acid (RNA) molecule comprising the 5-hydroxymethylcytosine with bisulfite at pH of between about 6.9 and about 7.1, to generate a modified RNA molecule comprising cytosine-5-methylenesulfonate (CMS), wherein incubating the RNA molecule is performed at a temperature of at least about 95° C. for less than 30 minutes.

9. The method of claim 8, wherein the pH is between about 6.9 and 7.1.

10. The method of claim 8, wherein incubating the RNA molecule with the bisulfite does not comprise adding hydroquinone.

11. The method of claim 8, wherein the bisulfite is at at least 10% sodium bisulfite by weight.

12. The method of any of claim 8, further comprising detecting the CMS in the modified RNA molecule.

13. The method of claim 8, further comprising subjecting the modified RNA molecule to reverse transcription using a reverse transcriptase enzyme to generate a deoxyribonucleic acid (DNA) molecule.

14. The method of claim 13, further comprising sequencing the DNA molecule.

15. The method of claim 8, wherein the RNA molecule is from a cell-free RNA sample.

16. A method for modifying a 5-hydroxymethylcytosine comprising incubating a deoxyribonucleic acid (DNA) molecule comprising the 5-hydroxymethylcytosine with bisulfite at a pH of between about 6.9 and about 7.1, to generate a nucleic acid molecule comprising cytosine-5-methylenesulfonate (CMS), wherein incubating the DNA molecule is performed at a temperature of at least about 95° C. for less than 30 minutes.

* * * * *

SEQUENCE LISTING

<160> NUMBER OF SEQ ID NOS: 11

<210> SEQ ID NO 1
<211> LENGTH: 5
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (3)..(3)

<223> OTHER INFORMATION: n is C or pseudouridine

<400> SEQUENCE: 1 agnga 5

<210> SEQ ID NO 2
<211> LENGTH: 5
<212> TYPE: RNA
<213> ORGANISM: Artificial Sequence
<220> FEATURE:
<223> OTHER INFORMATION: Synthetic polynucleotide

<400> SEQUENCE: 2 agcga 5

<210> SEQ ID NO 3
<211> LENGTH: 5
<212> TYPE: RNA
<213> ORGANISM: Artificial Sequence
<220> FEATURE:
<223> OTHER INFORMATION: Synthetic polynucleotide

<400> SEQUENCE: 3 aguga 5

<210> SEQ ID NO 4
<211> LENGTH: 5
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (3)..(3)
<223> OTHER INFORMATION: p
<220> FEATURE:
<221> NAME/KEY: misc_feature
<222> LOCATION: (3)..(3)
<223> OTHER INFORMATION: n is a, c, g, or u

<400> SEQUENCE: 4 agnga 5

<210> SEQ ID NO 5
<211> LENGTH: 19
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (10)..(10)
<223> OTHER INFORMATION: n is a, c, g, or u

<400> SEQUENCE: 5
guacgucagn cagacugac 19

<210> SEQ ID NO 6
<211> LENGTH: 19
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (8)..(9)
<223> OTHER INFORMATION: n is A, C, G, or U
<220> FEATURE:
<221> NAME/KEY: modified_base
<222> LOCATION: (10)..(10)
<223> OTHER INFORMATION: p
<220> FEATURE:
<221> NAME/KEY: misc_feature
<222> LOCATION: (10)..(10)
<223> OTHER INFORMATION: n is a, c, g, or u
<220> FEATURE:
<221> NAME/KEY: misc_feature
<222> LOCATION: (11)..(12)
<223> OTHER INFORMATION: n is A, C, G, or U

<400> SEQUENCE: 6
agcuagunnn nnuagugac 19

<210> SEQ ID NO 7
<211> LENGTH: 19
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (10)..(10)
<223> OTHER INFORMATION: p
<220> FEATURE:
<221> NAME/KEY: misc_feature
<222> LOCATION: (10)..(10)
<223> OTHER INFORMATION: n is a, c, g, or u

<400> SEQUENCE: 7
agcuagucan aauagugac 19

<210> SEQ ID NO 8
<211> LENGTH: 5
<212> TYPE: DNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (3)..(3)
<223> OTHER INFORMATION: 5-hydroxymethylcytosine
<220> FEATURE:
<221> NAME/KEY: misc_feature
<222> LOCATION: (3)..(3)
<223> OTHER INFORMATION: n is a, c, g, or t

<400> SEQUENCE: 8 acngt 5

<210> SEQ ID NO 9
<211> LENGTH: 5
<212> TYPE: RNA
<213> ORGANISM: Artificial Sequence
<220> FEATURE:
<223> OTHER INFORMATION: Synthetic polynucleotide
<220> FEATURE:
<221> NAME/KEY: modified_base
<222> LOCATION: (3)..(3)
<223> OTHER INFORMATION: 5-hydroxymethylcytosine
<220> FEATURE:
<221> NAME/KEY: misc_feature
<222> LOCATION: (3)..(3)
<223> OTHER INFORMATION: n is a, c, g, or u

<400> SEQUENCE: 9 acngu 5

<210> SEQ ID NO 10
<211> LENGTH: 32
<212> TYPE: DNA

-continued

```
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: n is A, C, G, or T

<400> SEQUENCE: 10

nnnnncgatg tagatcggaa gagcacacgt ct                                32


<210> SEQ ID NO 11
<211> LENGTH: 31
<212> TYPE: RNA
<213> ORGANISM: Artificial Sequence
<220> FEATURE:
<223> OTHER INFORMATION: Synthetic polynucleotide
<220> FEATURE:
<221> NAME/KEY: misc_feature
<222> LOCATION: (1)..(5)
<223> OTHER INFORMATION: n is A, C, G, or U
<220> FEATURE:
<221> NAME/KEY: misc_feature
<222> LOCATION: (27)..(31)
<223> OTHER INFORMATION: n is a, c, g, or u

<400> SEQUENCE: 11

guucagaguu cuacaguccg acgaucnnnn n                                 31
```